(12) United States Patent
Jun et al.

(10) Patent No.: US 9,732,099 B1
(45) Date of Patent: Aug. 15, 2017

(54) ORGANIC ELECTROLUMINESCENT COMPOUNDS AND ORGANIC ELECTROLUMINESCENT DEVICES COMPRISING THE SAME

(71) Applicant: Rohm and Haas Electronic Materials Korea Ltd., Cheonan (KR)

(72) Inventors: Ji-Song Jun, Hwaseong (KR); Sang-Hee Cho, Suwon (KR); Kyoung-Jin Park, Seongnam (KR)

(73) Assignee: ROHM AND HAAS ELECTRONIC MATERIALS KOREA LTD., Cheonan-si (KR)

(*) Notice: Subject to any disclaimer, the term of this patent is extended or adjusted under 35 U.S.C. 154(b) by 0 days.

(21) Appl. No.: 15/501,260

(22) PCT Filed: Aug. 7, 2015

(86) PCT No.: PCT/KR2015/008307
§ 371 (c)(1),
(2) Date: Feb. 2, 2017

(87) PCT Pub. No.: WO2016/021989
PCT Pub. Date: Feb. 11, 2016

(30) Foreign Application Priority Data

Aug. 8, 2014 (KR) .................. 10-2014-0102563
Aug. 5, 2015 (KR) .................. 10-2015-0110740

(51) Int. Cl.
| | | |
|---|---|---|
| *C07D 491/10* | (2006.01) |
| *H01L 51/50* | (2006.01) |
| *C07D 519/00* | (2006.01) |
| *C07D 495/22* | (2006.01) |
| *C07D 495/20* | (2006.01) |
| *C07D 495/10* | (2006.01) |
| *C07D 493/22* | (2006.01) |
| *C07D 493/20* | (2006.01) |
| *C07D 493/10* | (2006.01) |

(52) U.S. Cl.
CPC .......... *C07D 519/00* (2013.01); *C07D 493/10* (2013.01); *C07D 493/20* (2013.01); *C07D 493/22* (2013.01); *C07D 495/10* (2013.01); *C07D 495/20* (2013.01); *C07D 495/22* (2013.01)

(58) Field of Classification Search
CPC ............................. C07D 491/10; H01L 51/50
USPC .................................. 548/407, 417; 313/504
See application file for complete search history.

(56) References Cited

U.S. PATENT DOCUMENTS

2014/0225040 A1  8/2014  Parham et al.
2015/0144937 A1  5/2015  Park et al.

FOREIGN PATENT DOCUMENTS

| CN | 101870865 A | 10/2010 |
|---|---|---|
| JP | 4947909 B2 | 6/2012 |
| KR | 2012-0092550 A | 8/2012 |
| KR | 2014-0076522 A | 6/2014 |
| WO | 2013/149958 A1 | 10/2013 |
| WO | 2014/072017 A1 | 5/2014 |

*Primary Examiner* — Charanjit Aulakh
(74) *Attorney, Agent, or Firm* — Jae Choon You

(57) ABSTRACT

The present invention relates to an organic electroluminescent compound and an organic electroluminescent device comprising the same. By using the organic electroluminescent compound of the present invention, it is possible to produce an organic electroluminescent device having low driving voltage and excellent luminous efficiency such as current efficiency and power efficiency, emitting color of high purity, and having improved lifespan.

6 Claims, No Drawings

ORGANIC ELECTROLUMINESCENT COMPOUNDS AND ORGANIC ELECTROLUMINESCENT DEVICES COMPRISING THE SAME

TECHNICAL FIELD

The present invention relates to an organic electroluminescent compound and an organic electroluminescent device comprising the same.

BACKGROUND ART

Since a double-layered, small molecular, green light-emitting organic electroluminescent device (OLED) was firstly developed by Tang, et al., of Eastman Kodak in 1987, which comprises TPD/Alq$_3$ as a light-emitting layer and a charge transport layer, the development of organic electroluminescent devices has been rapidly achieved, and thus organic electroluminescent devices have currently reached commercialization. At present, an organic electroluminescent device usually uses phosphorescent materials having high luminous efficiency for the realization of panels. In the case of organic electroluminescent devices emitting red or green light, although organic electroluminescent devices using phosphorescent materials have been successfully commercialized, blue light-emitting phosphorescent materials have the following disadvantages: Due to the disappearance of excessive formed excitons, roll-off at high current is reduced thereby resulting in degradation of characteristics; blue light-emitting phosphorescent materials have a problem with respect to long-term storage stability; and color purity is rapidly reduced with the passage of time, and thus it is difficult to realize a full-color display.

Fluorescent light-emitting materials which are currently used also have many problems. First, when they are exposed to a high temperature in the process of the manufacture of panels, current properties may be changed in the organic electroluminescent devices thereby changing the light-emitting luminance, and due to the structural nature, luminance may be reduced according to the reduction in properties of an interface between a light-emitting layer and an electron injection layer. Furthermore, fluorescent light-emitting materials have lower efficiency than phosphorescent light-emitting materials in a material aspect. Although the efficiency improvement was attempted by certain fluorescent light-emitting materials such as the combination of anthracene-based host and pyrene-based dopant, since the materials have a large hole trap, they have a tendency to emit light at the interface with the light-emitting zone in a light-emitting layer being biased toward a hole transport layer. Such light-emitting at the interface not only reduces the lifespan of organic electroluminescent devices but also does not achieve satisfactory efficiency.

The above problems of fluorescent light-emitting materials are no longer possible to be overcome by the mere improvement of materials per se. Thus, attempts are currently being made to change charge movement properties by improving charge transport materials or solve the problems by developing optimized device structures.

Korean Patent Application Laying-open No. 10-2012-0092550 discloses an organic electroluminescent device in which a blocking layer comprising aromatic heterocyclic derivatives having an azine ring is disposed between an electron injection layer and a light-emitting layer.

Japanese Patent No. 4947909 presents a blue fluorescent light-emitting device comprising an electron buffer layer, which efficiently injects electrons to a light-emitting layer compared with Alq$_3$ and controls the movement of electrons, and thereby prevents the reduction of driving voltage and the degradation due to the light-emitting at an interface, and improves the lifespan of the device.

Chinese Patent Application Laying-open No. CN 101870865, and International Publication Nos. WO 2013/149958 A1 and WO 2014/072017 A1 disclose spiro[fluorene-9,9'-xanthene] derivatives.

However, none of the above literature disclose organic electroluminescent compounds in which a benzene ring of the fluorene in the spiro[fluorene-9,9'-xanthene] backbone is fused with benzofuran, benzothiophene, or indole.

DISCLOSURE OF THE INVENTION

Problems to be Solved

The object of the present invention is to provide an organic electroluminescent device having low driving voltage, high luminous efficiency, and long driving lifespan.

Solution to Problems

The above objective can be achieved by an organic electroluminescent compound represented by the following formula 1:

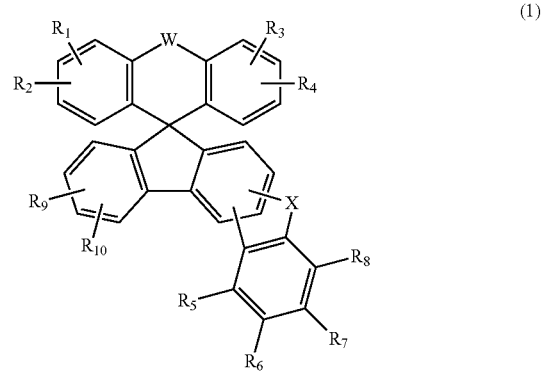

wherein

W represents O or S;

X represents O, S, or NR$_{11}$;

R$_1$ to R$_{11}$ each independently represent hydrogen, deuterium, a halogen, a cyano group, a substituted or unsubstituted (C1-C30)alkyl group, a substituted or unsubstituted (C6-C30)aryl group, a substituted or unsubstituted 3- to 30-membered heteroaryl group, a substituted or unsubstituted (C3-C30)cycloalkyl group, a substituted or unsubstituted (C1-C30)alkoxy group, a substituted or unsubstituted tri(C1-C30)alkylsilyl group, a substituted or unsubstituted di(C1-C30)alkyl(C6-C30)arylsilyl group, a substituted or unsubstituted (C1-C30)alkyldi(C6-C30)arylsilyl group, a substituted or unsubstituted tri(C6-C30)arylsilyl group, a substituted or unsubstituted mono- or di-(C1-C30)alkylamino group, a substituted or unsubstituted mono- or di-(C6-C30)arylamino group, or a substituted or unsubstituted (C1-C30)alkyl(C6-C30)arylamino group; or are linked to an adjacent substituent(s) to form a substituted or unsubstituted mono- or polycyclic, (C3-C30) alicyclic or aromatic ring, whose carbon atom(s) may be replaced with at least one hetero atom selected from nitrogen, oxygen, and sulfur; and the heteroaryl group contains at least one hetero atom selected from B, N, O, S, Si, and P.

Effects of the Invention

The organic electroluminescent compound of the present invention can provide an organic electroluminescent device having low driving voltage and high luminous efficiency such as current efficiency and power efficiency, and showing good color purity and improved lifespan.

EMBODIMENTS OF THE INVENTION

Hereinafter, the present invention will be described in detail. However, the following description is intended to explain the invention, and is not meant in any way to restrict the scope of the invention.

The present invention relates to an organic electroluminescent compound represented by formula 1 and an organic electroluminescent device comprising the same.

The organic electroluminescent compound represented by formula 1 will be described in detail as follows.

Herein, "alkyl" may be specifically exemplified as methyl, ethyl, n-propyl, isopropyl, n-butyl, isobutyl, tert-butyl, etc. "Cycloalkyl" may be specifically exemplified as cyclopropyl, cyclobutyl, cyclopentyl, cyclohexyl, etc. "3- to 7-membered heterocycloalkyl" is a cycloalkyl having at least one heteroatom selected from the group consisting of B, N, O, S, Si, and P, preferably O, S, and N, and 3 to 7 ring backbone atoms, and includes tetrahydrofuran, pyrrolidine, thiolan, tetrahydropyran, etc. "Aryl(ene)" is a monocyclic or fused ring-based radical derived from an aromatic hydrocarbon; contains spiro compounds in which two rings are linked by one atom, and includes phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, etc. "3- to 30-membered heteroaryl(ene)" is an aryl group having at least one, preferably 1 to 4, heteroatom selected from the group consisting of B, N, O, S, Si, and P, preferably O, S, and N, and 3 to 30 ring backbone atoms; is a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzimidazolyl, benzothiazolyl, benzisothiazolyl, benzisoxazolyl, benzoxazolyl, isoindolyl, indolyl, indazolyl, benzothiadiazolyl, quinolyl, isoquinolyl, cinnolinyl, quinazolinyl, quinoxalinyl, pyridopyrimidinyl, carbazolyl, phenoxazinyl, phenanthridinyl, benzodioxolyl, dihydroacridinyl, benzofuroindole, etc. "Halogen" includes F, Cl, Br, and I.

Herein, "substituted" in the expression "substituted or unsubstituted" means that a hydrogen atom in a certain functional group is replaced with another atom or group, i.e., a substituent. Substituents of the substituted alkyl group, the substituted aryl group, the substituted heteroaryl group, the substituted cycloalkyl group, the substituted alkoxy group, the substituted trialkylsilyl group, the substituted dialkylarylsilyl group, the substituted alkyldiarylsilyl group, the substituted triarylsilyly group, the substituted mono- or di-alkylamino group, the substituted mono- or di-arylamino group, the substituted alkylarylamino group, and the substituted mono- or polycyclic, alicyclic or aromatic ring in $R_1$ to $R_{11}$ of formula 1 are each independently at least one selected from the group consisting of deuterium; a halogen; a cyano group; a carboxyl group; a nitro group; a hydroxyl group; a (C1-C30)alkyl group; a halo(C1-C30)alkyl group; a (C1-C30)alkoxy group; a (C1-C30)alkylthio group; a (C3-C30)cycloalkyl group; a 3- to 7-membered heterocycloalkyl group; a (C6-C30)aryloxy group; a (C6-C30)arylthio group; a 3- to 30-membered heteroaryl group which is unsubstituted or substituted with a (C6-C30)aryl group; a (C6-C30)aryl group which is unsubstituted or substituted with a 3- to 30-membered heteroaryl group; a tri(C1-C30)alkylsilyl group; a tri(C6-C30)arylsilyl group; a di(C1-C30)alkyl(C6-C30)arylsilyl group; a (C1-C30)alkyldi(C6-C30)arylsilyl group; an amino group; a mono- or di-(C1-C30)alkylamino group; a mono- or di-(C6-C30)arylamino group; a (C1-C30)alkyl(C6-C30)arylamino group; a (C1-C30)alkylcarbonyl group; a (C1-C30)alkoxycarbonyl group; a (C6-C30)arylcarbonyl group; a di(C6-C30)arylboronyl group; a di(C1-C30)alkylboronyl group; a (C1-C30)alkyl(C6-C30)arylboronyl group; a (C6-C30)aryl(C1-C30)alkyl group; and a (C1-C30)alkyl(C6-C30)aryl group; and, preferably, at least one selected from the group consisting of a 5- to 20-membered heteroaryl group; a 5- to 20-membered heteroaryl group which is substituted with a (C6-C18)aryl group; a (C6-C18)aryl group; and a (C6-C18)aryl group which is substituted with a 5- to 20-membered heteroaryl group.

W in formula 1 represents O or S.

X in formula 1 represents O, S, or $NR_{11}$.

$R_1$ to $R_{11}$ in formula 1 each independently represent hydrogen, deuterium, a halogen, a cyano group, a substituted or unsubstituted (C1-C30)alkyl group, a substituted or unsubstituted (C6-C30)aryl group, a substituted or unsubstituted 3- to 30-membered heteroaryl group, a substituted or unsubstituted (C3-C30)cycloalkyl group, a substituted or unsubstituted (C1-C30)alkoxy group, a substituted or unsubstituted tri(C1-C30)alkylsilyl group, a substituted or unsubstituted di(C1-C30)alkyl(C6-C30)arylsilylgroup, a substituted or unsubstituted (C1-C30)alkyldi(C6-C30)arylsilyl group, a substituted or unsubstituted tri(C6-C30)arylsilyl group, a substituted or unsubstituted mono- or di-(C1-C30)alkylamino group, a substituted or unsubstituted mono- or di-(C6-C30)arylamino group, or a substituted or unsubstituted (C1-C30)alkyl(C6-C30)arylamino group; or are linked to an adjacent substituent(s) to form a substituted or unsubstituted mono- or polycyclic, (C3-C30) alicyclic or aromatic ring, whose carbon atom(s) may be replaced with at least one hetero atom selected from nitrogen, oxygen, and sulfur.

Preferably, $R_1$ to $R_{10}$ each independently represent hydrogen, or a substituted or unsubstituted (C6-C18)aryl group; or are linked to an adjacent substituent(s) to form a substituted or unsubstituted, mono- or polycyclic, (C6-C20) alicyclic or aromatic ring; and, more preferably, hydrogen, or a (C6-C18)aryl group which is unsubstituted or substituted with a (C6-C18)aryl group or a 5- to 20-membered heteroaryl group; or are linked to an adjacent substituent(s) to form a mono- or polycyclic, (C6-C20) aromatic ring which is unsubstituted or substituted with a (C6-C12)aryl group.

Preferably, $R_{11}$ represents a substituted or unsubstituted (C6-C18)aryl group, or a substituted or unsubstituted 5- to 20-membered heteroaryl group; and more preferably, a (C6-C18)aryl group which is unsubstituted or substituted with a (C6-C18)aryl group or a 5- to 20-membered heteroaryl group, or a 5- to 20-membered heteroaryl group which is unsubstituted or substituted with a (C6-C18)aryl group or a 5- to 20-membered heteroaryl group.

According to one embodiment of the present invention, in formula 1, W represents O or S; X represents O, S, or $NR_{11}$; $R_1$ to $R_{10}$ each independently represent hydrogen, or a substituted or unsubstituted (C6-C18)aryl group; or are linked to an adjacent substituent(s) to form a substituted or unsubstituted, mono- or polycyclic, (C6-C20) alicyclic or aromatic ring; and $R_{11}$ represents a substituted or unsubstituted (C6-C18)aryl group, or a substituted or unsubstituted 5- to 20-membered heteroaryl group.

According to another embodiment of the present invention, in formula 1, W represents O or S; X represents O, S, or $NR_{11}$; $R_1$ to $R_{10}$ each independently represent hydrogen, or a (C6-C18)aryl group which is unsubstituted or substituted with a (C6-C18)aryl group or a 5- to 20-membered heteroaryl group; or are linked to an adjacent substituent(s) to form a mono- or polycyclic, (C6-C20) aromatic ring which is unsubstituted or substituted with a (C6-C12)aryl group; and $R_{11}$ represents a (C6-C18)aryl group which is unsubstituted or substituted with a (C6-C18)aryl group or a 5- to 20-membered heteroaryl group, or a 5- to 20-membered heteroaryl group which is unsubstituted or substituted with a (C6-C18)aryl group or a 5- to 20-membered heteroaryl group.

The compound of formula 1 may be selected from the group consisting of the following compounds, but is not limited thereto:

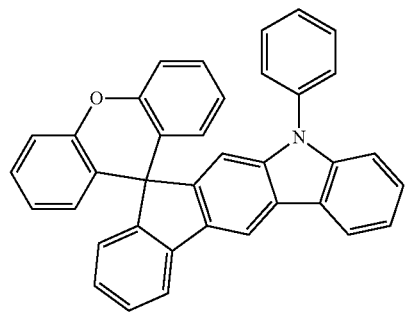

A-1

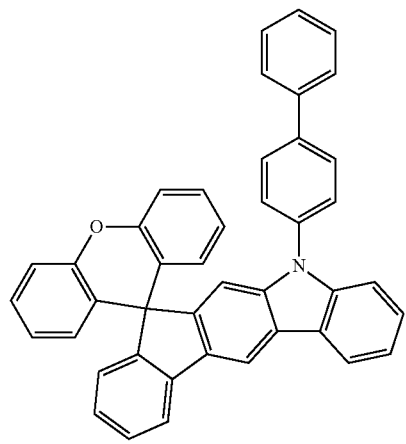

A-2

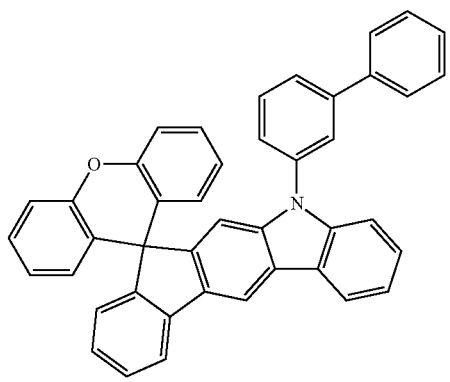

A-3

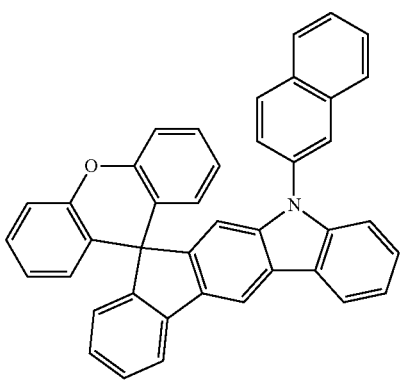

A-4

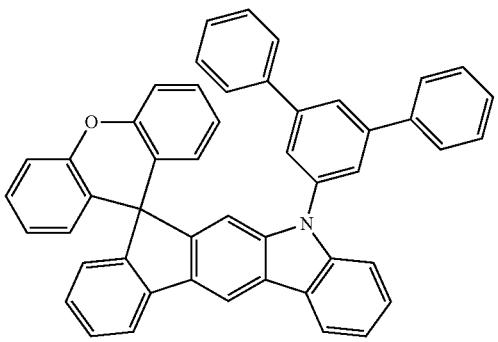

A-5

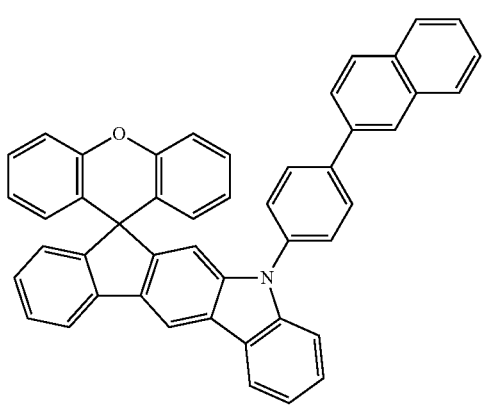

A-6

A-7
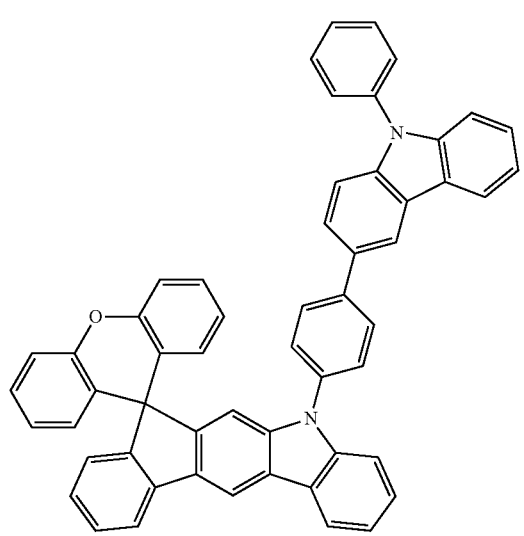
A-8
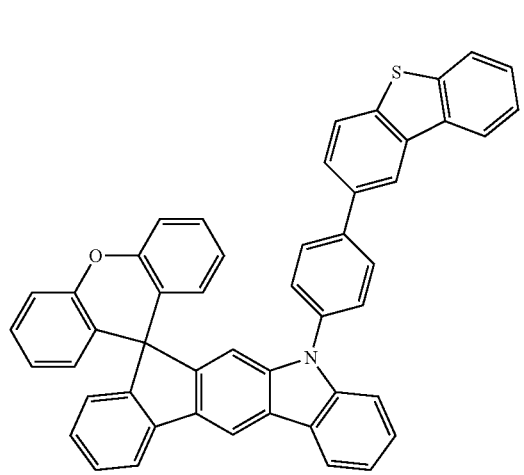
A-9
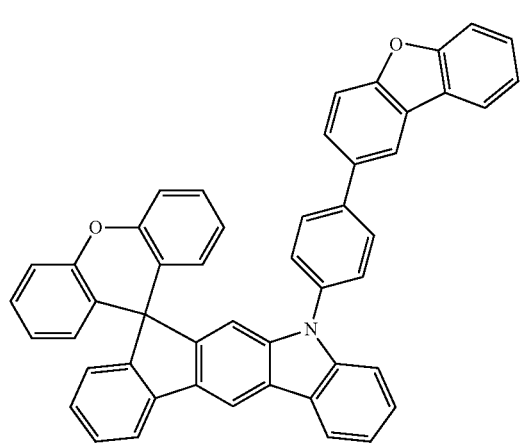
A-10
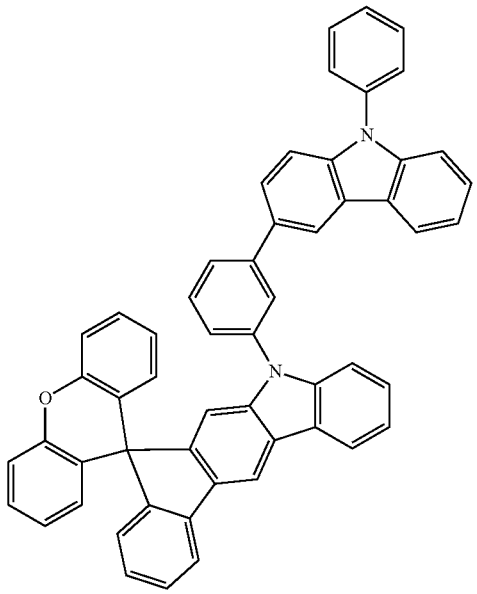
A-11
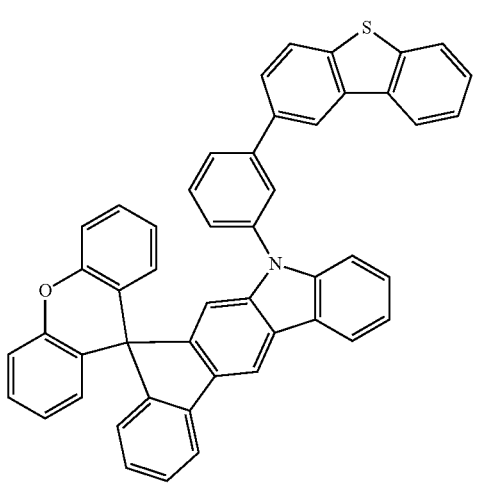
A-12
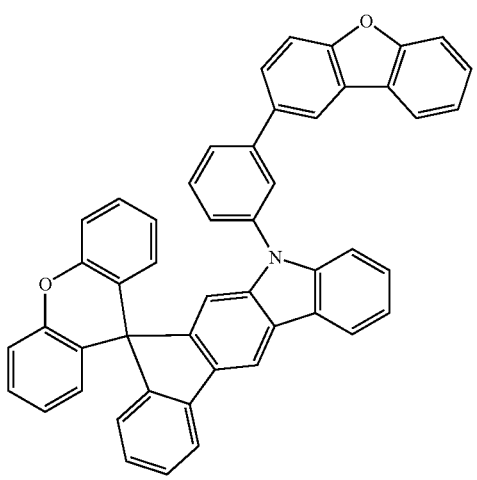

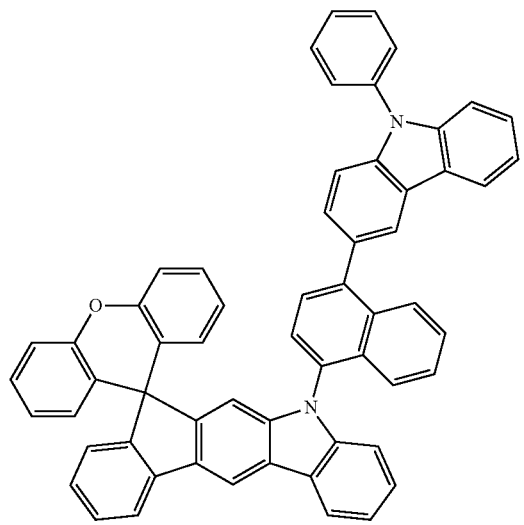
A-13
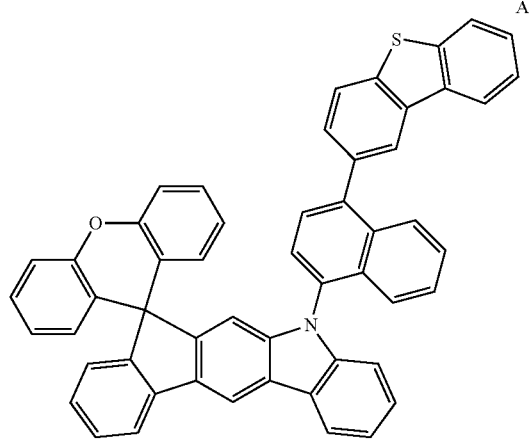
A-14
A-15
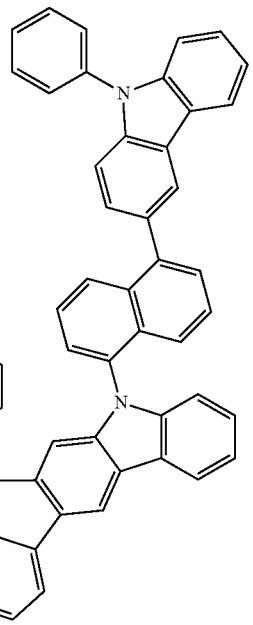
A-16
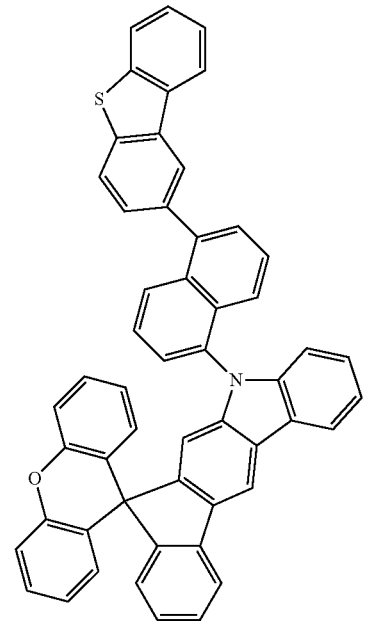
A-17

A-18
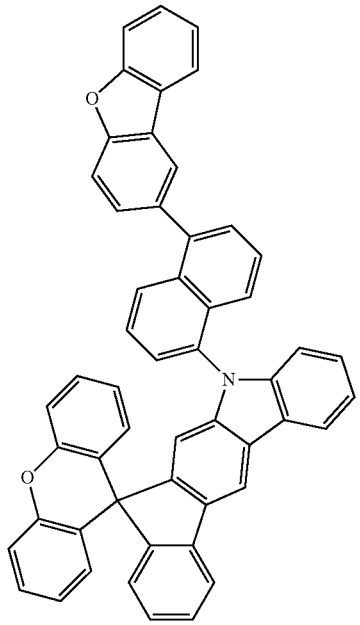
A-19
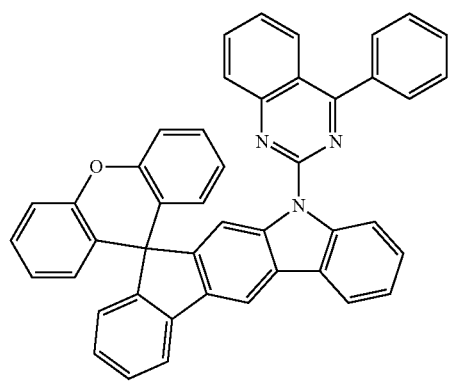
A-20
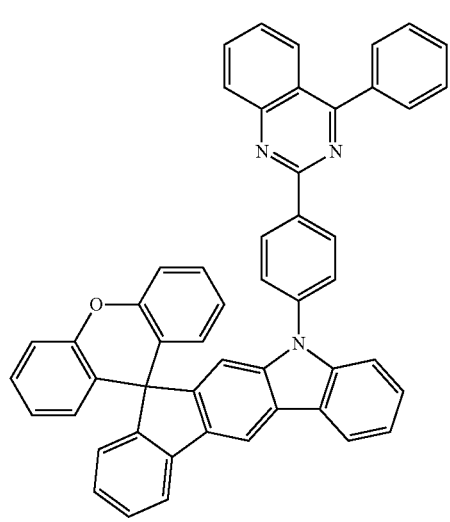
A-21
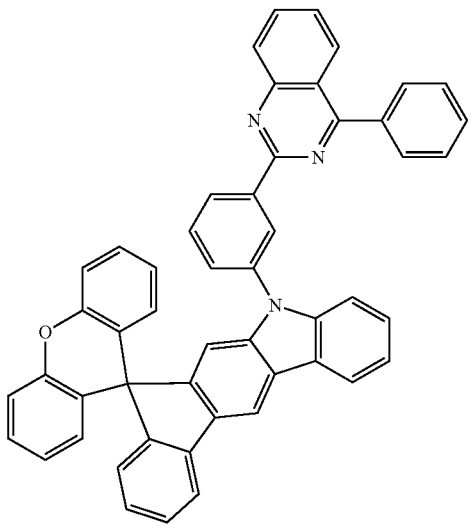
A-22
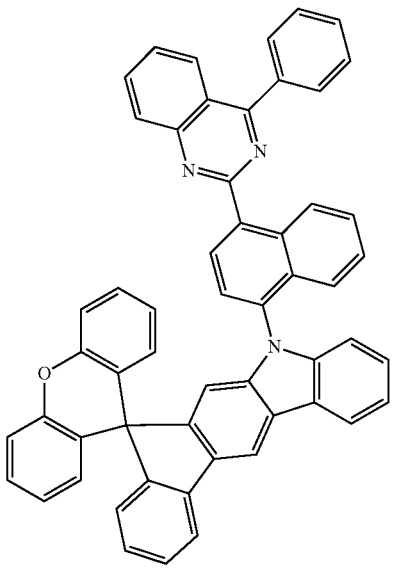
A-23
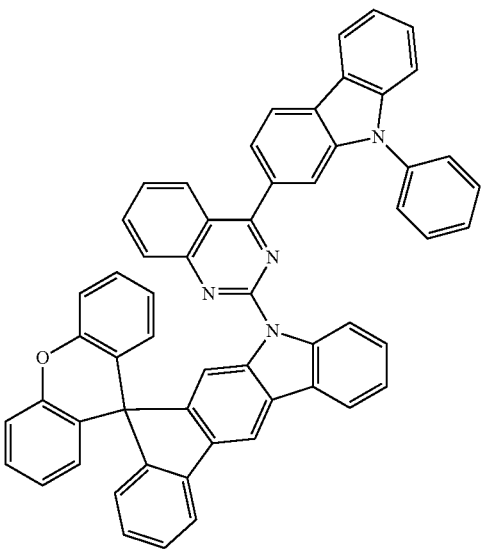

A-24
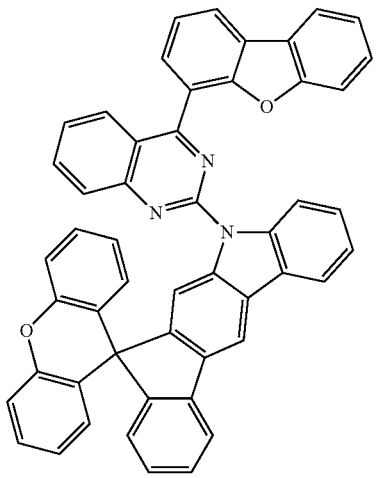
A-25
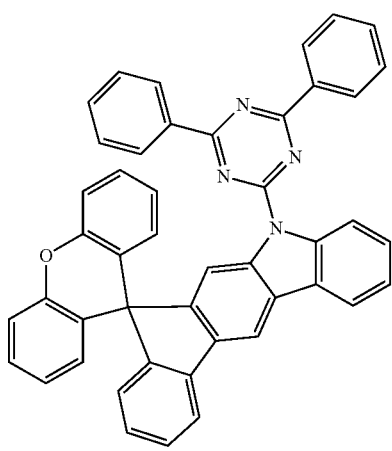
A-26
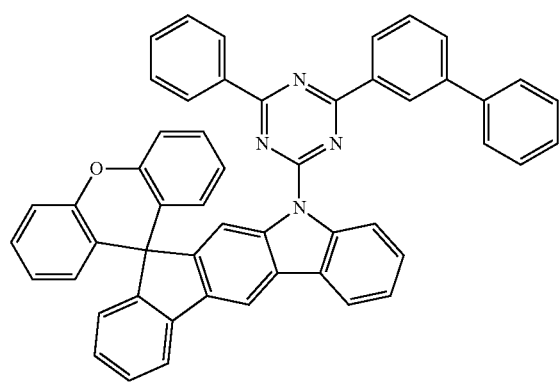
A-27
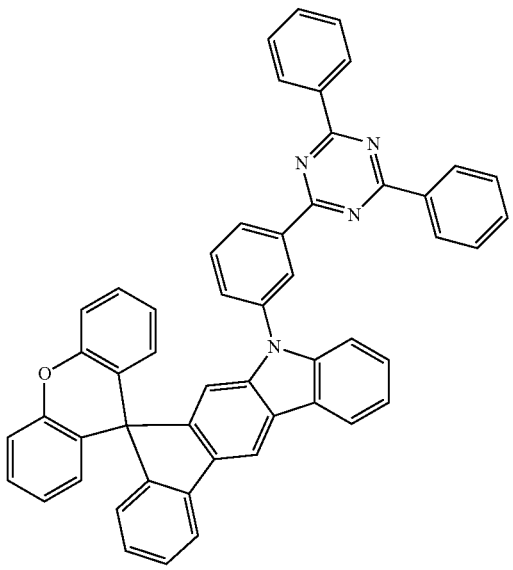
A-28
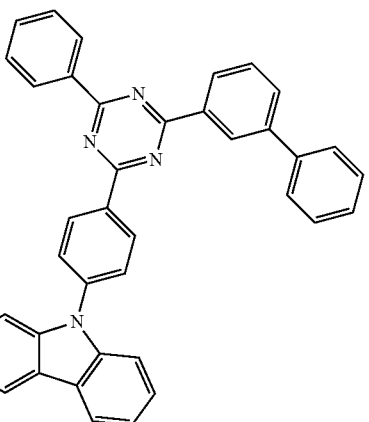
A-29
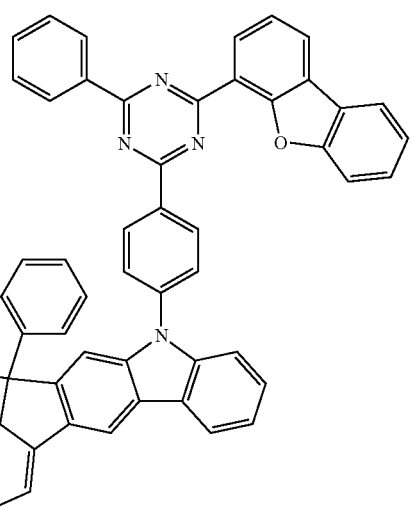

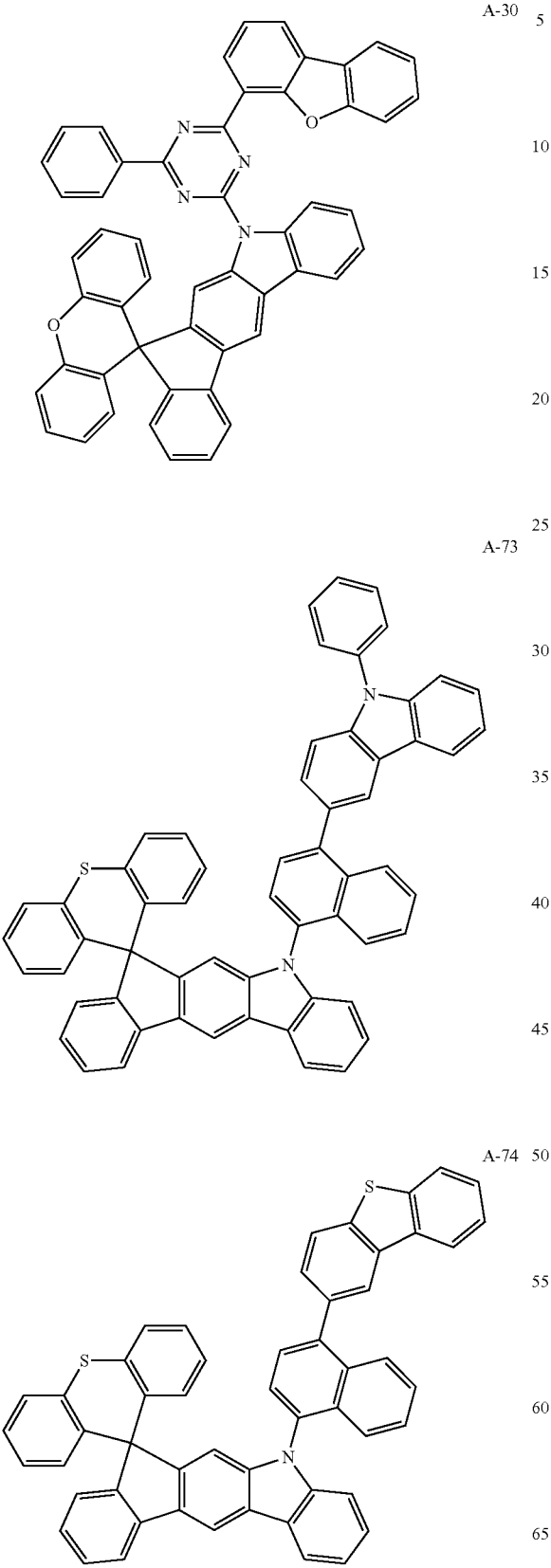
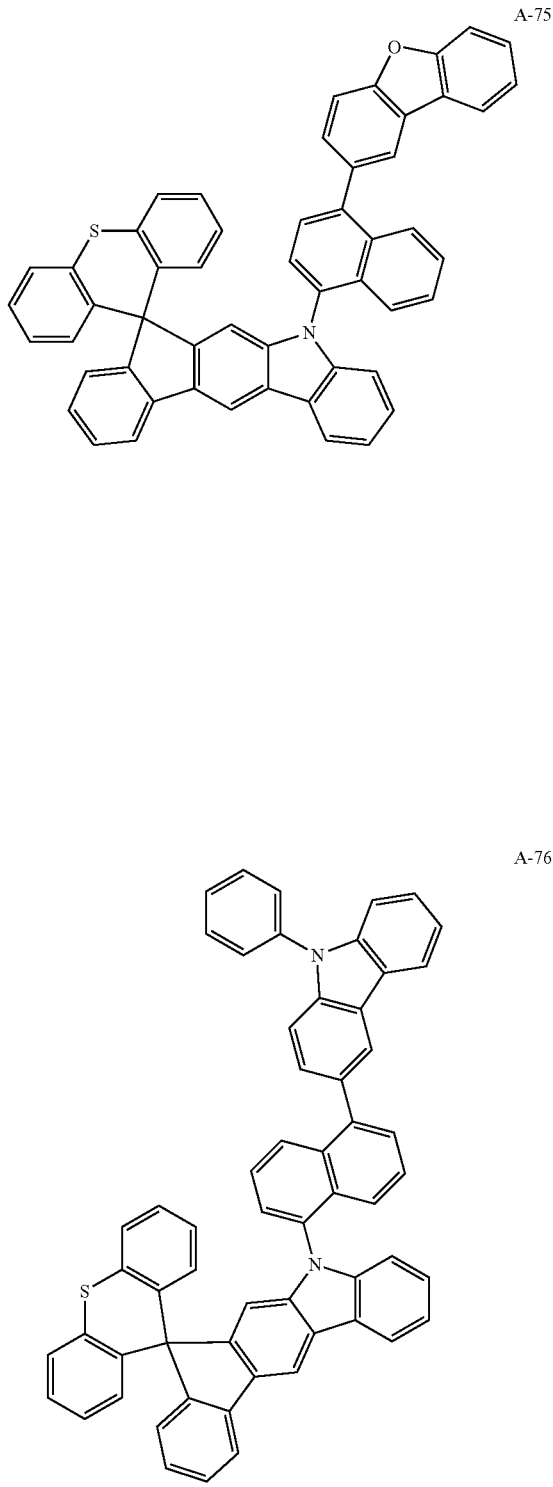

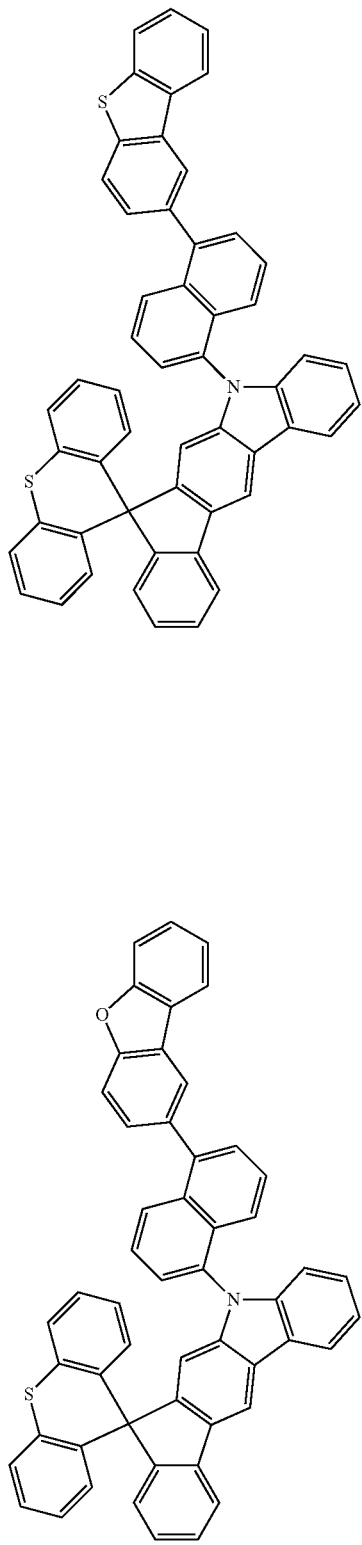
A-77
A-78
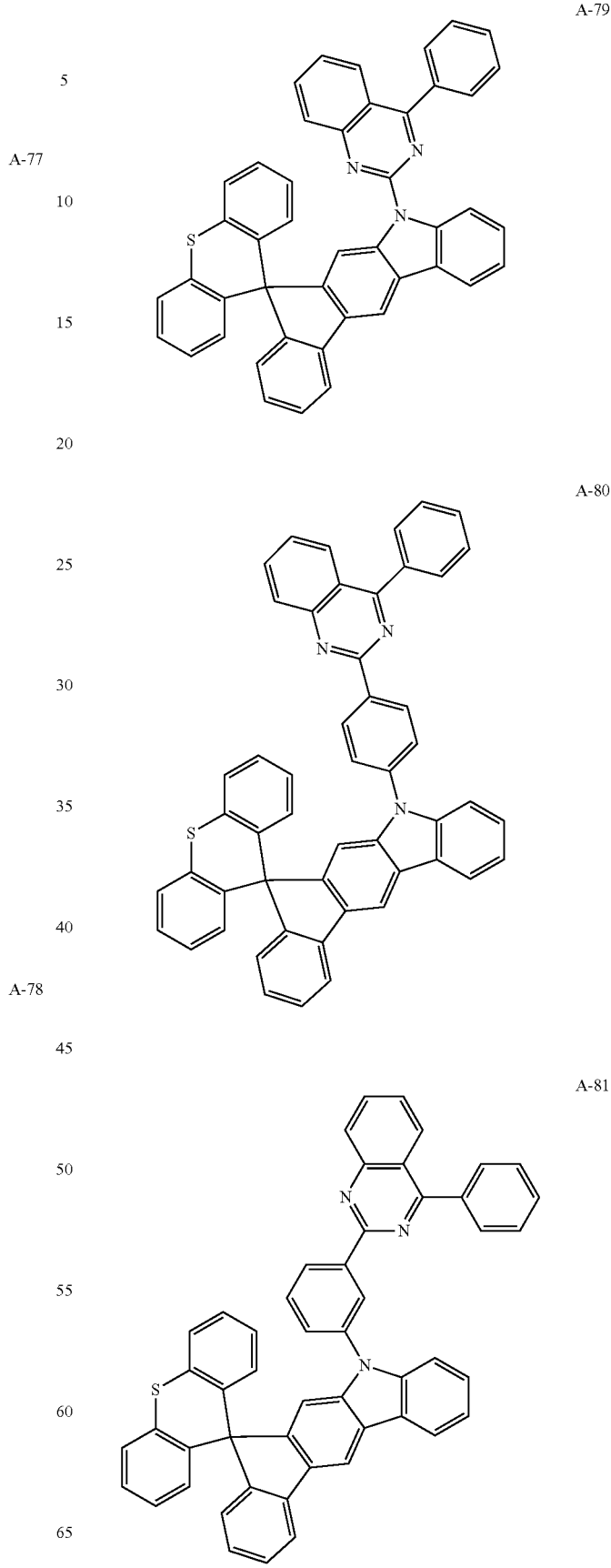
A-79
A-80
A-81

A-82
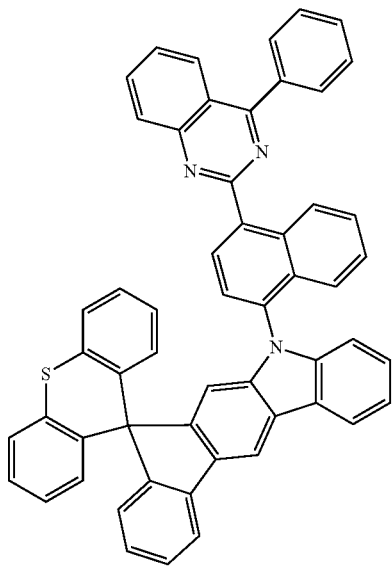
A-83
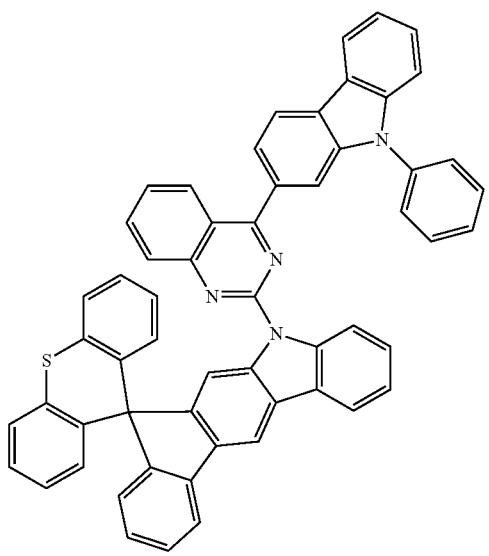
A-84
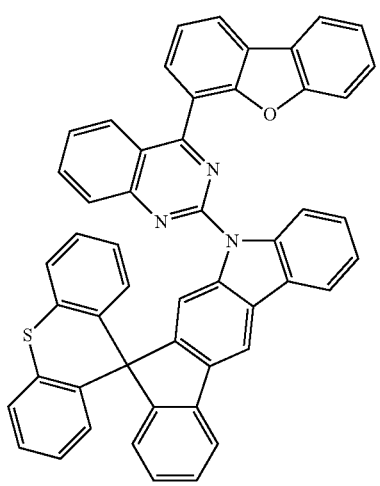
A-85
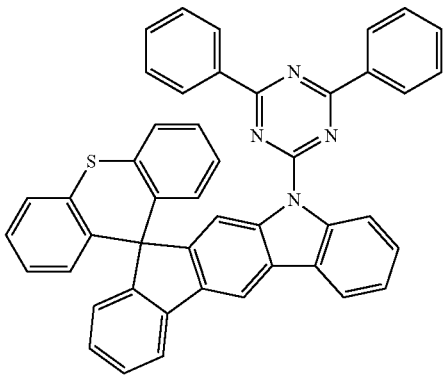
A-86
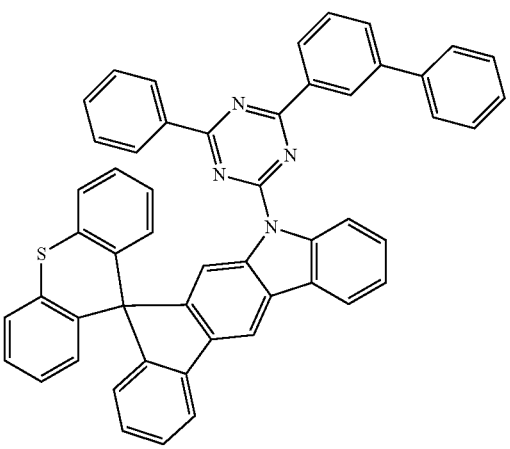
A-87
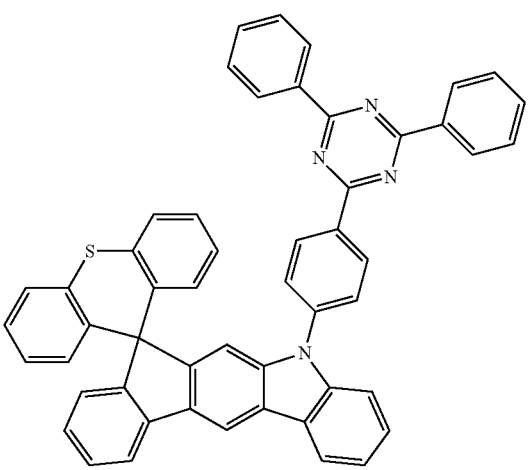

A-88
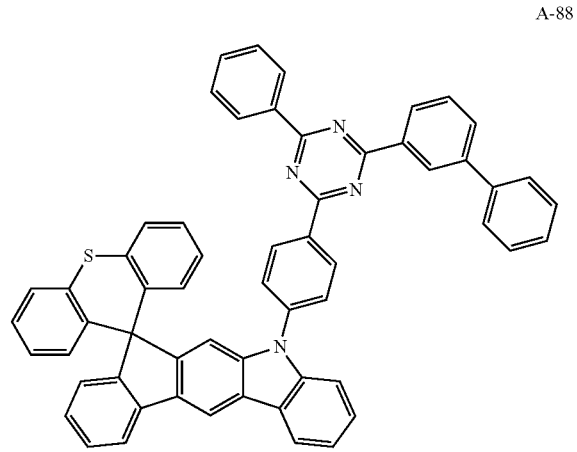
A-91
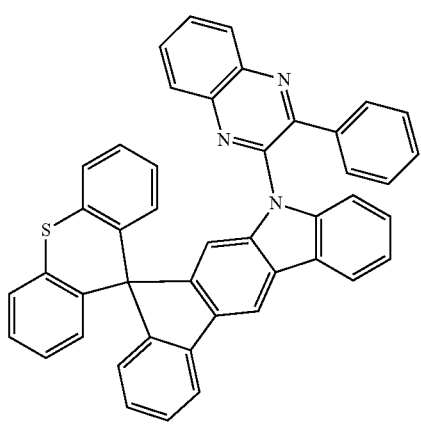
A-89
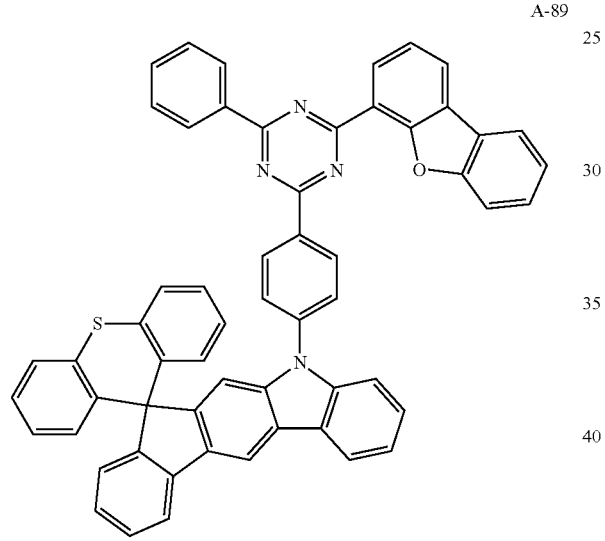
A-92
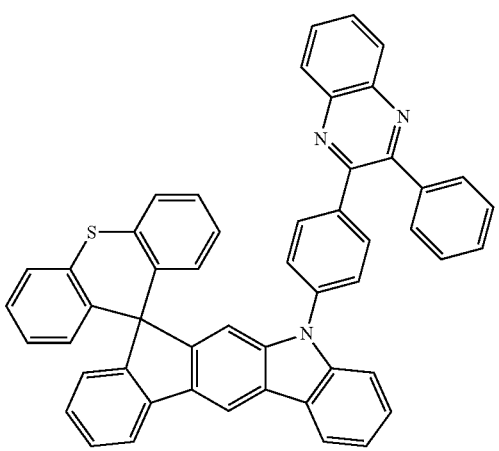
A-90
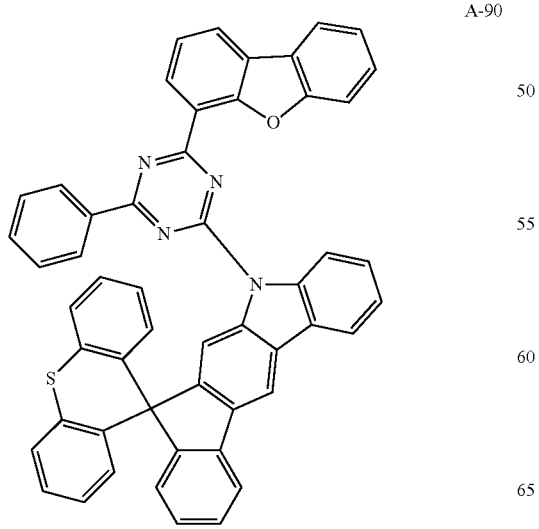
A-93
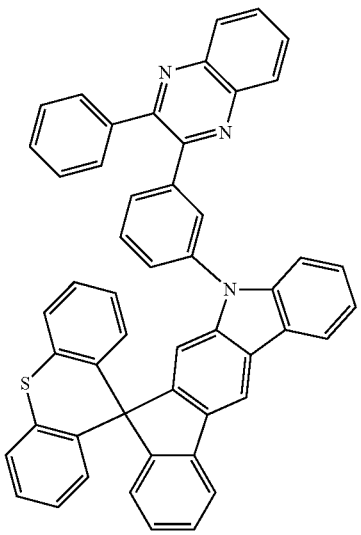

A-94
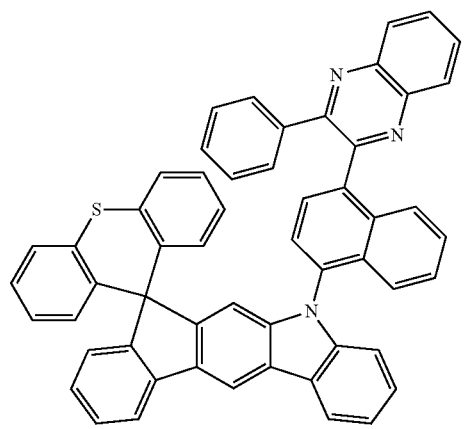
A-95
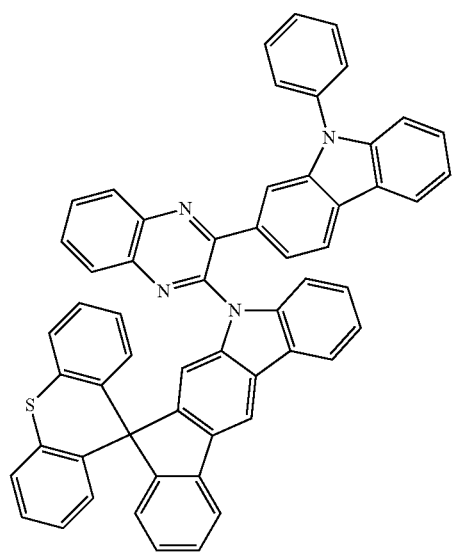
A-96
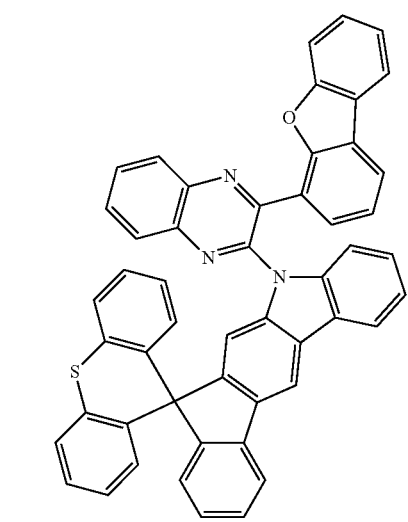
A-97
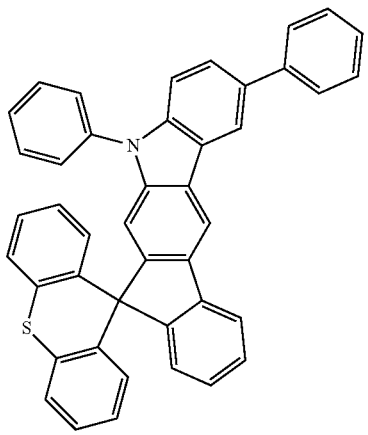
A-98
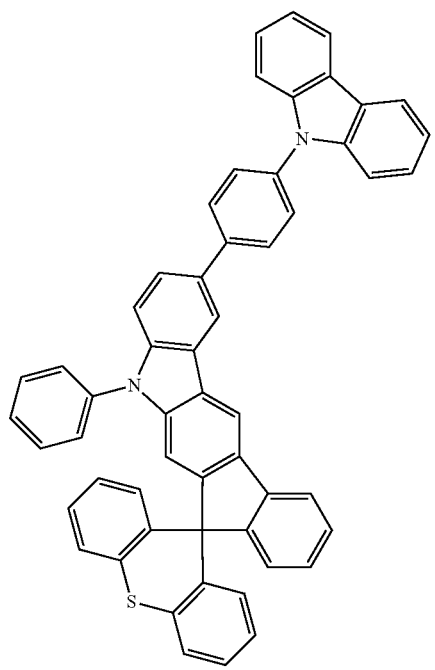
A-99
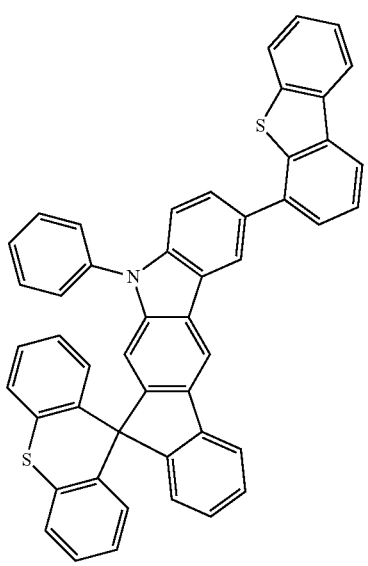

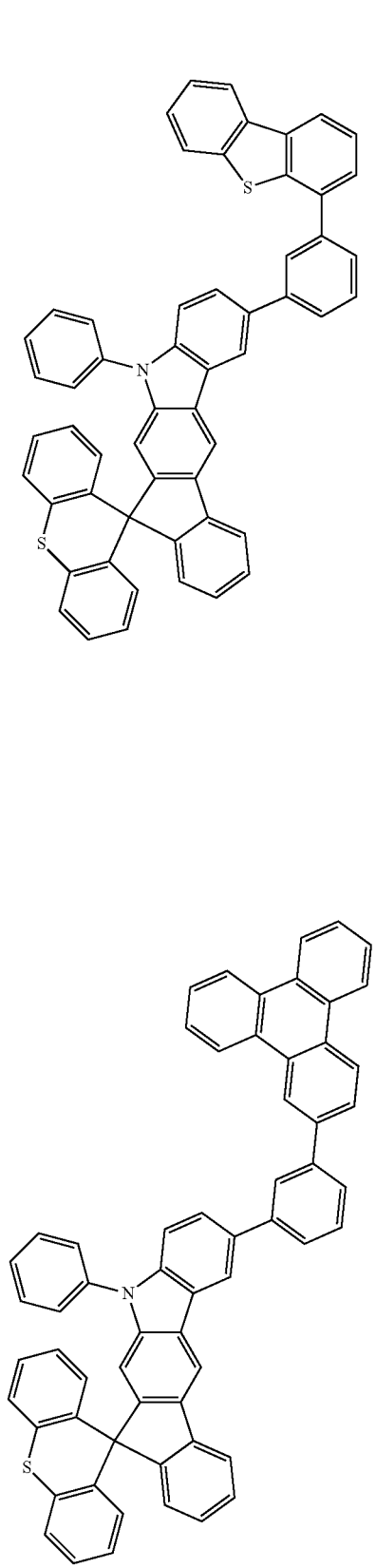
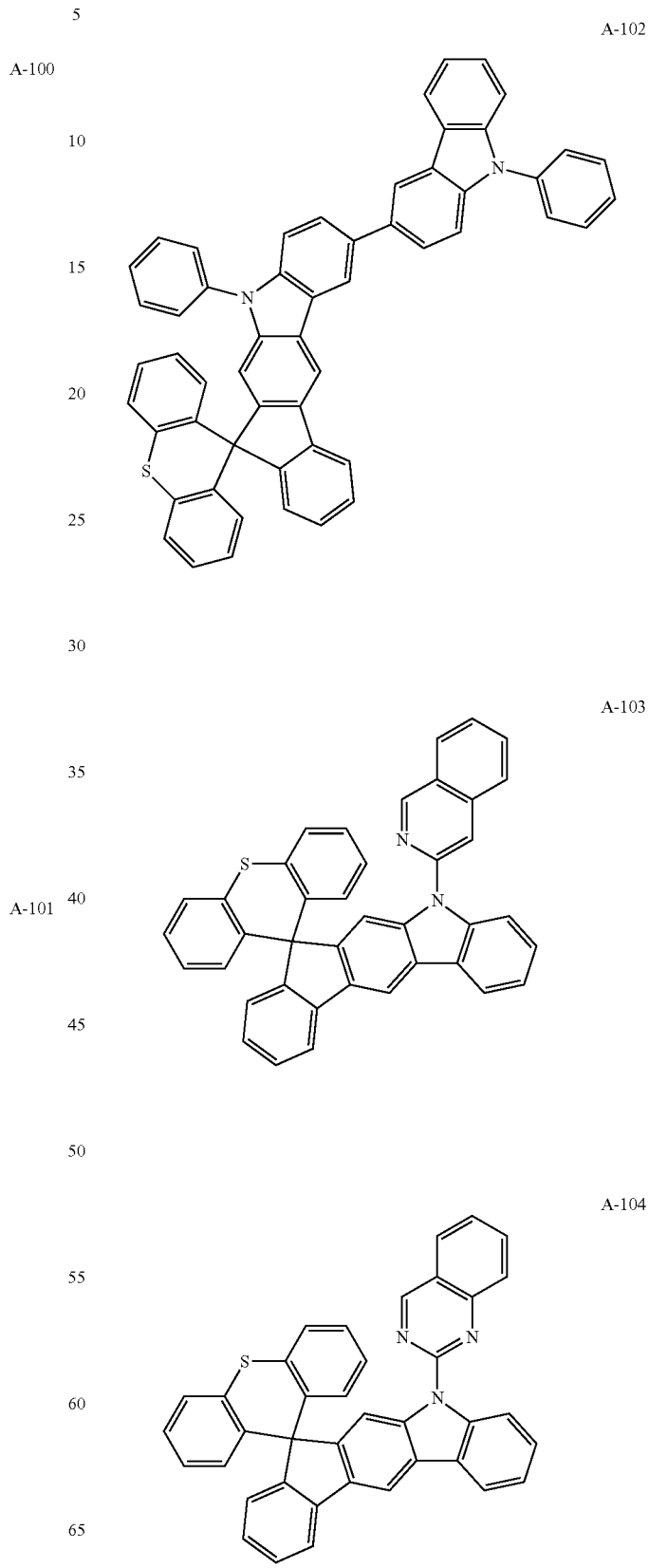

A-105
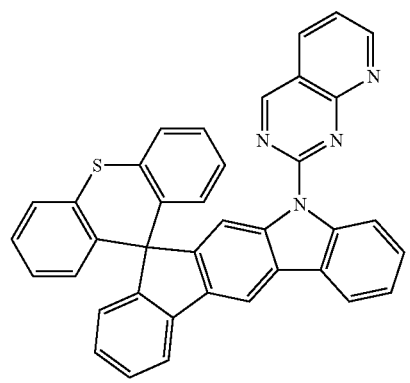
A-106
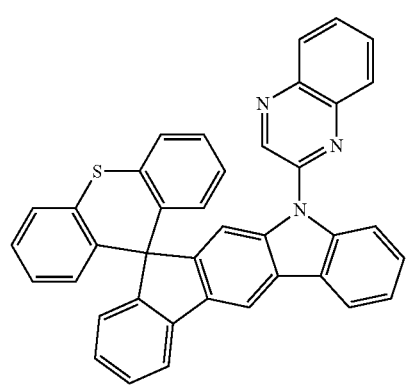
A-107
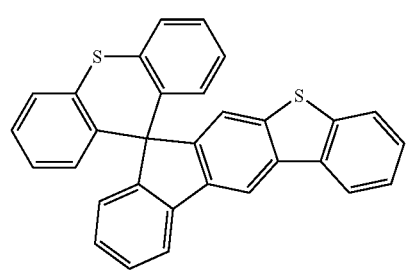
A-108
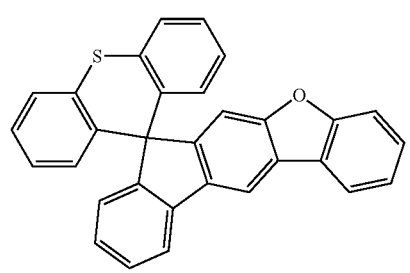
A-109
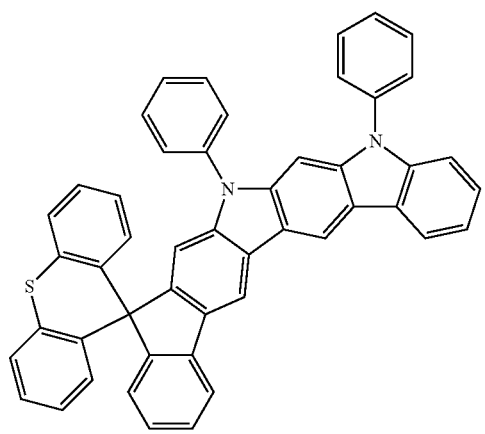
A-110
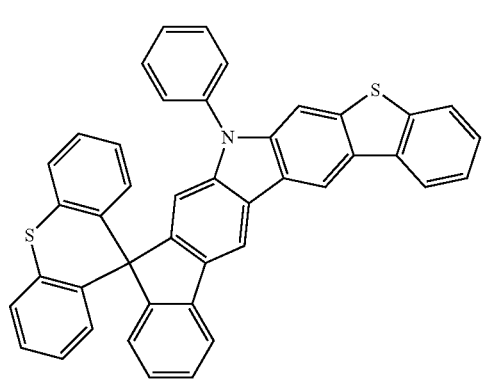
A-111
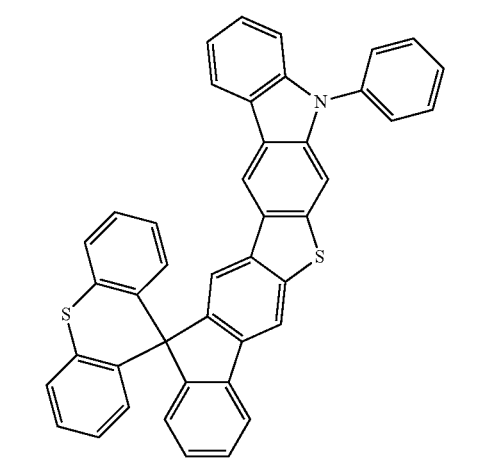
A-112
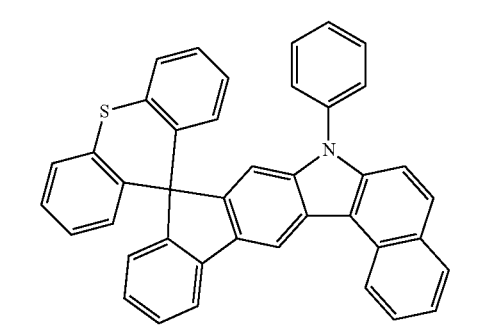

A-113
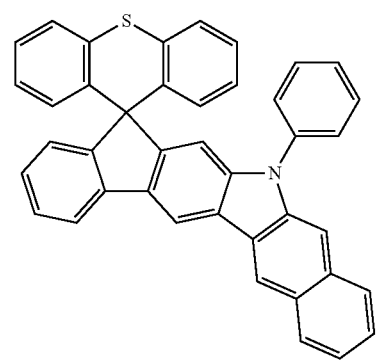
A-114
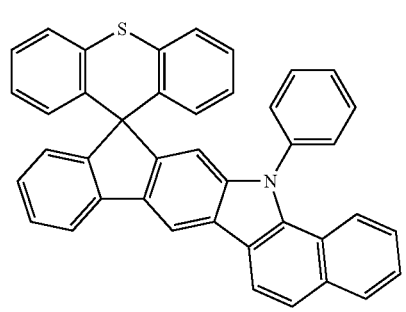
A-115
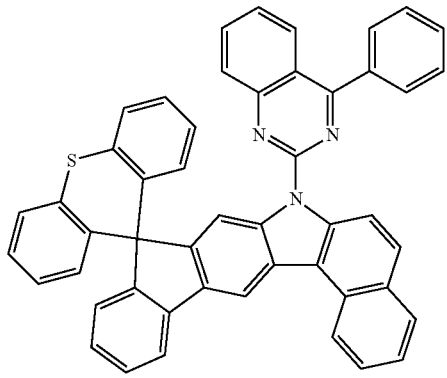
A-116
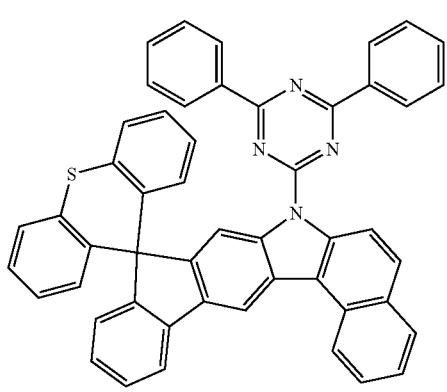
A-117
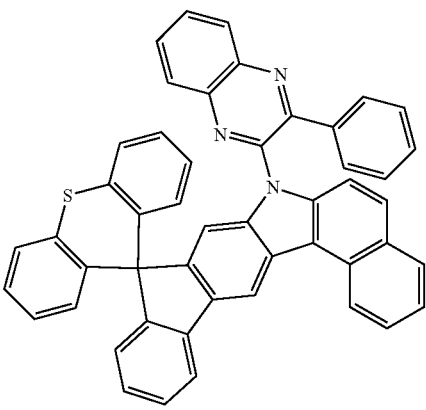
A-118
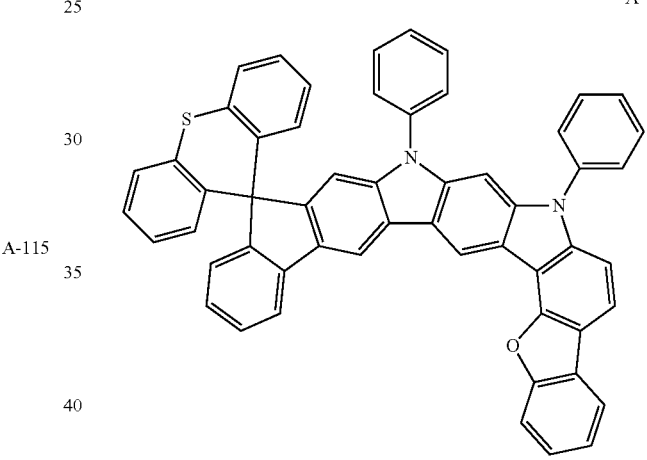
A-119
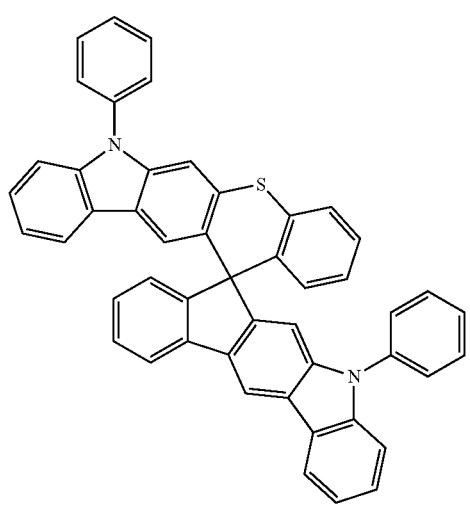

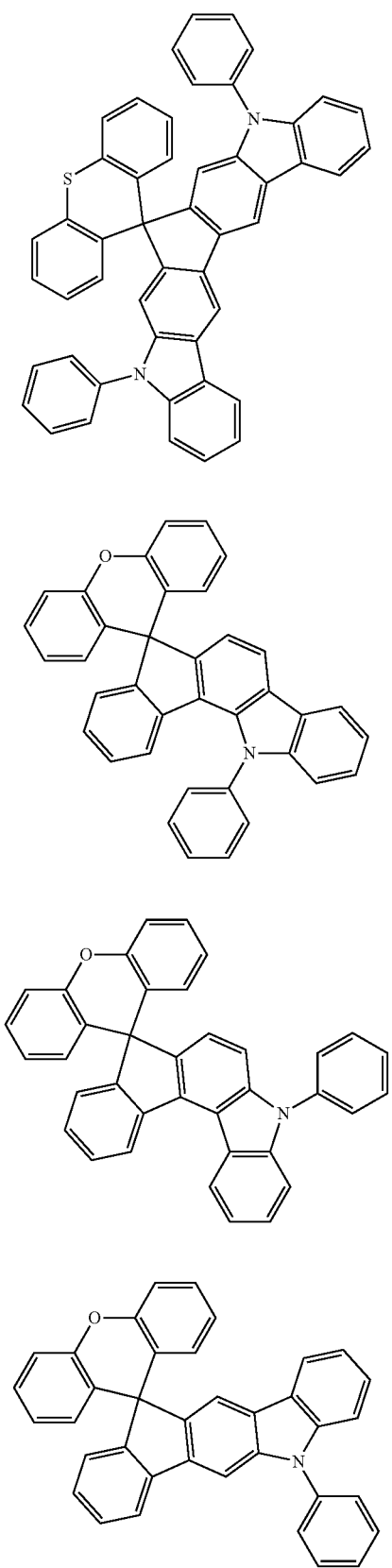
A-120
A-121
A-122
A-123
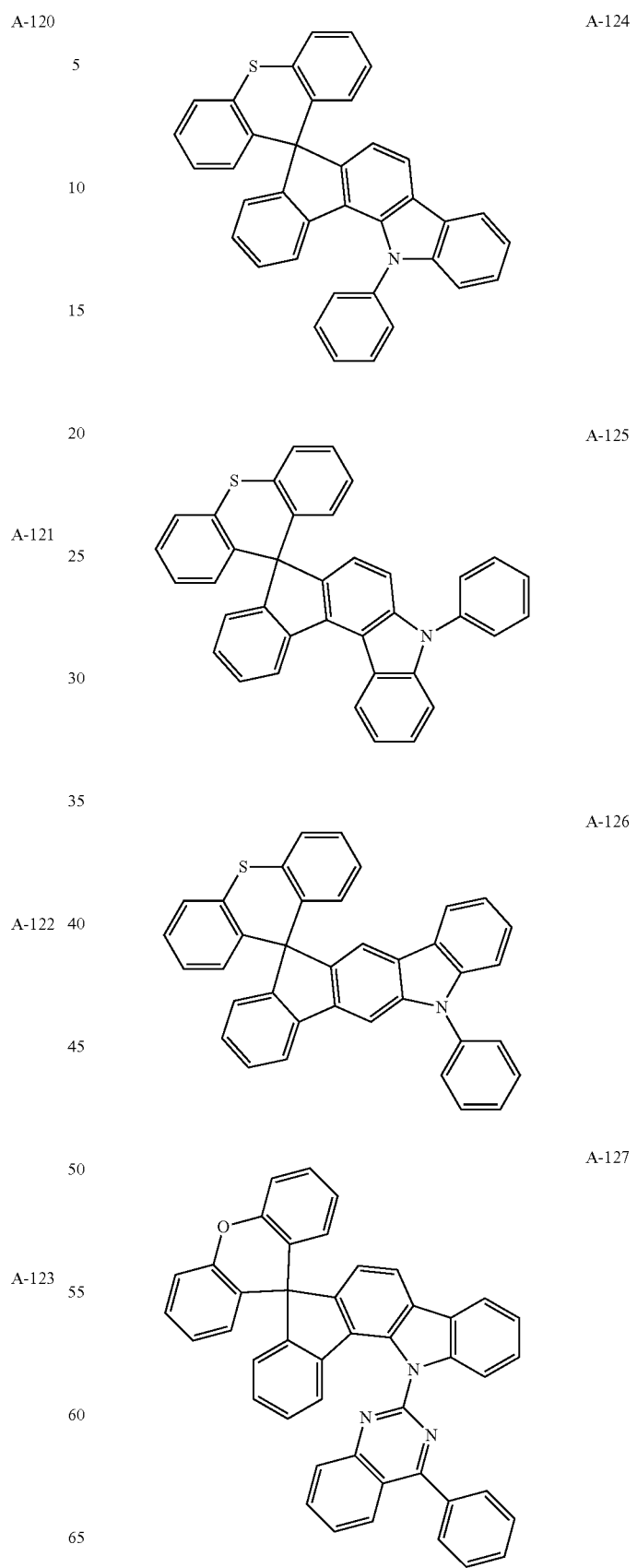
A-124
A-125
A-126
A-127

A-128
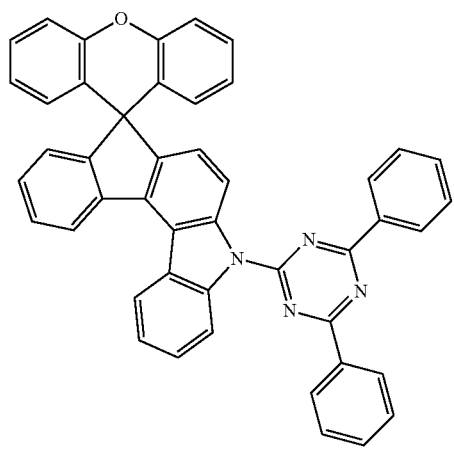
A-129
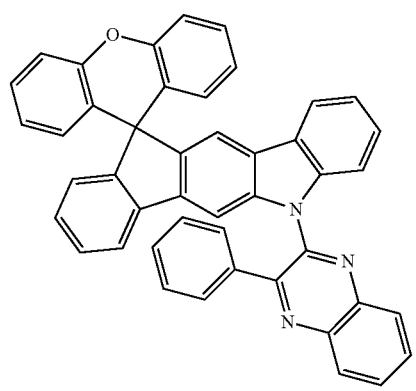
A-130
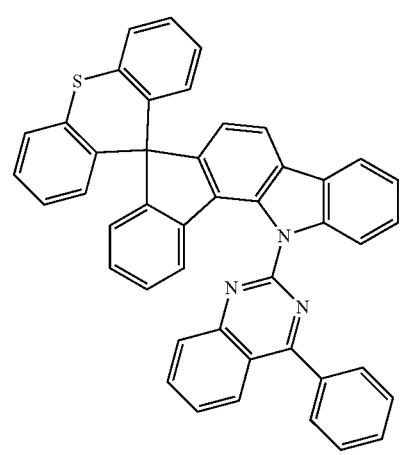
A-131
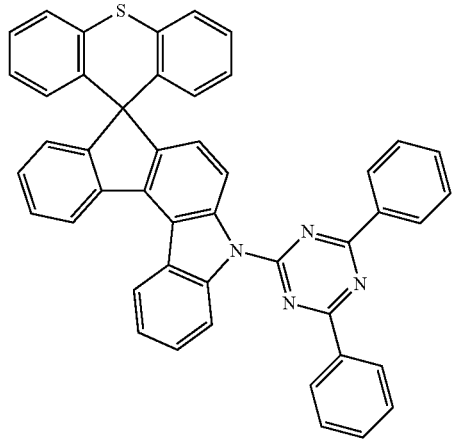
A-132
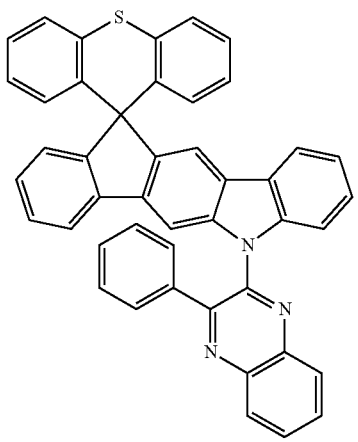
A-133
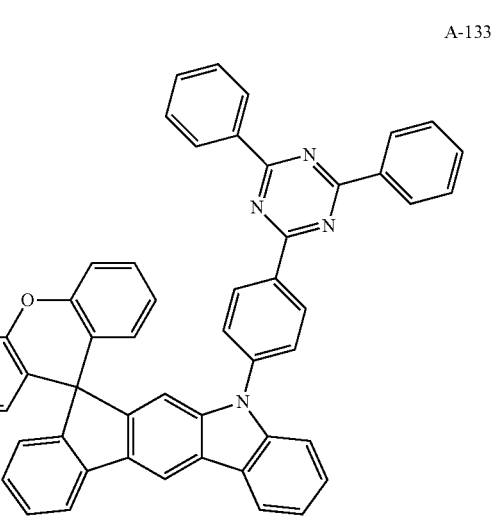

A-134
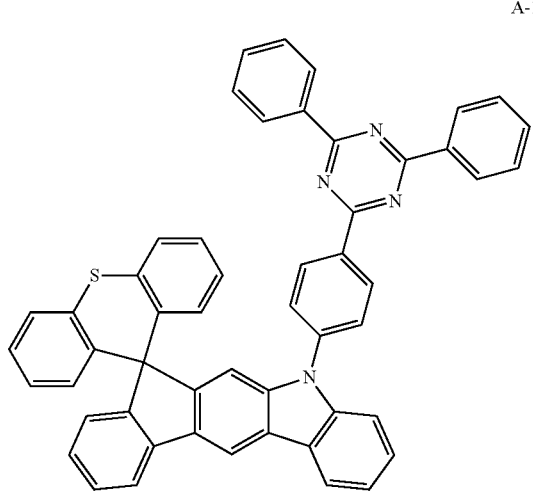
A-135
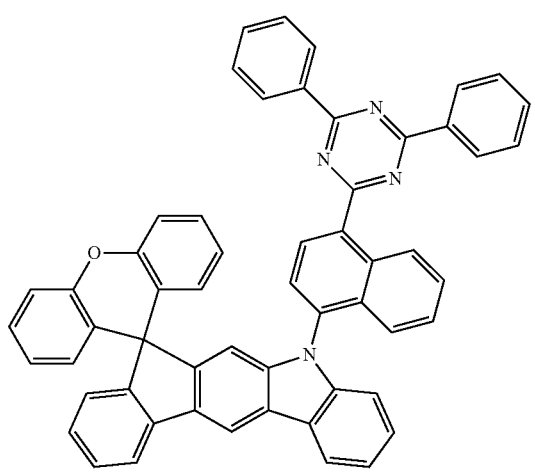
A-136
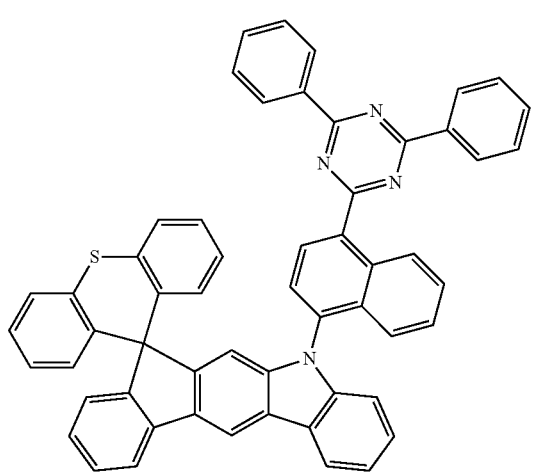
A-137
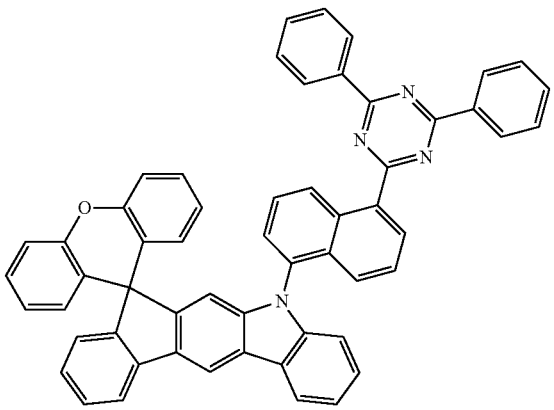
A-138
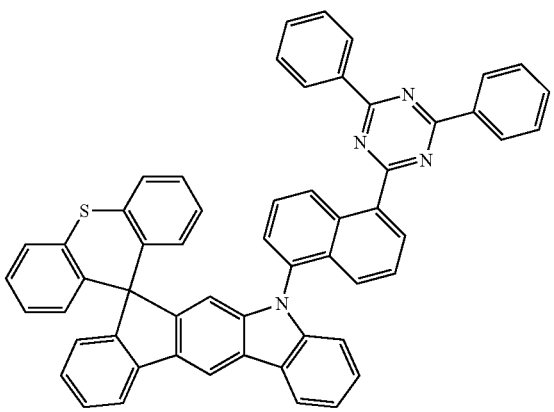
A-139
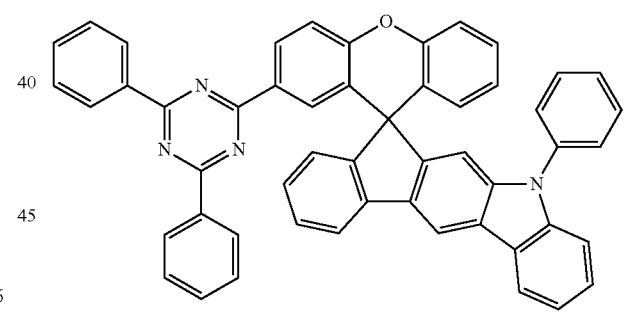
A-140
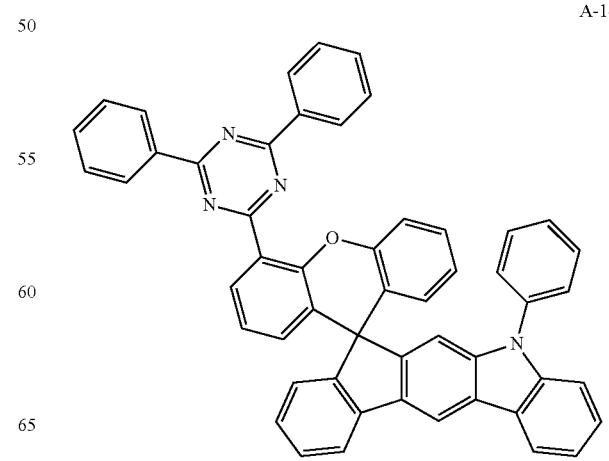

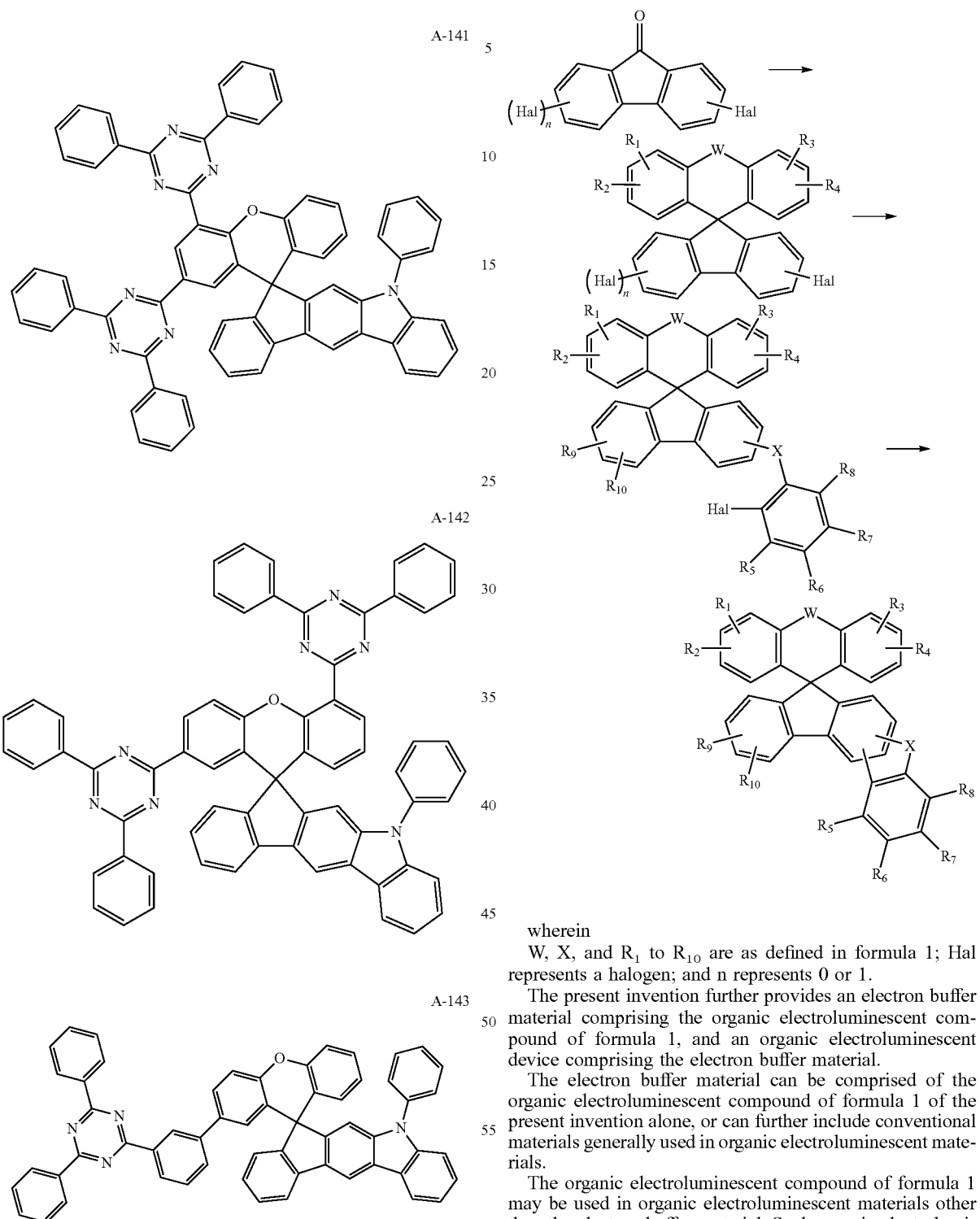

wherein

W, X, and $R_1$ to $R_{10}$ are as defined in formula 1; Hal represents a halogen; and n represents 0 or 1.

The present invention further provides an electron buffer material comprising the organic electroluminescent compound of formula 1, and an organic electroluminescent device comprising the electron buffer material.

The electron buffer material can be comprised of the organic electroluminescent compound of formula 1 of the present invention alone, or can further include conventional materials generally used in organic electroluminescent materials.

The organic electroluminescent compound of formula 1 may be used in organic electroluminescent materials other than the electron buffer material. Such organic electroluminescent materials may be preferably a host material, and, more preferably, a phosphorescent host material. If the organic electroluminescent material is used as a host material, it may further include a second host material as described below, in addition to the compound of formula 1.

The organic electroluminescent compound according to the present invention can be prepared by known methods to one skilled in the art, and can be prepared, for example, according to the following reaction scheme 1:

The organic electroluminescent device according to the present invention may comprise a first electrode, a second electrode, and at least one organic layer between the first and second electrodes, wherein the organic layer comprises at least one compound of formula 1.

One of the first electrode and the second electrode can be an anode and the other can be a cathode. The organic layer may comprise a light-emitting layer, and may further comprise at least one layer selected from the group consisting of a hole injection layer, a hole transport layer, an electron transport layer, an electron injection layer, an interlayer, a hole blocking layer, an electron blocking layer, and an electron buffer layer.

The compound of formula 1 of the present invention can be included in the light-emitting layer. If included in the light-emitting layer, the compound of formula 1 of the present invention can be contained as a host material, preferably, a phosphorescent host material. Preferably, the light-emitting layer may further comprise at least one dopant, and further comprise compounds other than the compound of formula 1 of the present invention as a second host material, if necessary. A first host material (the compound of formula 1) and the second host material may be present in the range of 1:99 to 99:1 in a weight ratio.

The second host material can be any of known phosphorescent host materials and preferably, is selected from the group consisting of the compounds of the following formulae 2 to 6 in view of luminous efficiency:

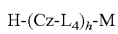  (2)

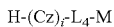  (3)

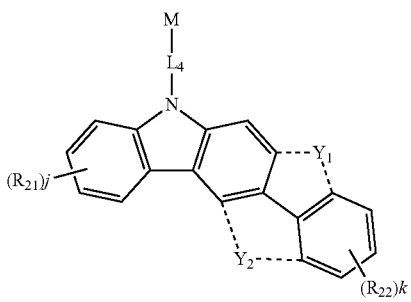  (4)

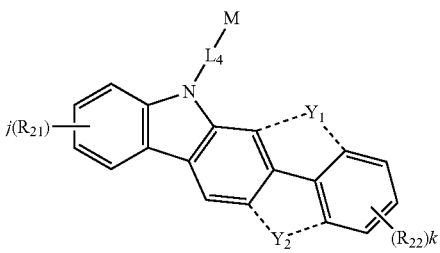  (5)

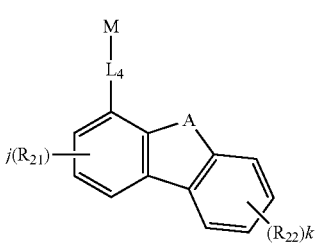  (6)

wherein
Cz represents the following structure:

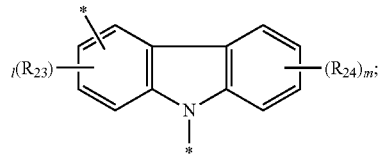

A represents —O— or —S—;

$R_{21}$ to $R_{24}$ each independently represent hydrogen, deuterium, a halogen, a substituted or unsubstituted (C1-C30) alkyl group, a substituted or unsubstituted (C6-C30)aryl group, a substituted or unsubstituted 5- or 30-membered heteroaryl group, or —$SiR_{25}R_{26}R_{27}$;

$R_{25}$ to $R_{27}$ each independently represent a substituted or unsubstituted (C1-C30)alkyl group, or a substituted or unsubstituted (C6-C30)aryl group;

$L_4$ represents a single bond, a substituted or unsubstituted (C6-C30)arylene group, or a substituted or unsubstituted 5- or 30-membered heteroarylene group;

M represents a substituted or unsubstituted (C6-C30)aryl group, or a substituted or unsubstituted 5- or 30-membered heteroaryl group;

$Y_1$ and $Y_2$ each independently represent —O—, —S—, —N($R_{31}$)—, or —C($R_{32}$)($R_{33}$)—; and $Y_1$ and $Y_2$ are not simultaneously present;

$R_{31}$ to $R_{33}$ each independently represent a substituted or unsubstituted (C1-C30)alkyl group, a substituted or unsubstituted (C6-C30)aryl group, or a substituted or unsubstituted 5- or 30-membered heteroaryl group; and $R_{32}$ and $R_{33}$ may be the same or different;

h and i each independently represent an integer of 1 to 3;

j, k, l, and m each independently represent an integer of 0 to 4;

where h, i, j, k, l, or m is an integer of 2 or more, each (Cz-$L_4$), each (Cz), each $R_{21}$, each $R_{22}$, each $R_{23}$, or each $R_{24}$ may be the same or different.

Specifically, the second host material preferably includes the following:

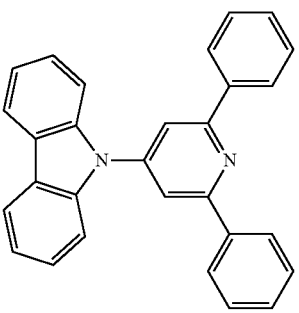

-continued
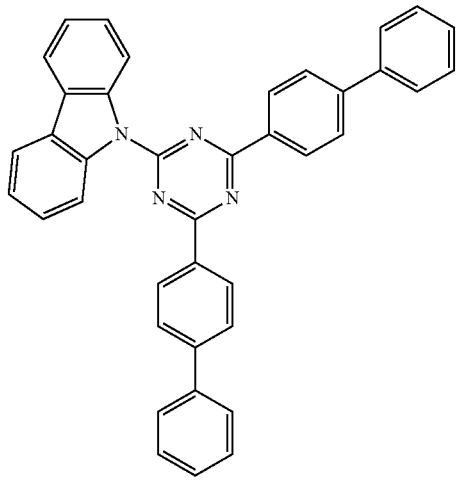
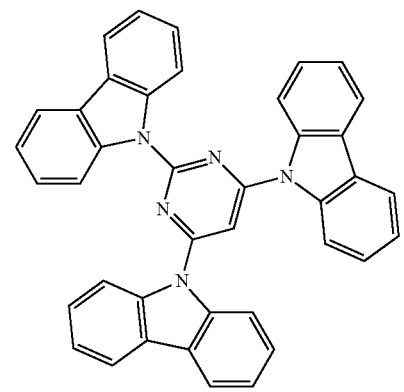
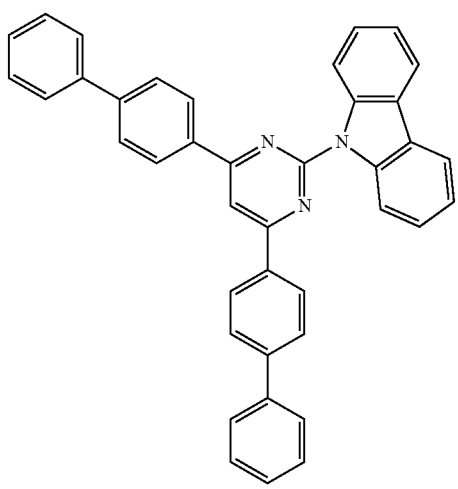
-continued
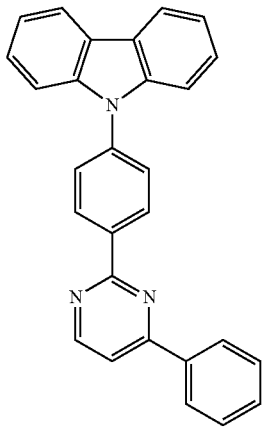
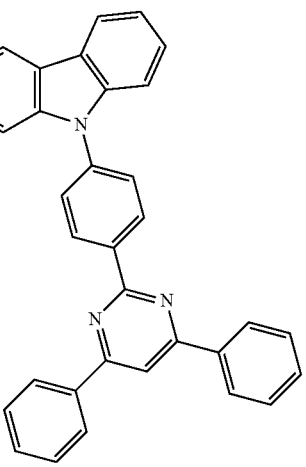
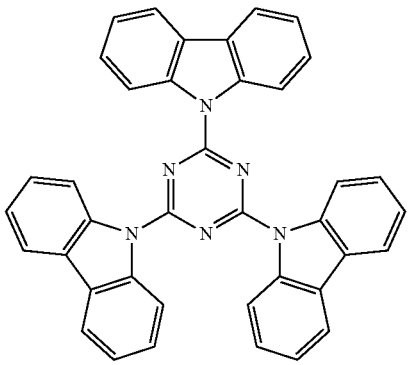

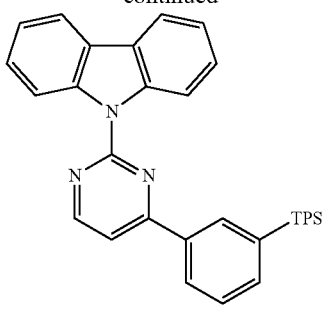
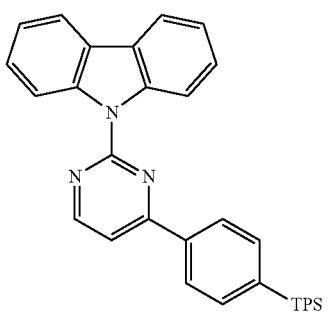
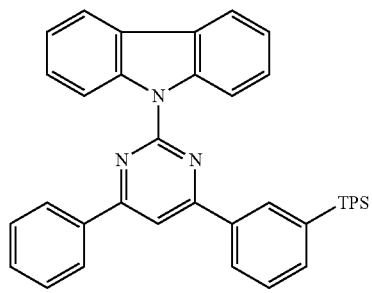
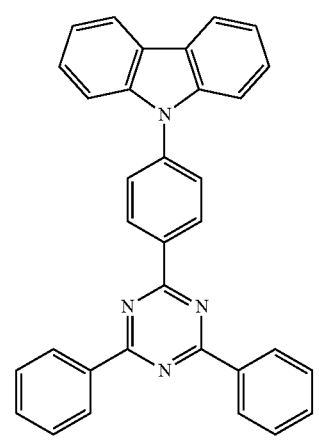
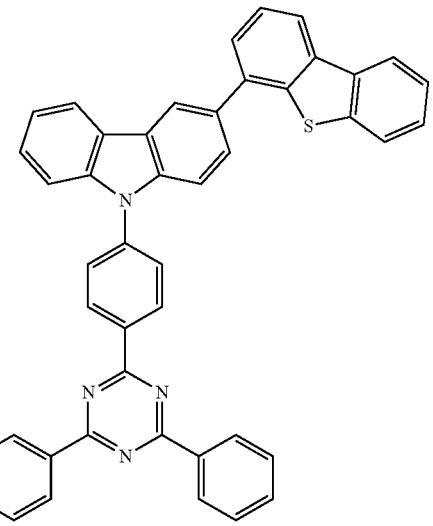
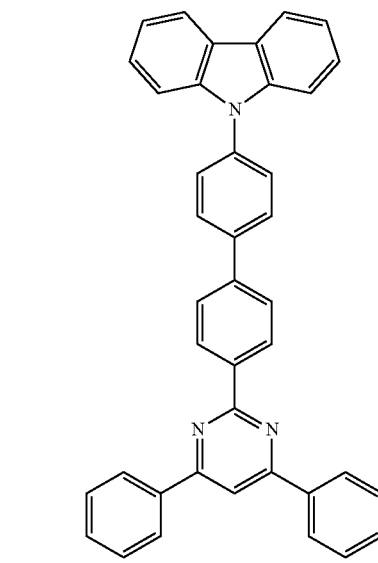
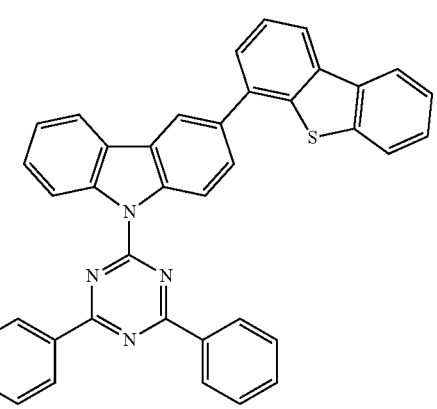

-continued
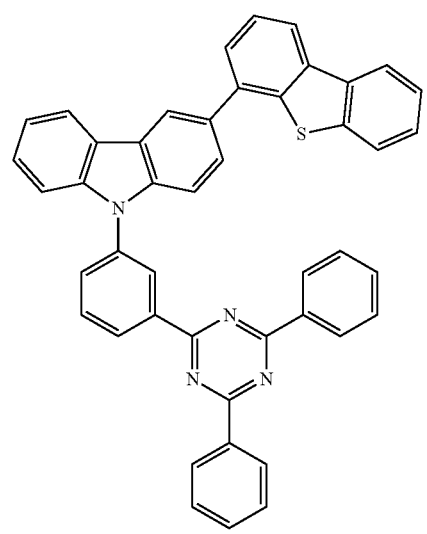
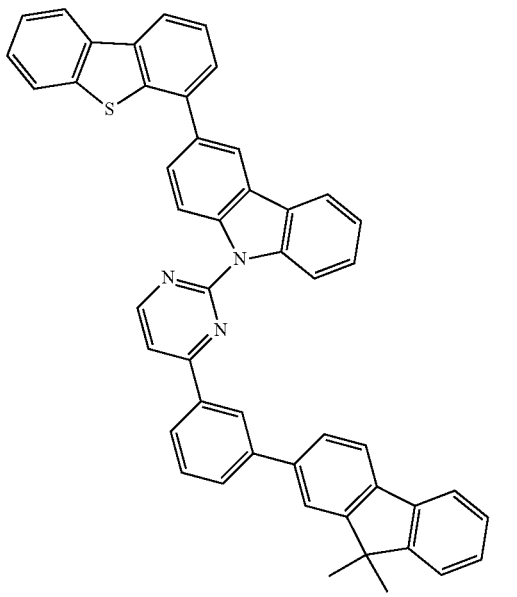
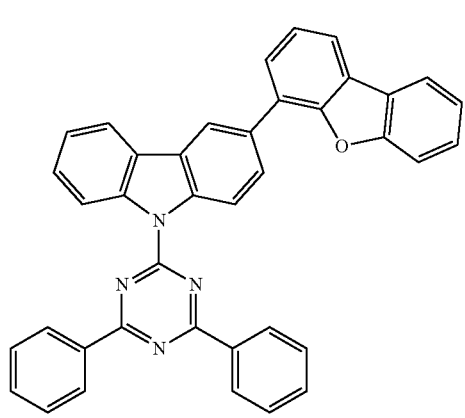
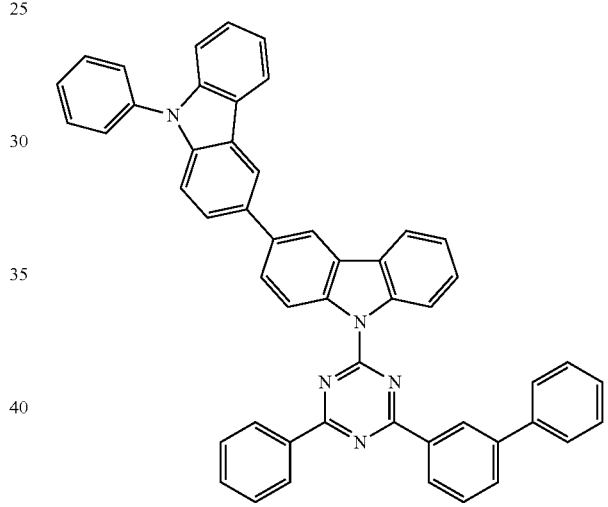
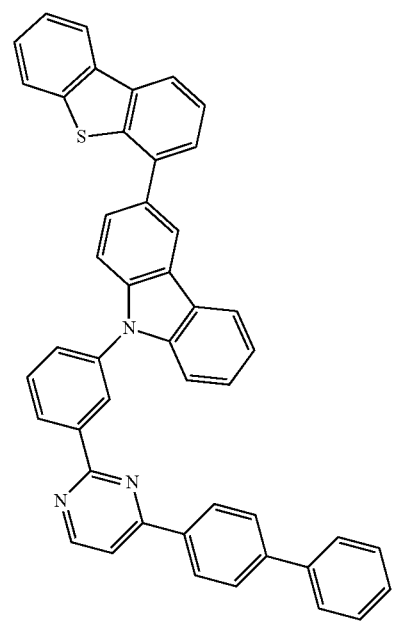
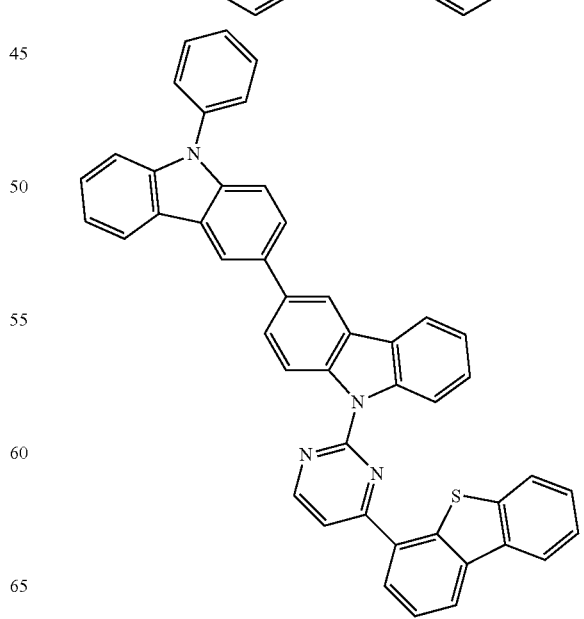

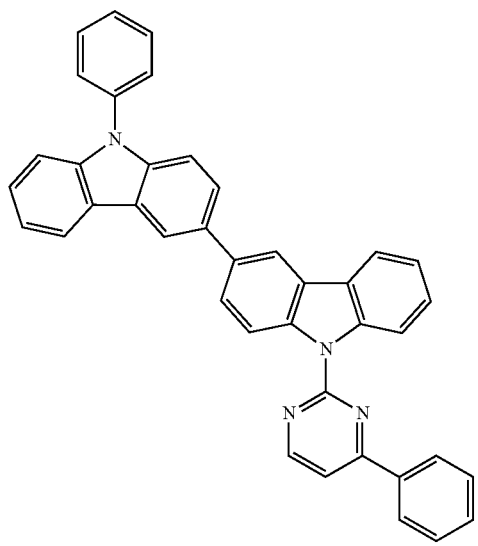
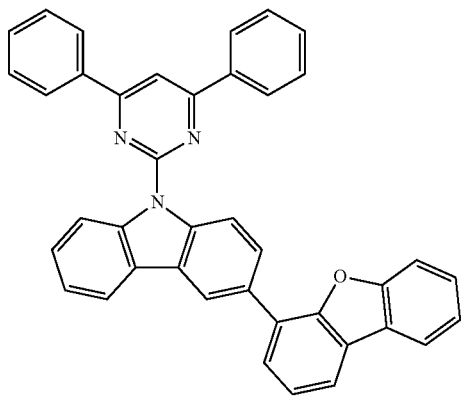
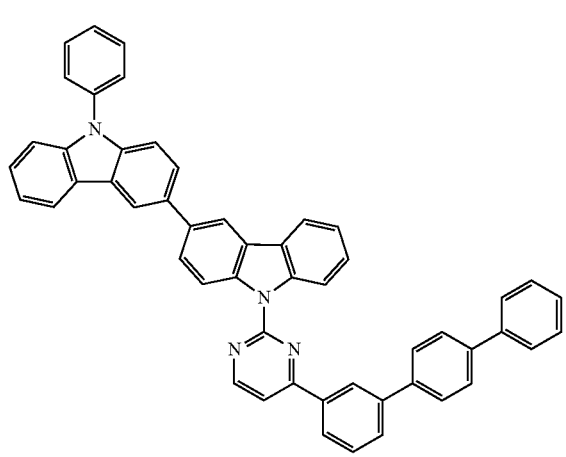
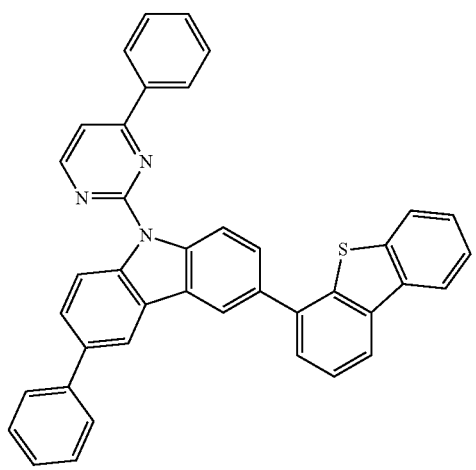
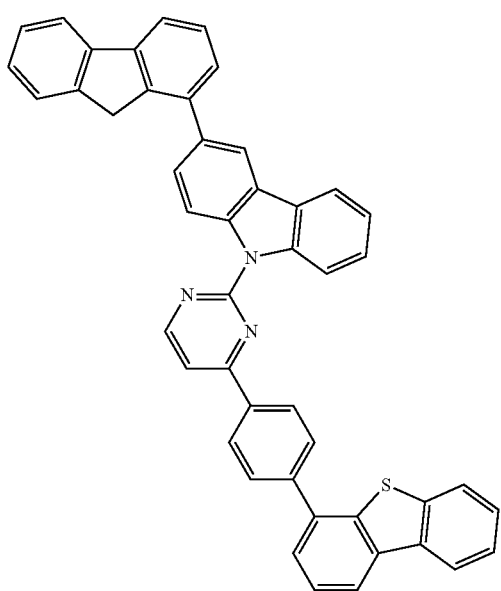
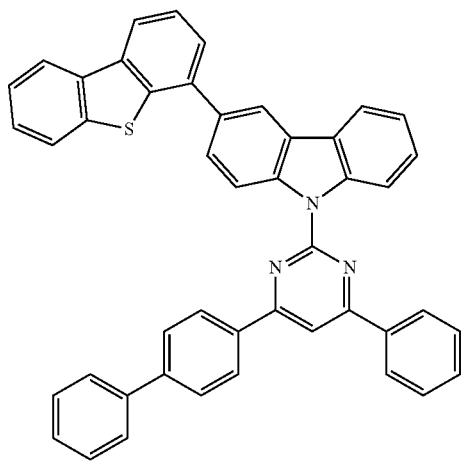

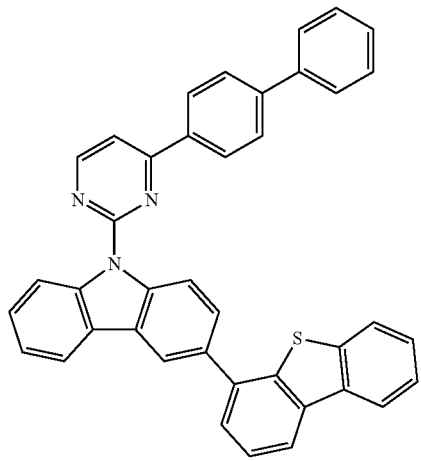
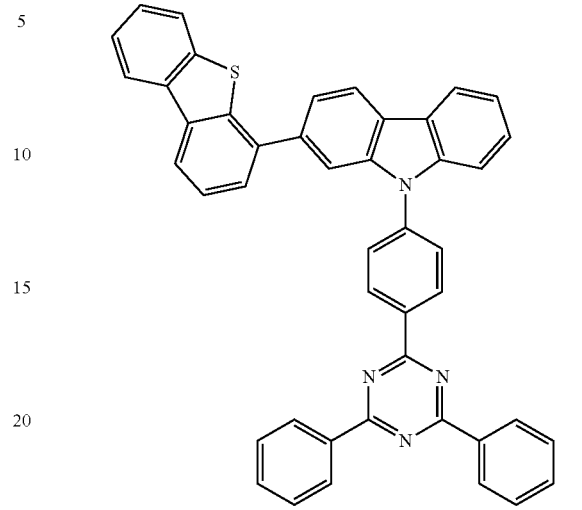
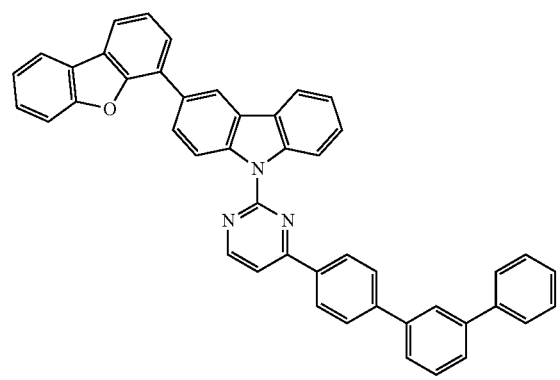
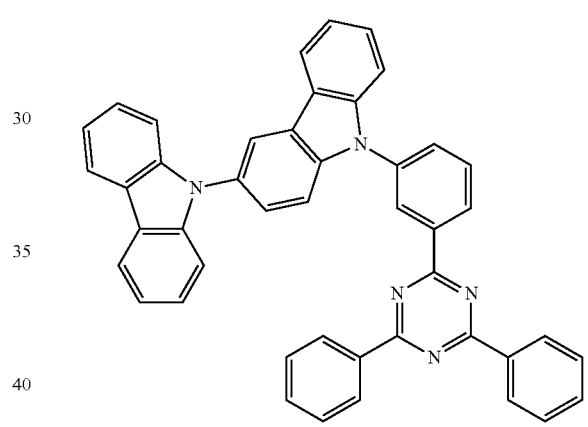
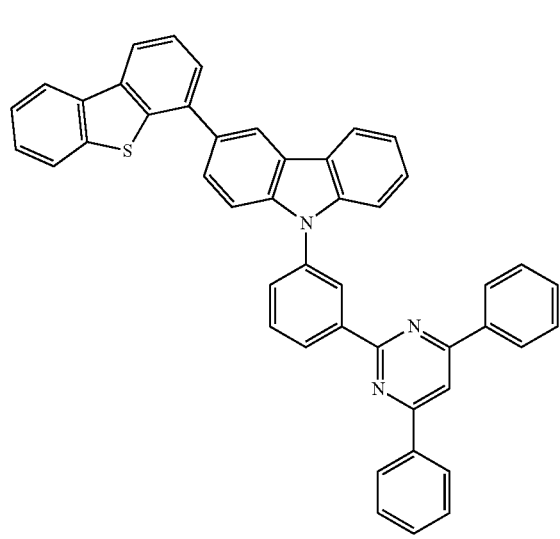
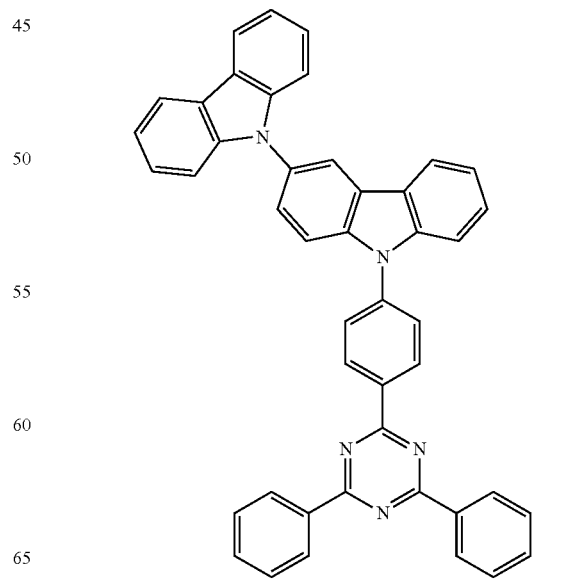

51
-continued
52
-continued
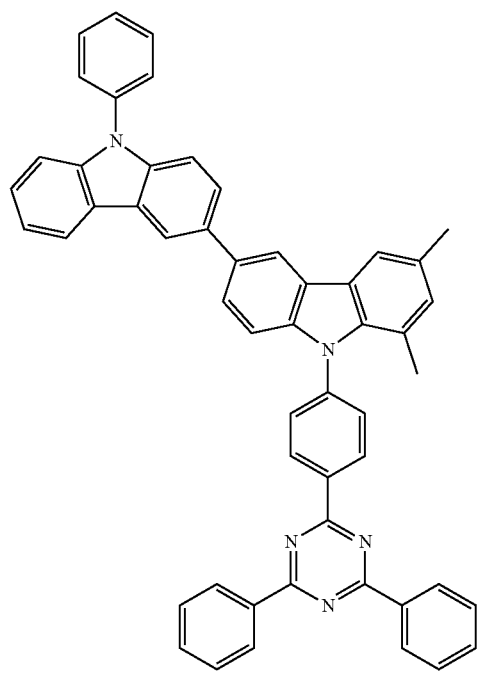
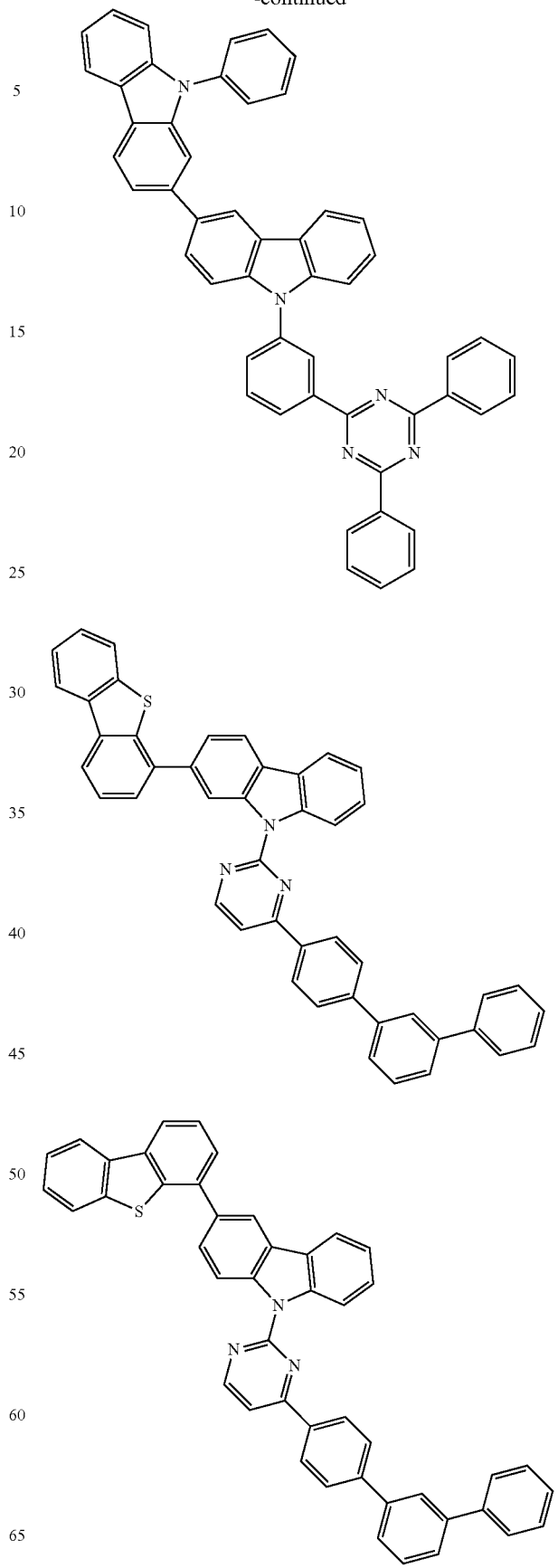

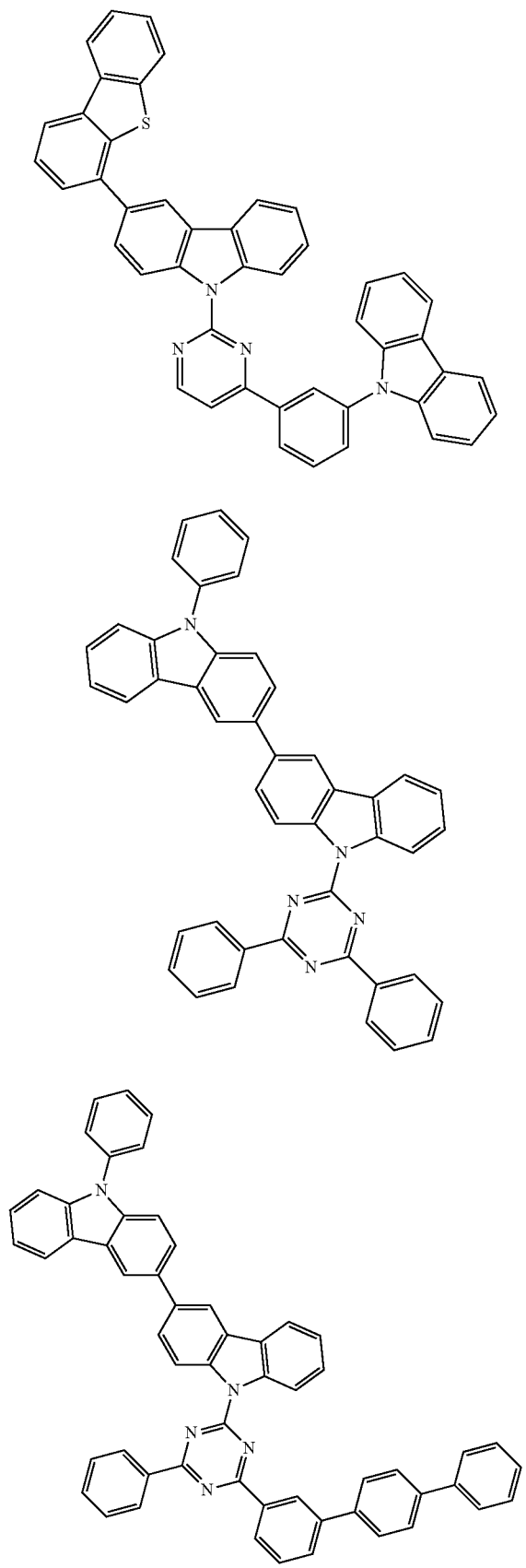
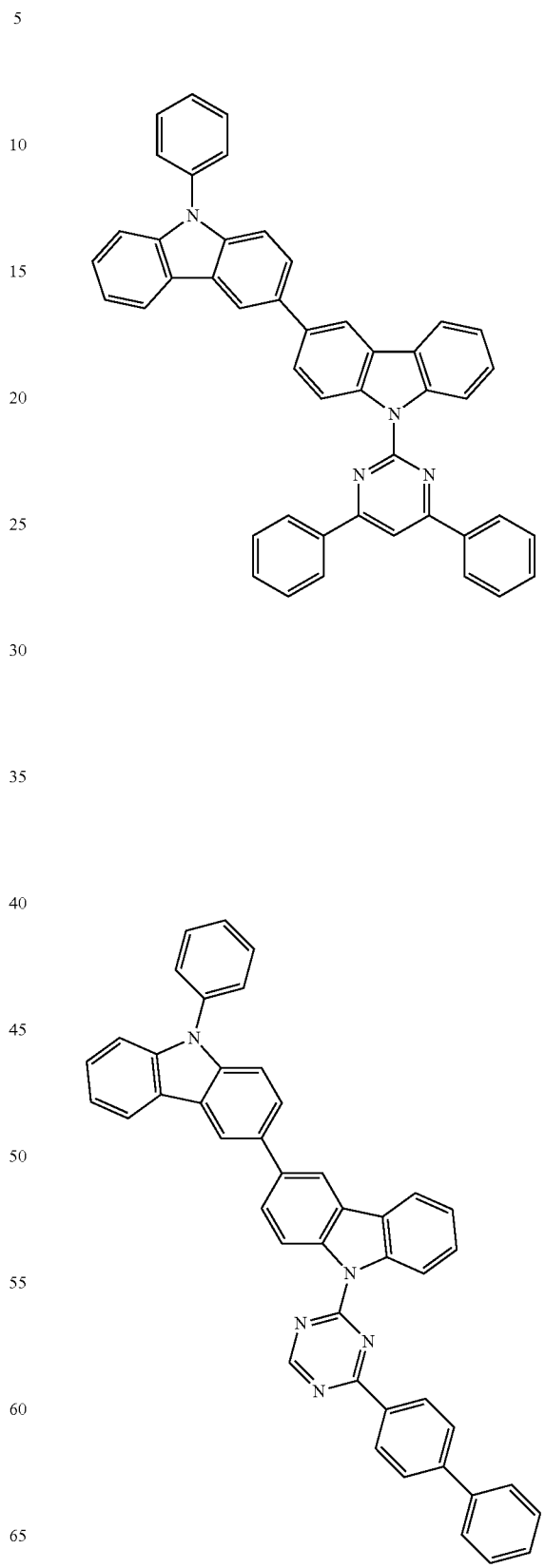

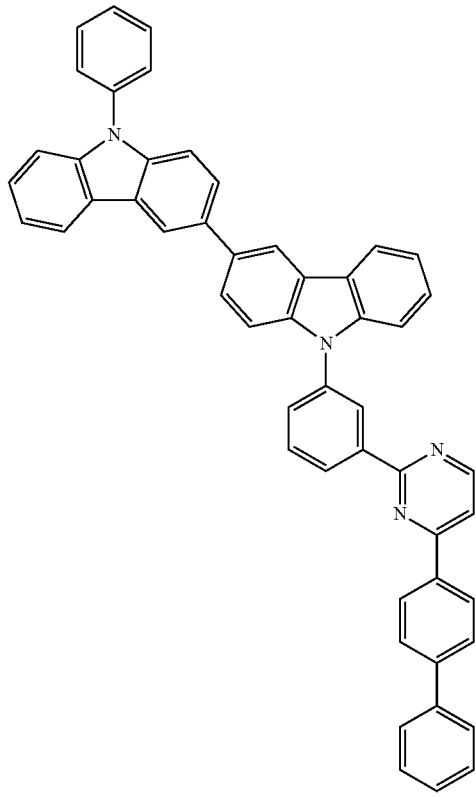
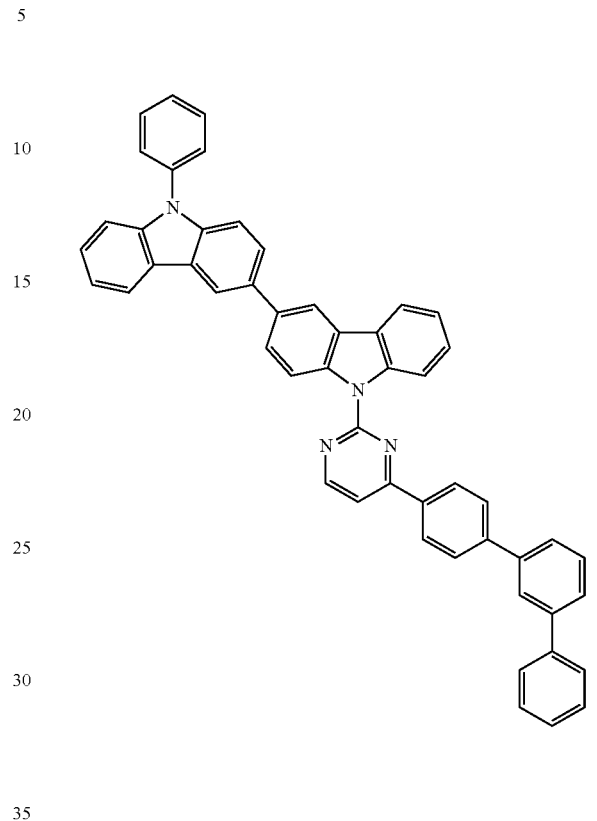
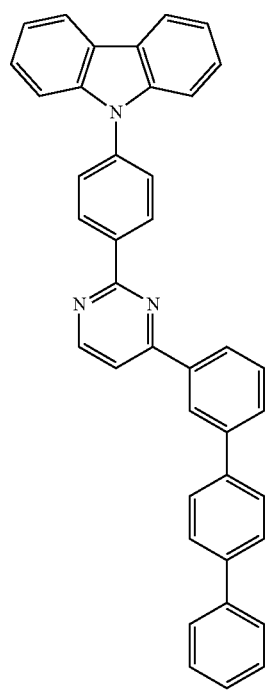
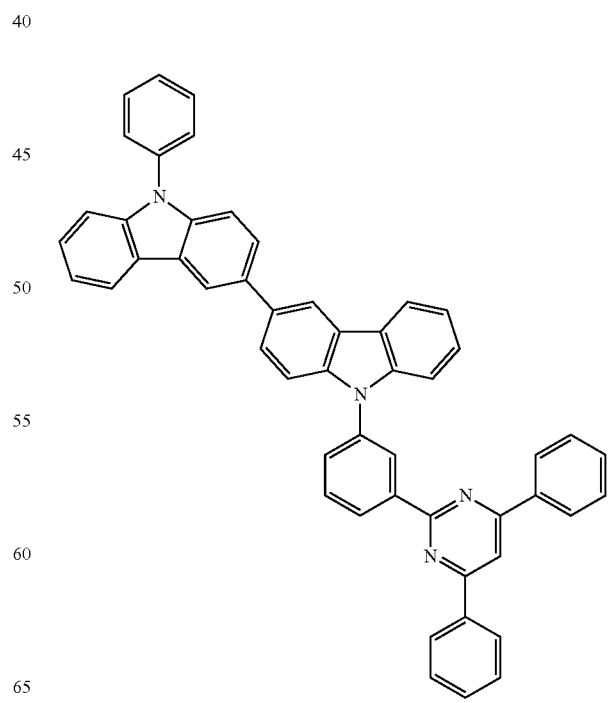

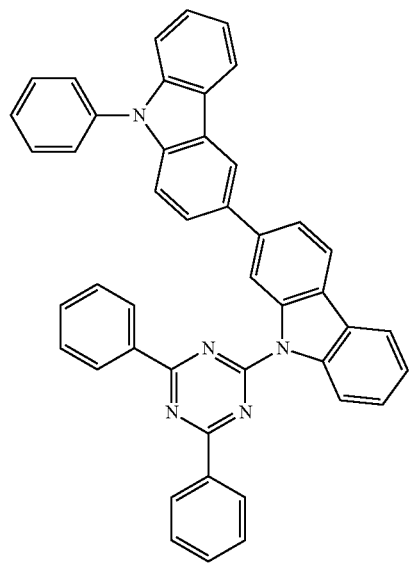
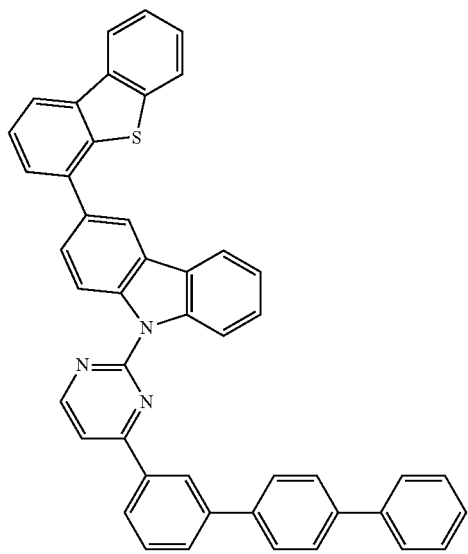
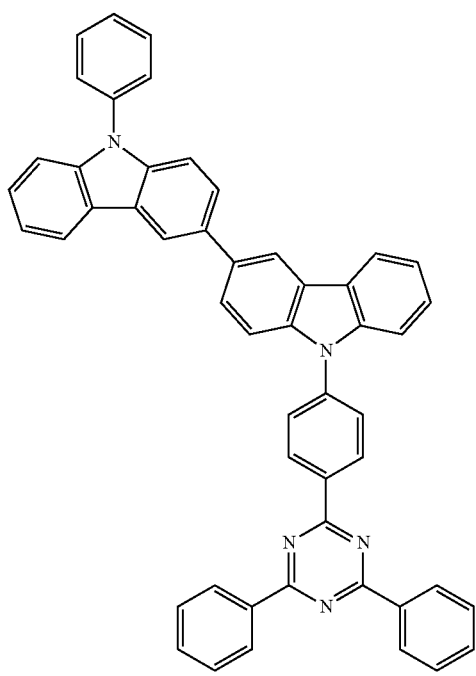
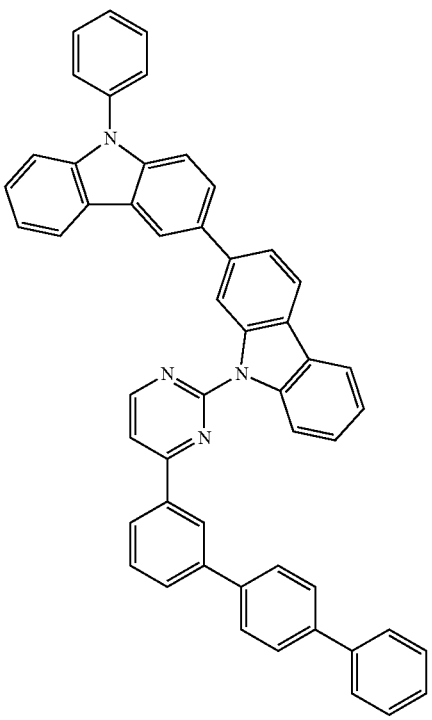

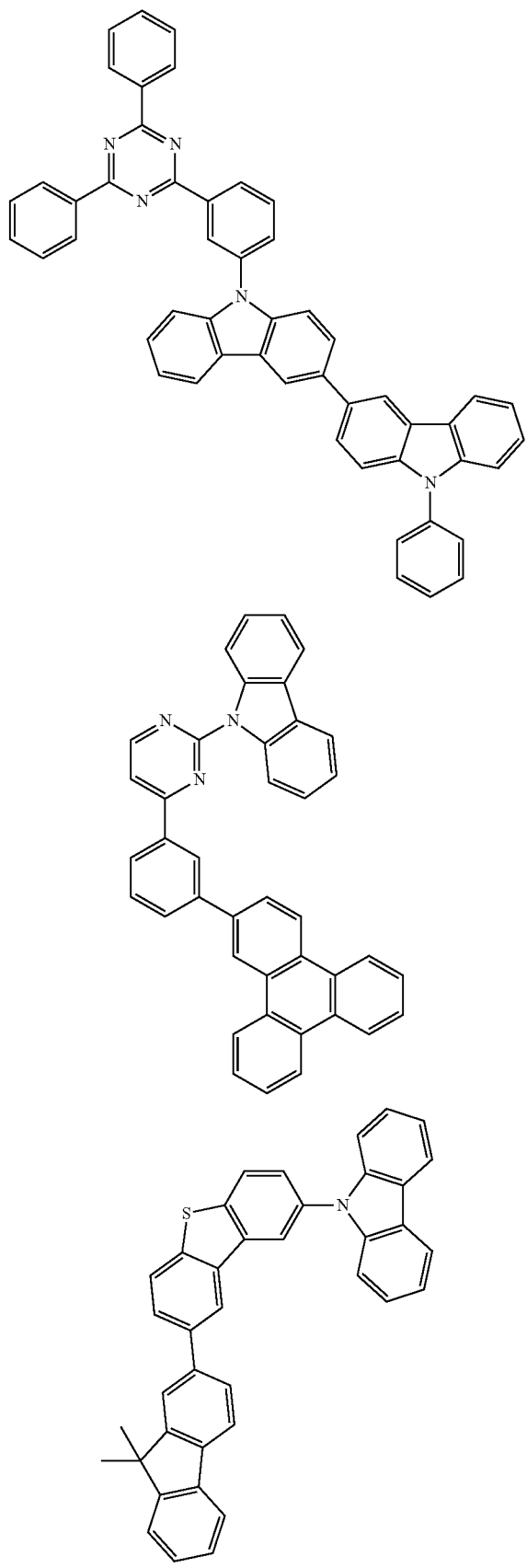
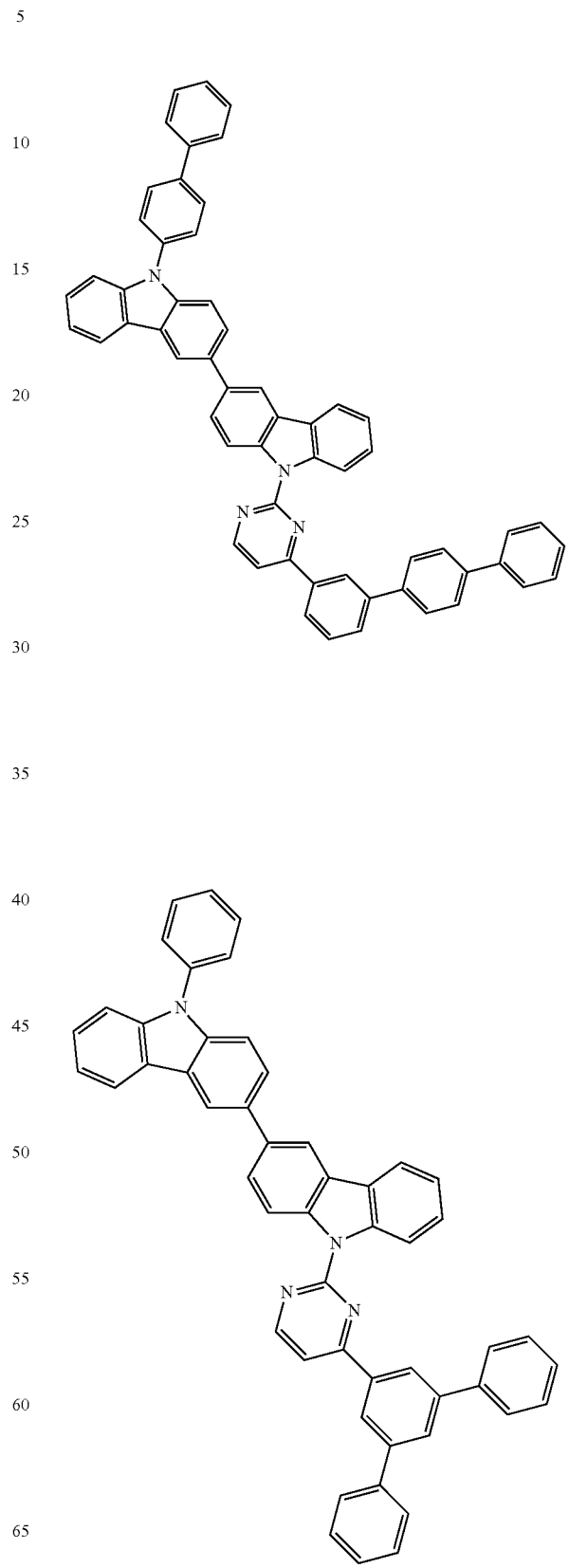

61
-continued
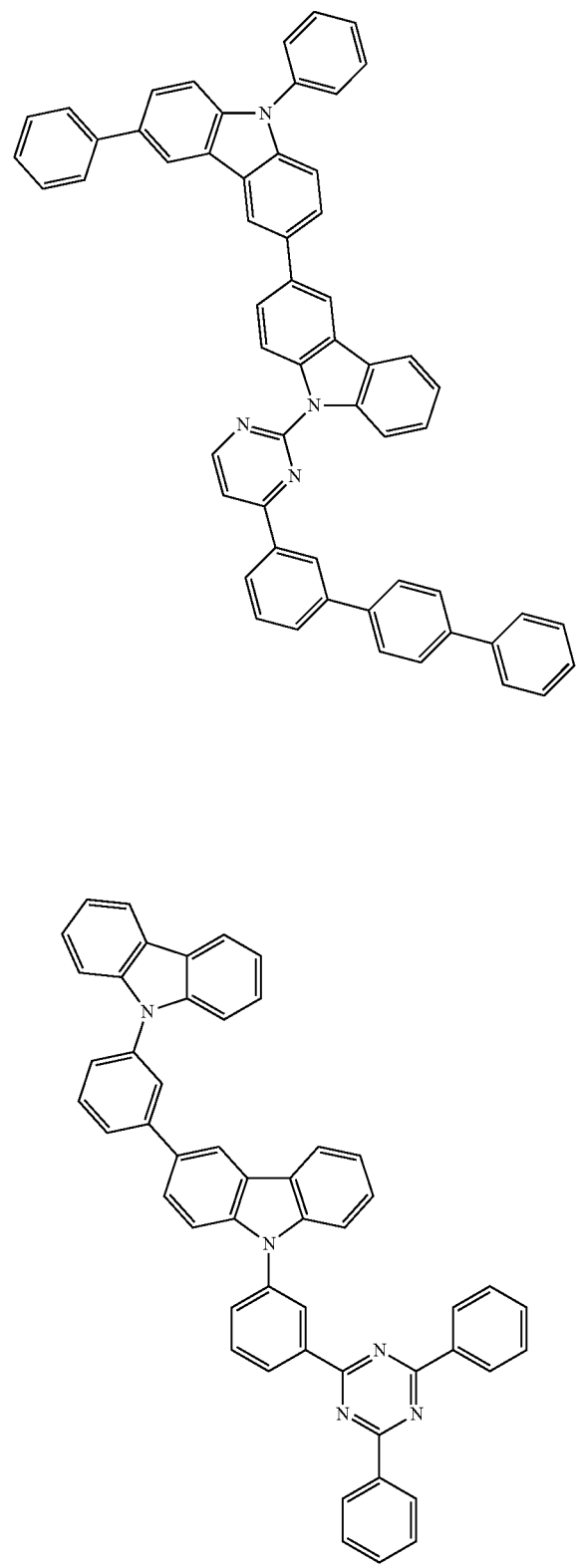
62
-continued
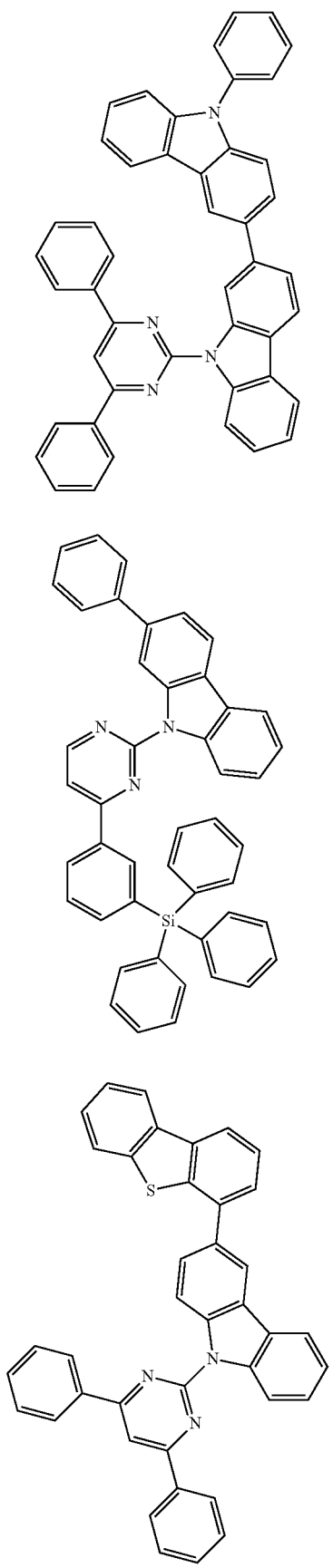

63
-continued
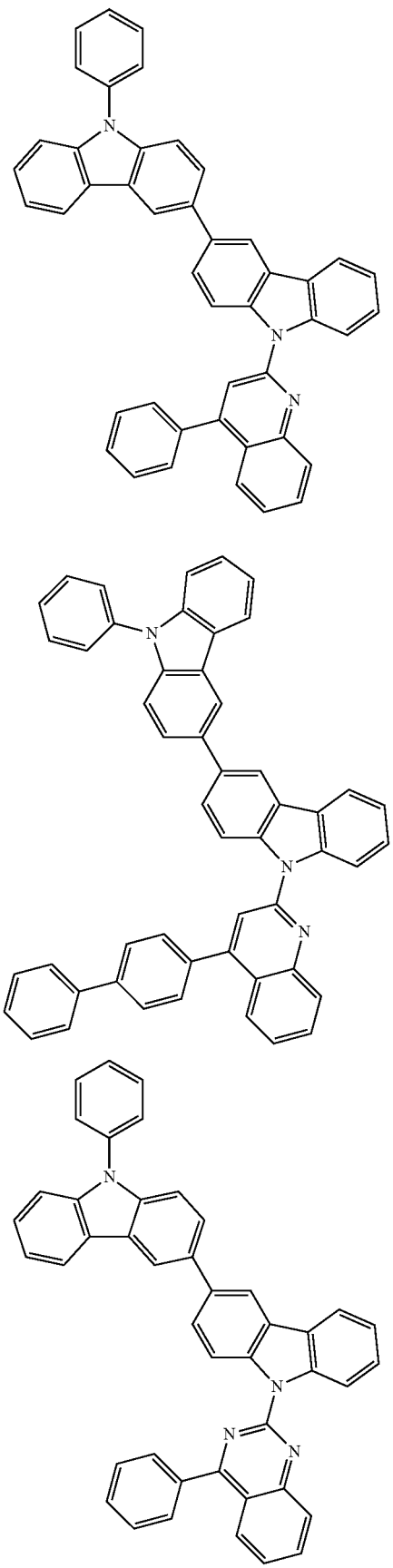
64
-continued
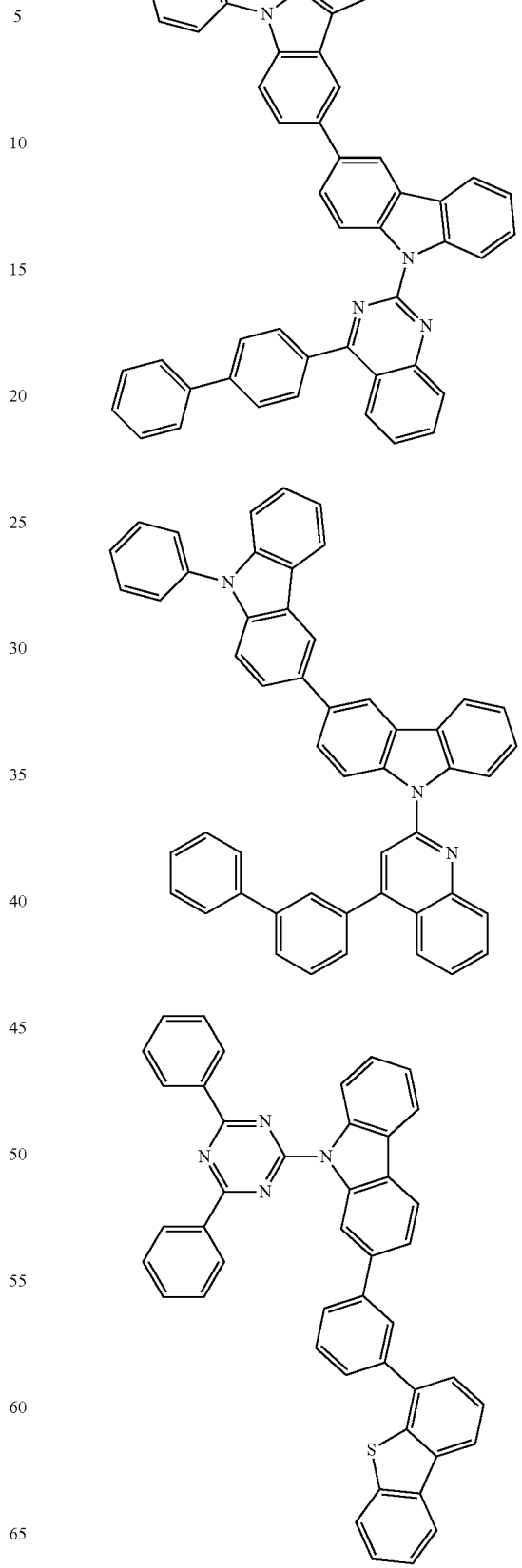

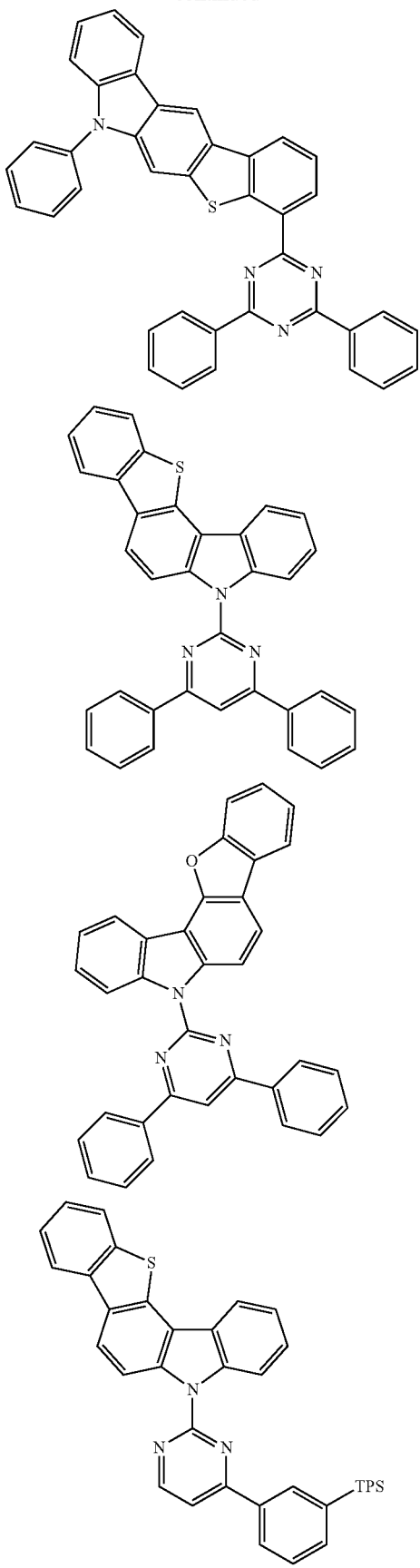
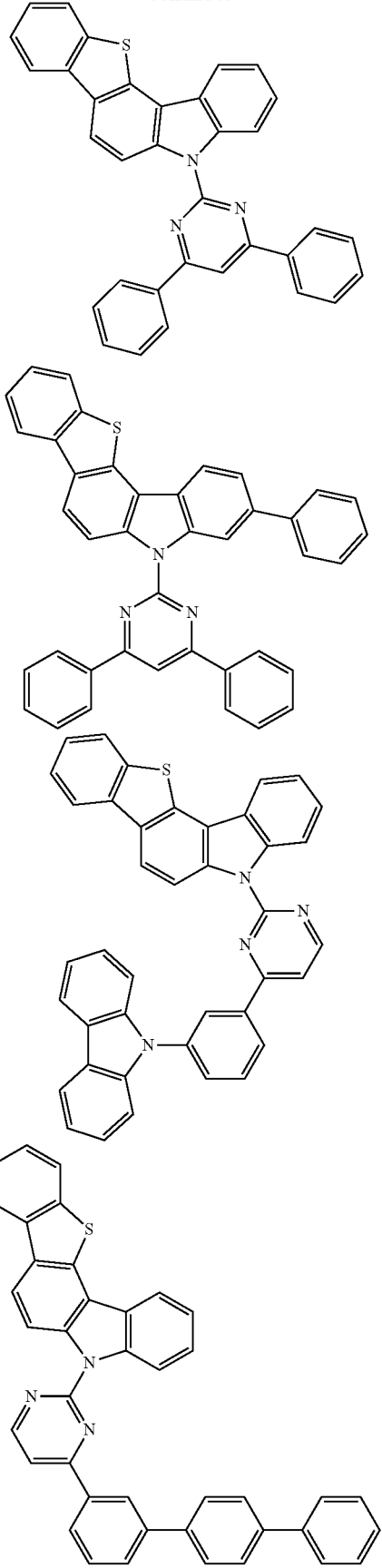

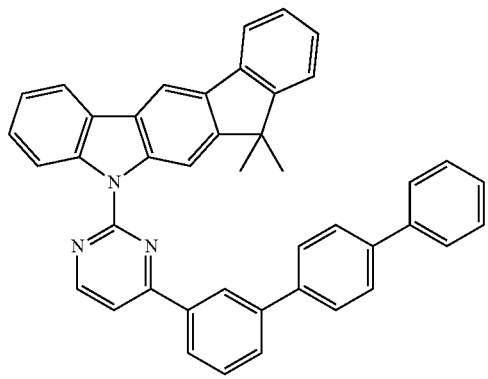
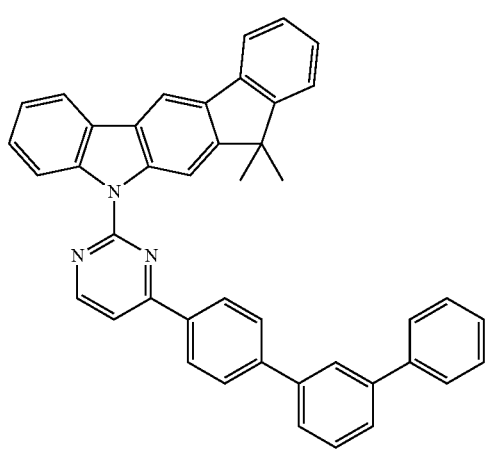
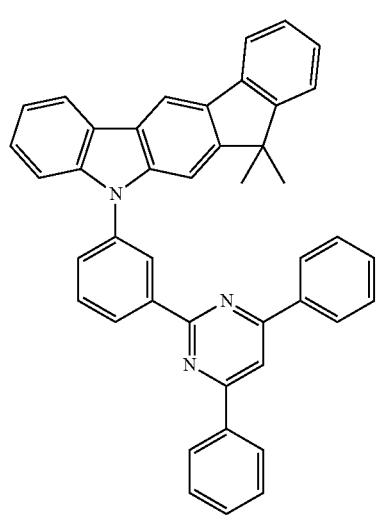
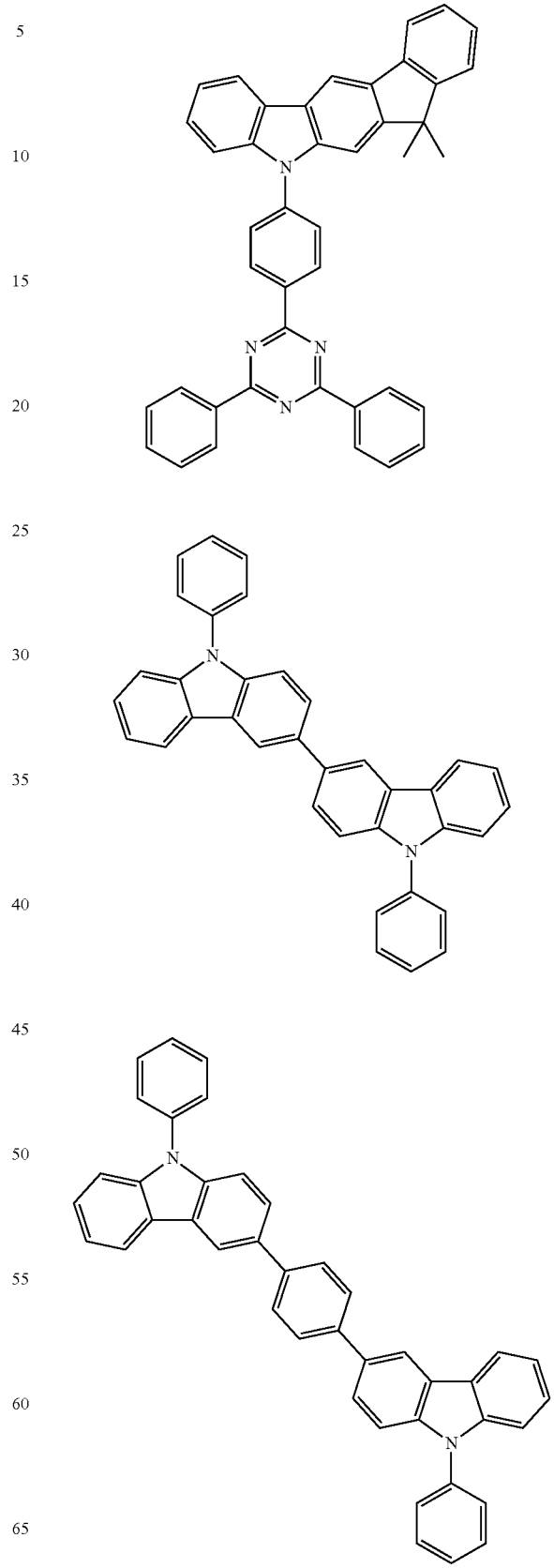

69
-continued
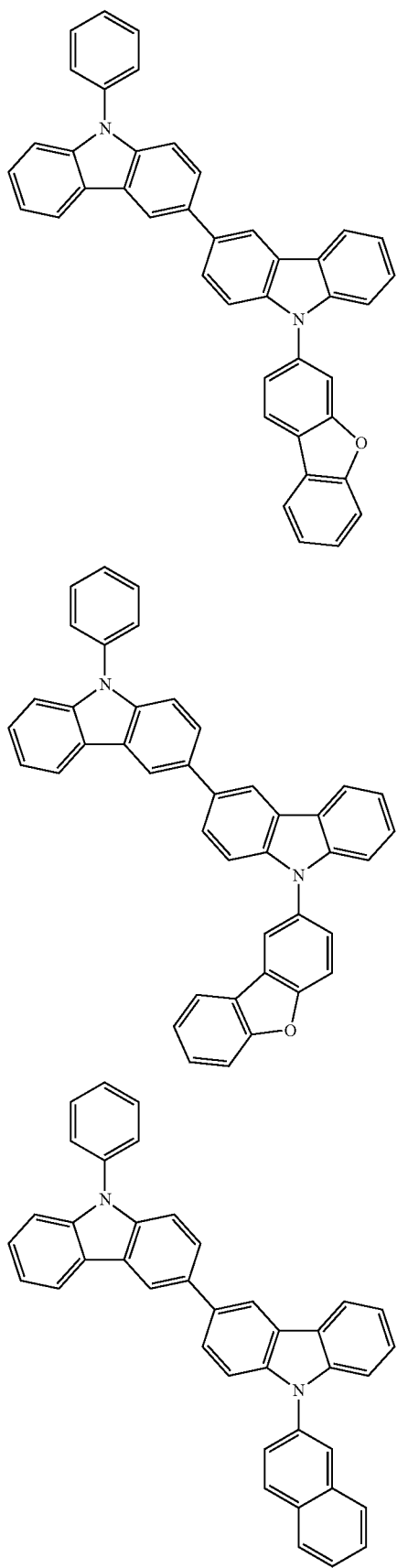
70
-continued
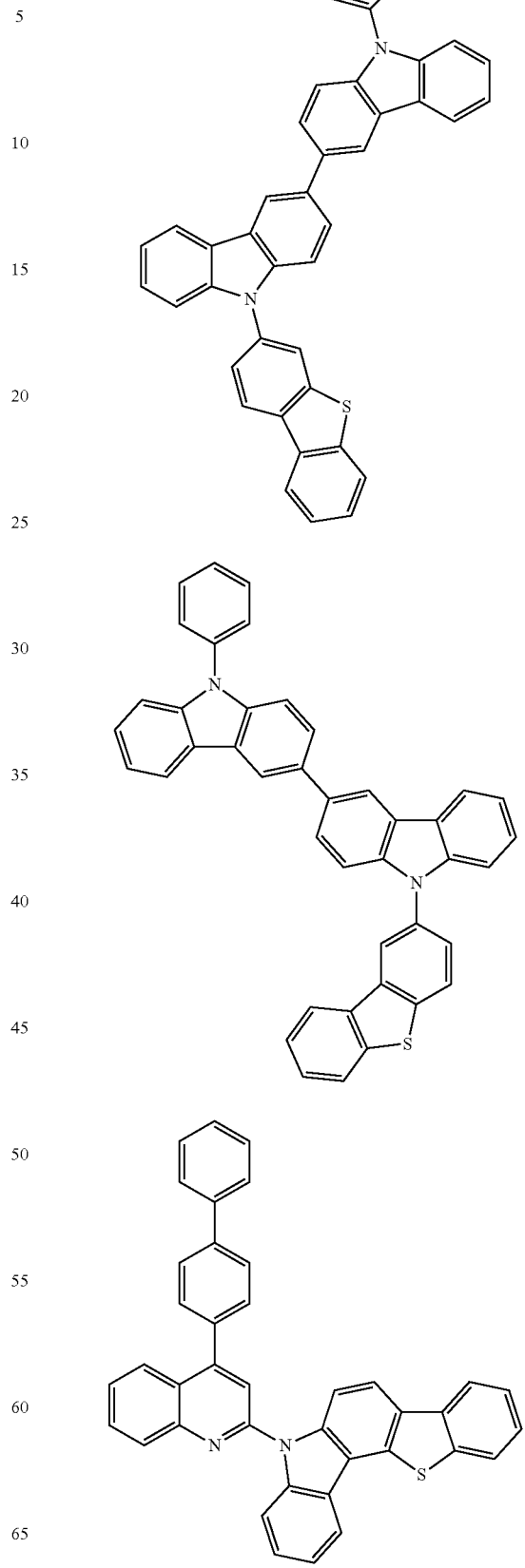

71
-continued
72
-continued
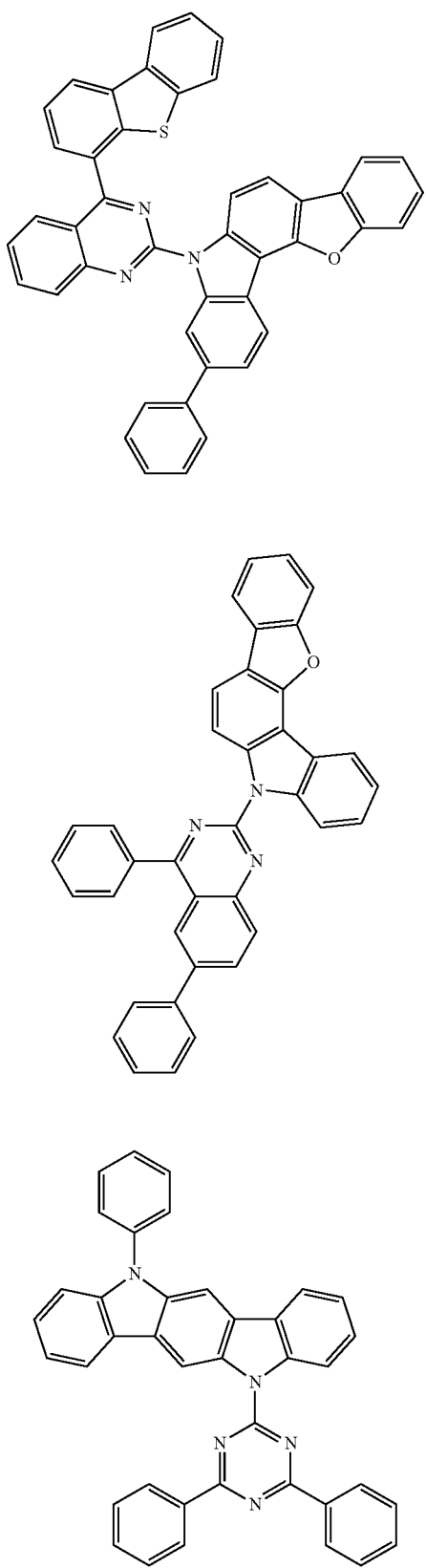
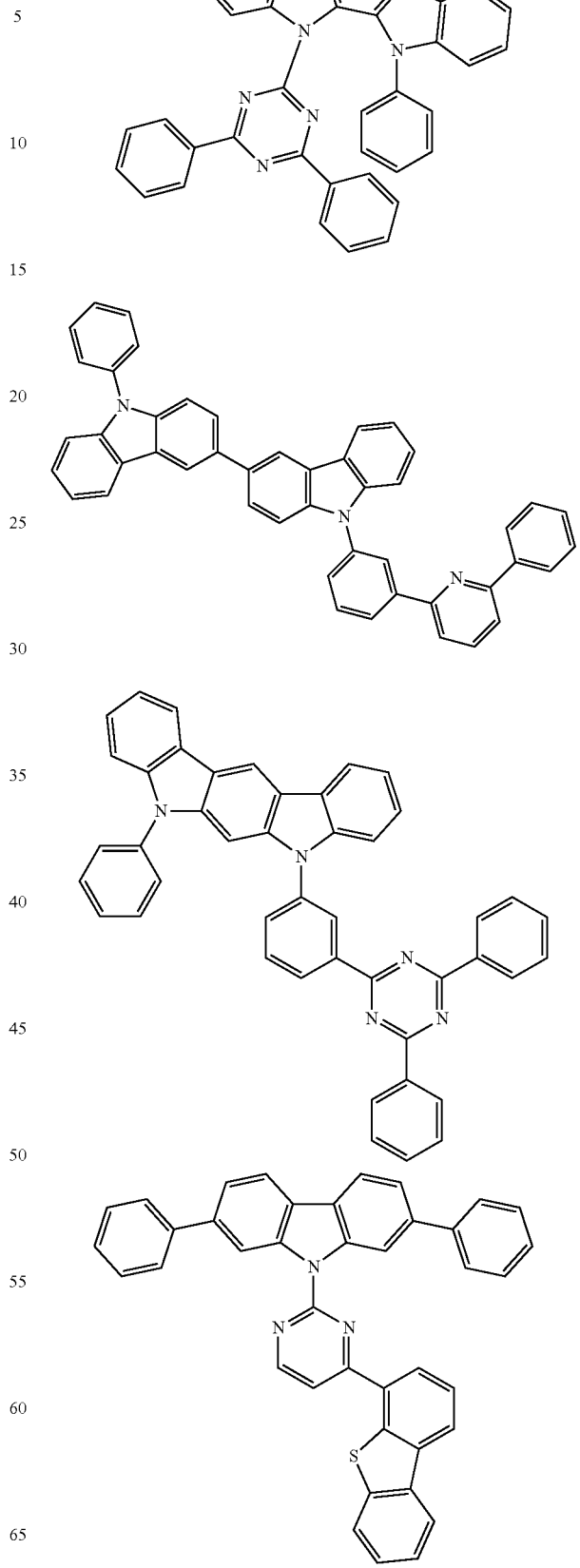

73
-continued
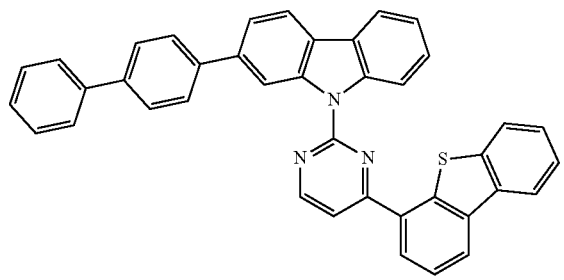
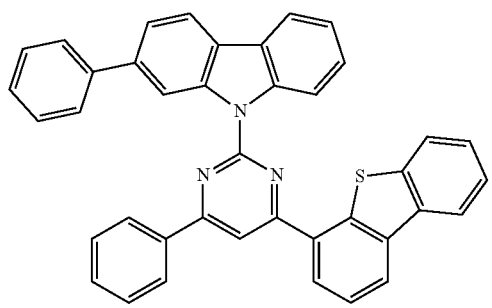
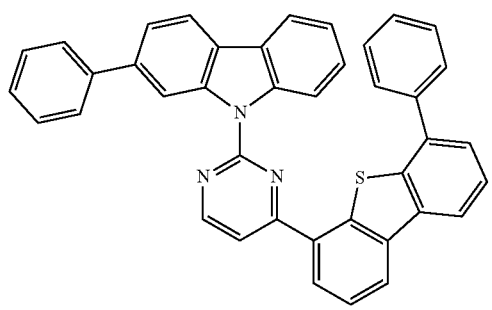
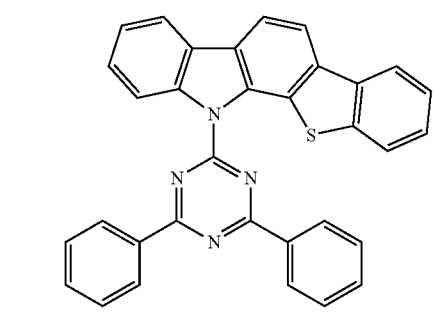
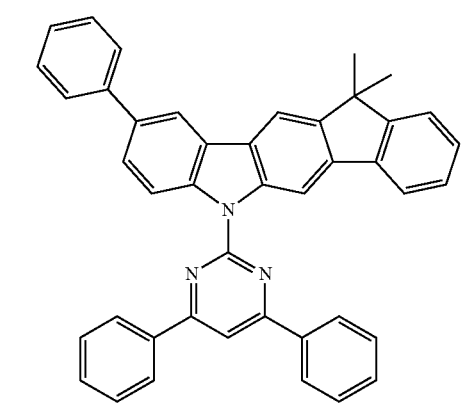
74
-continued
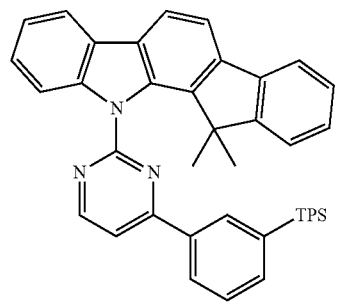
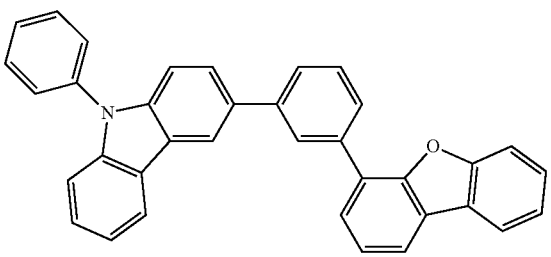
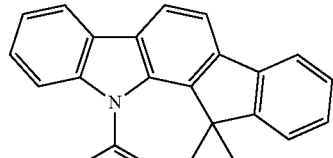
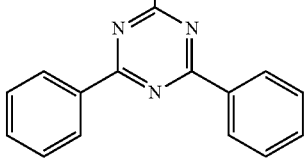
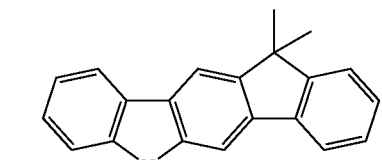
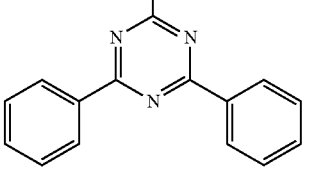

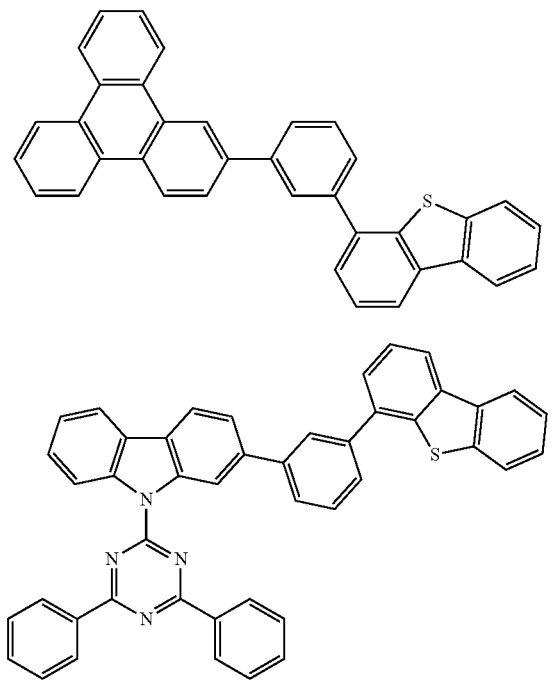

wherein TPS represents a triphenylsilyl group.

The dopants are preferably one or more phosphorescent dopants. The phosphorescent dopant material applied to the organic electroluminescent device of the present invention is not specifically limited, but preferably may be selected from complex compounds of iridium (Ir), osmium (Os), copper (Cu), and platinum (Pt), more preferably ortho-metallated complex compounds of iridium (Ir), osmium (Os), copper (Cu), and platinum (Pt), and even more preferably ortho-metallated iridium complex compounds.

The dopant included in the organic electroluminescent device of the present invention may be selected from the group consisting of the compounds represented by the following formulae 7 to 9:

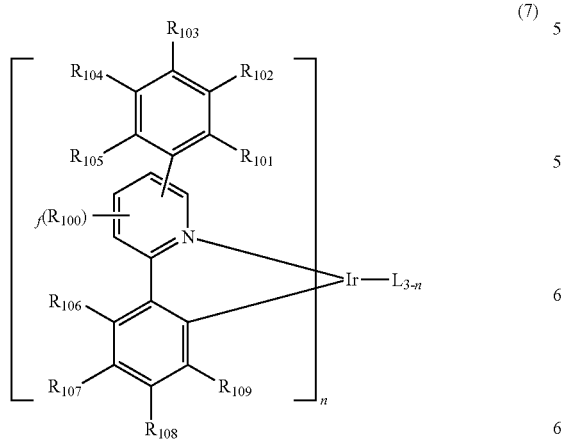

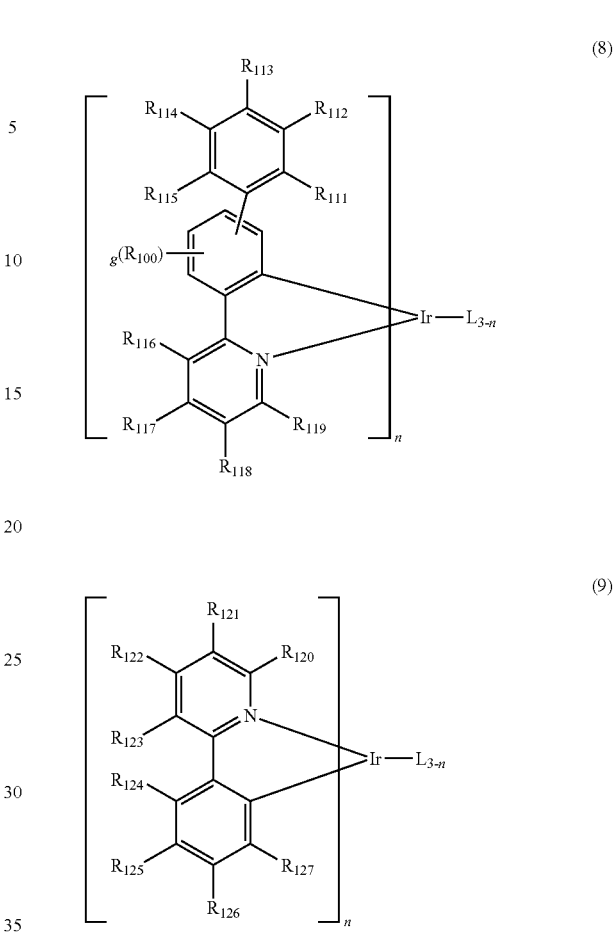

wherein
L is selected from the following structures:

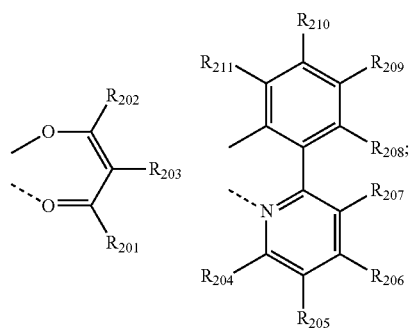

$R_{100}$ represents hydrogen, a substituted or unsubstituted (C1-C30)alkyl group, or a substituted or unsubstituted (C3-C30)cycloalkyl group;

$R_{101}$ to $R_{109}$ and $R_{111}$ to $R_{123}$ each independently represent hydrogen, deuterium, a halogen, a (C1-C30)alkyl group which is unsubstituted or substituted with halogen(s), a substituted or unsubstituted (C3-C30)cycloalkyl group, a substituted or unsubstituted (C6-C30)aryl group, a cyano group, or a substituted or unsubstituted (C1-C30)alkoxy group; and $R_{106}$ to $R_{109}$ are linked to an adjacent substituent(s) to form a substituted or unsubstituted fused ring, for example, fluorene which is unsubstituted or substituted with an alkyl group, dibenzothiophene which is unsubstituted or substituted with an alkyl group, or dibenzofuran which is unsubstituted or substituted with an alkyl group; $R_{120}$ to $R_{123}$ are linked to an adjacent substituent(s) to form a substituted or unsubstituted fused ring, for example, quinoline which is unsubstituted or substituted with an alkyl or aryl group;

$R_{124}$ to $R_{127}$ each independently represent hydrogen, deuterium, a halogen, a substituted or unsubstituted (C1-C30)alkyl group, or a substituted or unsubstituted (C6-C30)aryl group; $R_{124}$ to $R_{127}$ are linked to an adjacent substituent(s) to form a substituted or unsubstituted fused ring, for example, fluorene which is unsubstituted or substituted with an alkyl group, dibenzothiophene which is unsubstituted or substituted with an alkyl group, or dibenzofuran which is unsubstituted or substituted with an alkyl group;

$R_{201}$ to $R_{211}$ each independently represent hydrogen, deuterium, a halogen, a (C1-C30)alkyl group unsubstituted or substituted with halogen(s), a substituted or unsubstituted (C3-C30)cycloalkyl group, or a substituted or unsubstituted (C6-C30)aryl group; $R_{208}$ to $R_{211}$ are linked to an adjacent substituent(s) to form a substituted or unsubstituted fused ring, for example, fluorene which is unsubstituted or substituted with an alkyl group, dibenzothiophene which is unsubstituted or substituted with an alkyl group, or dibenzofuran which is unsubstituted or substituted with an alkyl group;

f and g each independently represent an integer of 1 to 3; where f or g is an integer of 2 or more, each $R_{100}$ may be the same or different; and n represents an integer of 1 to 3.

The dopant compound includes the following:

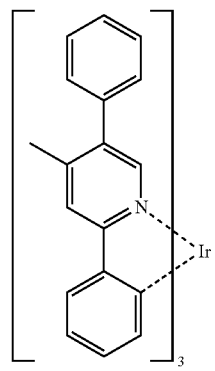

D-1

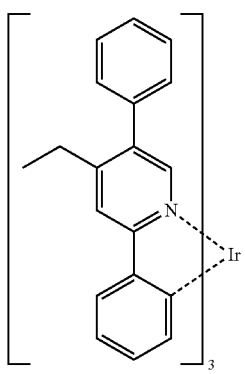

D-2

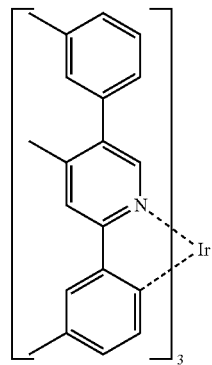

D-3

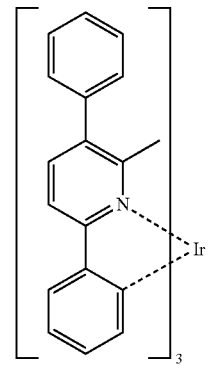

D-4

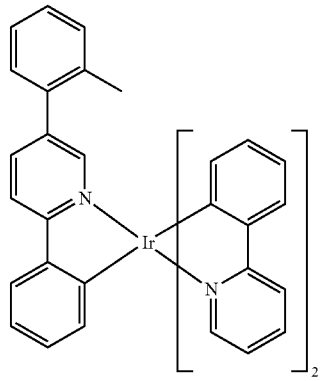

D-5

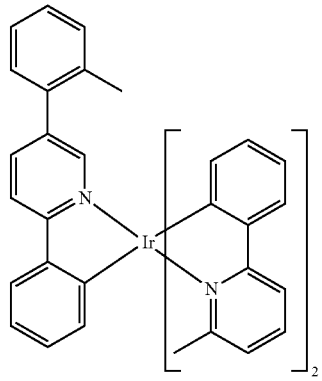

D-6

-continued
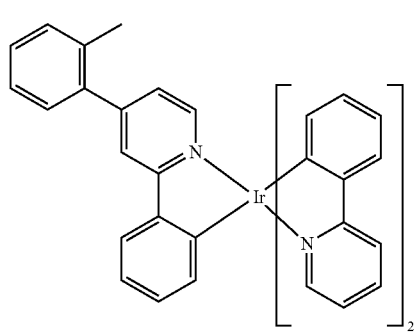
D-7
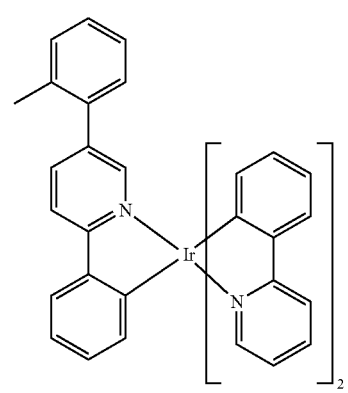
D-8
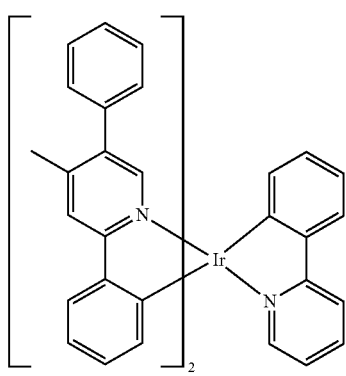
D-9
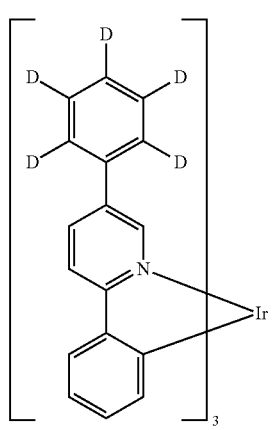
D-10
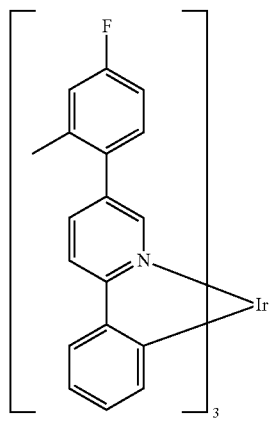
D-11
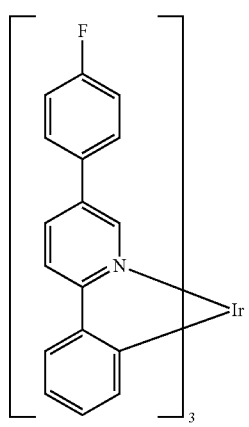
D-12
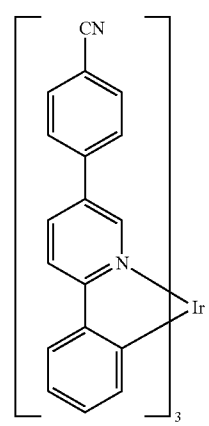
D-13

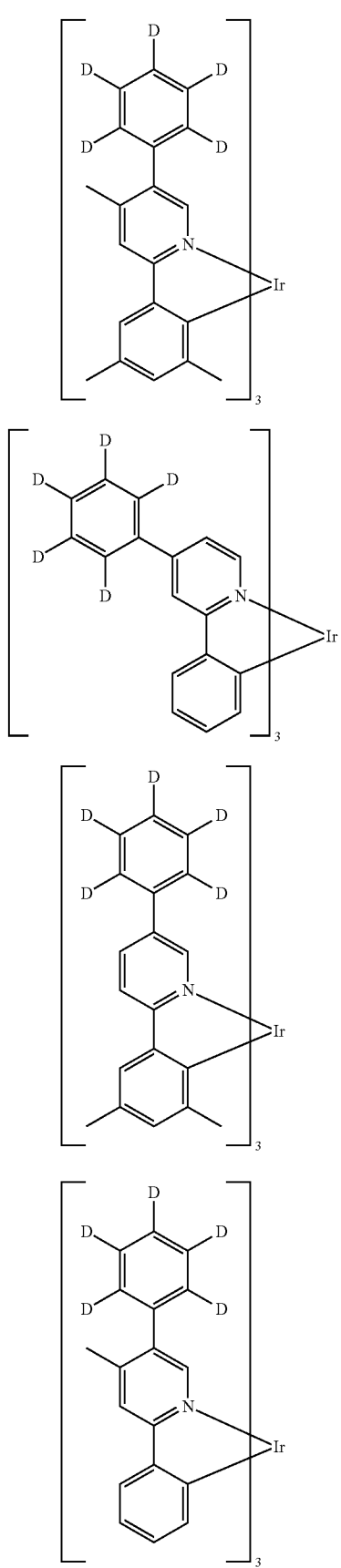
D-14
D-15
D-16
D-17
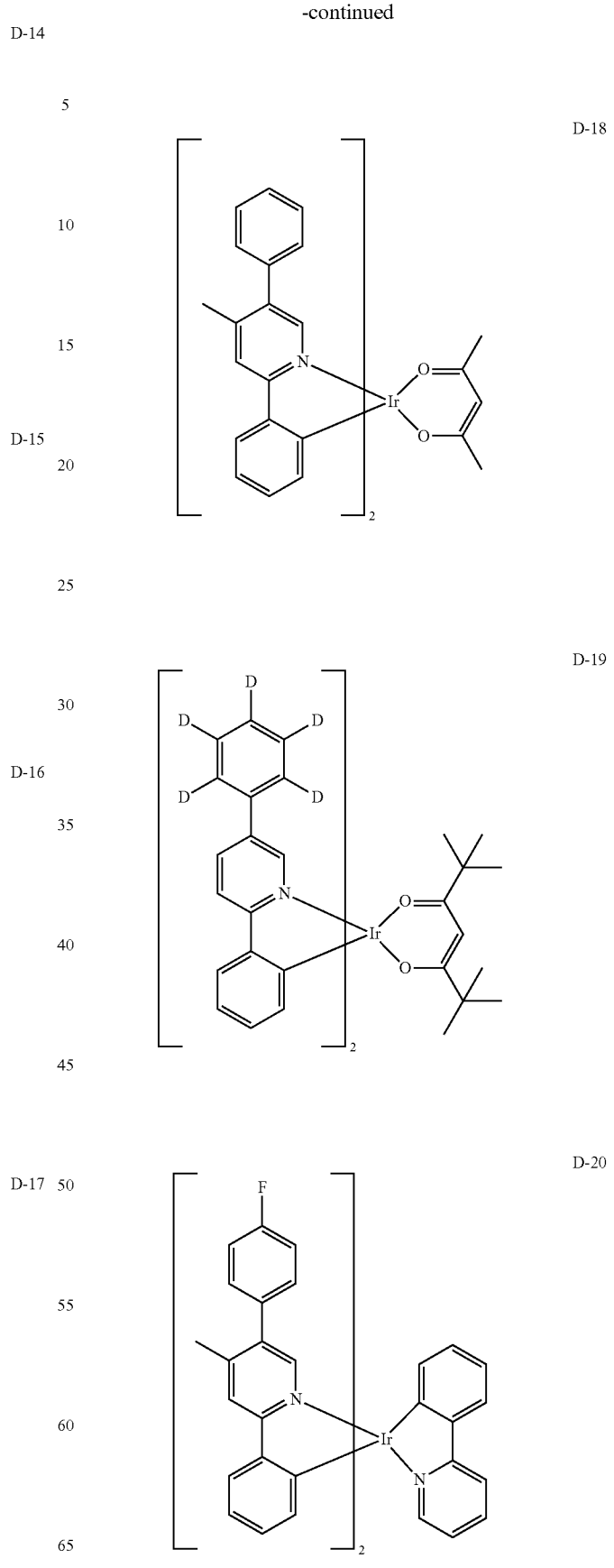
D-18
D-19
D-20

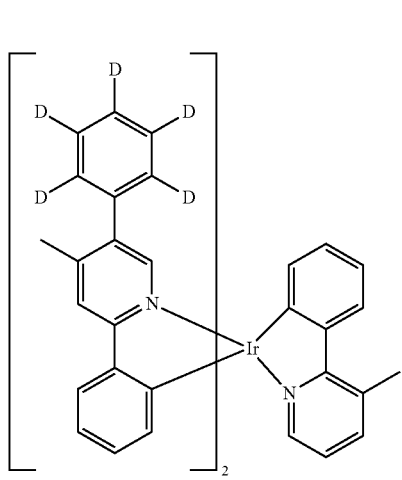
D-21
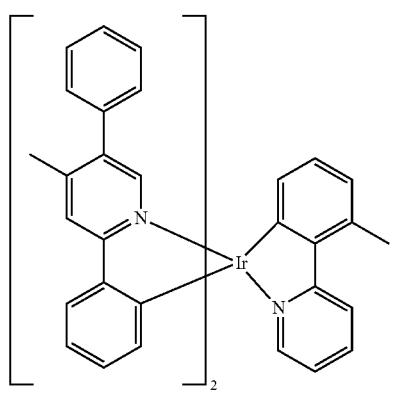
D-22
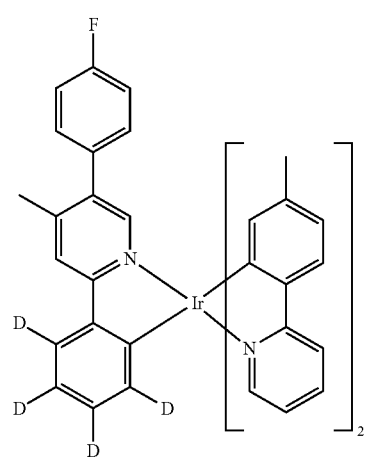
D-23
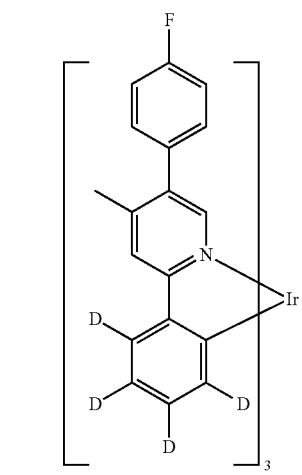
D-24
D-25
D-26

D-27
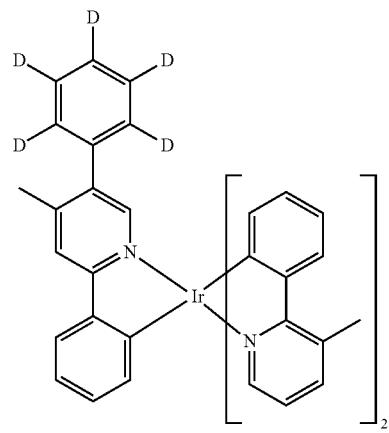
D-28
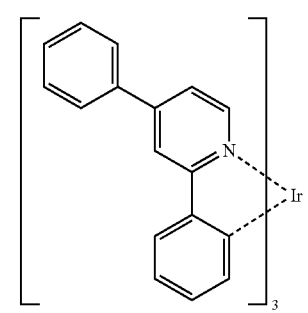
D-29
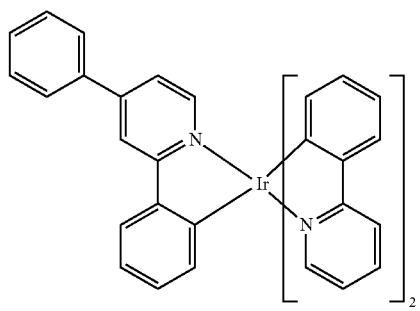
D-30
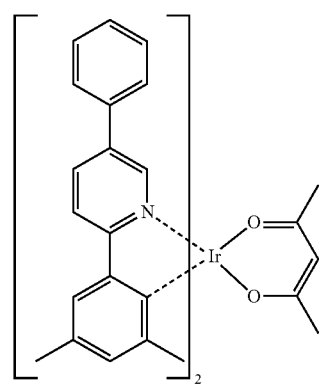
D-31
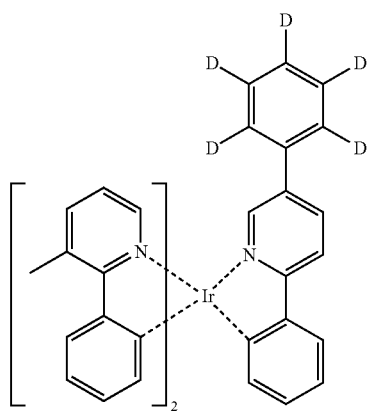
D-32
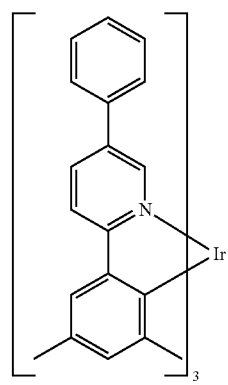
D-33
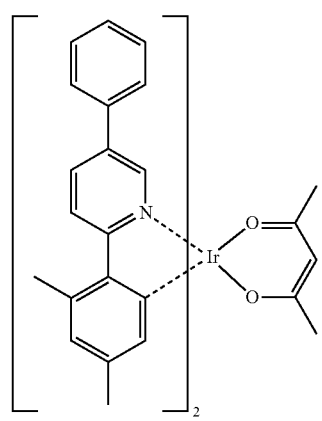
D-34
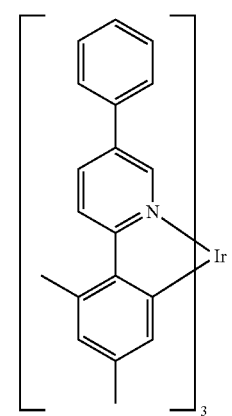

D-35
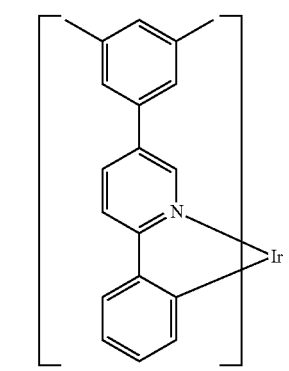
D-36
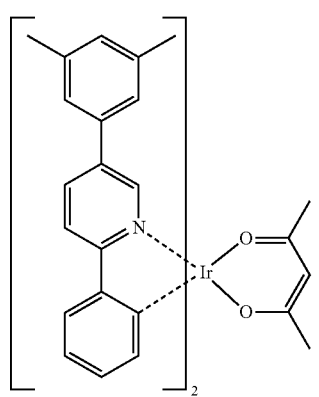
D-37
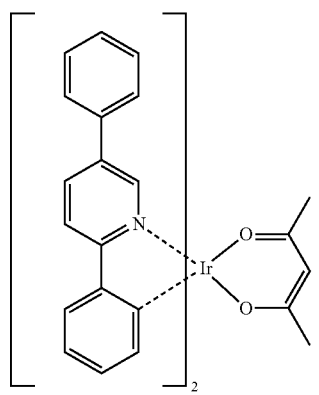
D-38
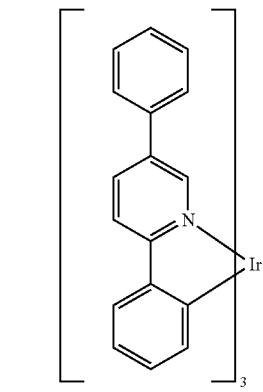
D-39
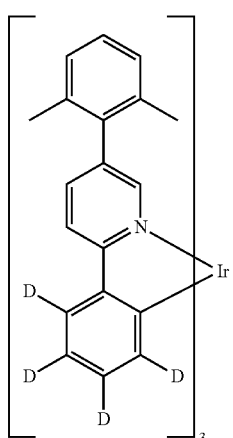
D-40
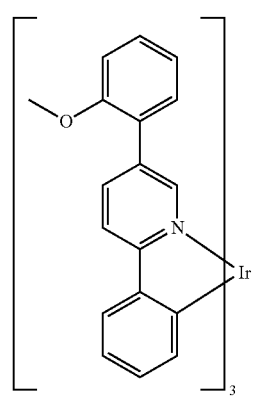
D-41
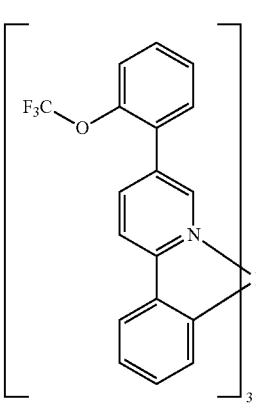
D-42
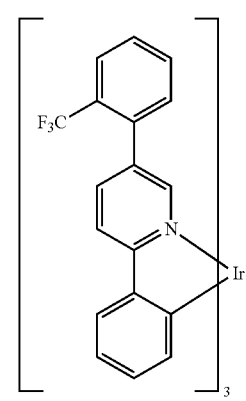

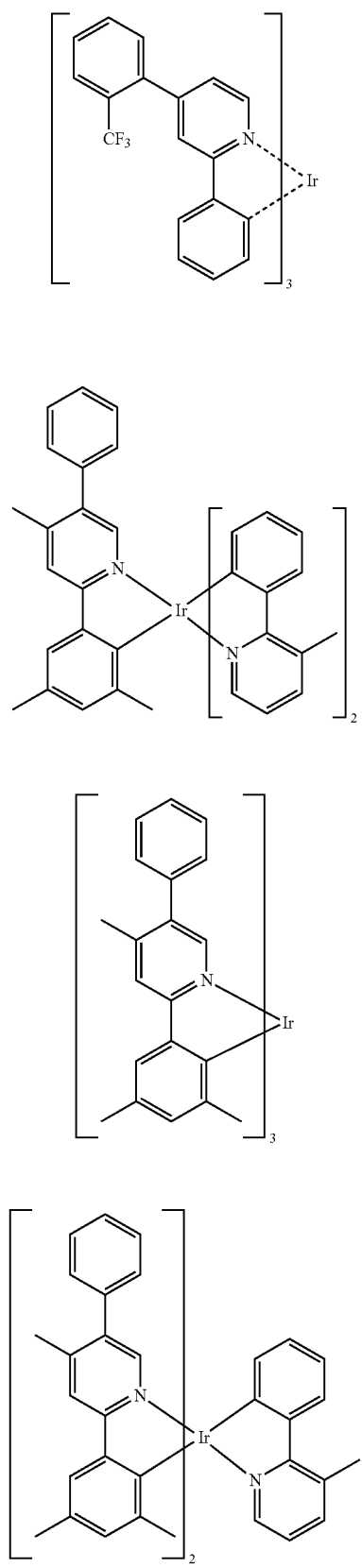
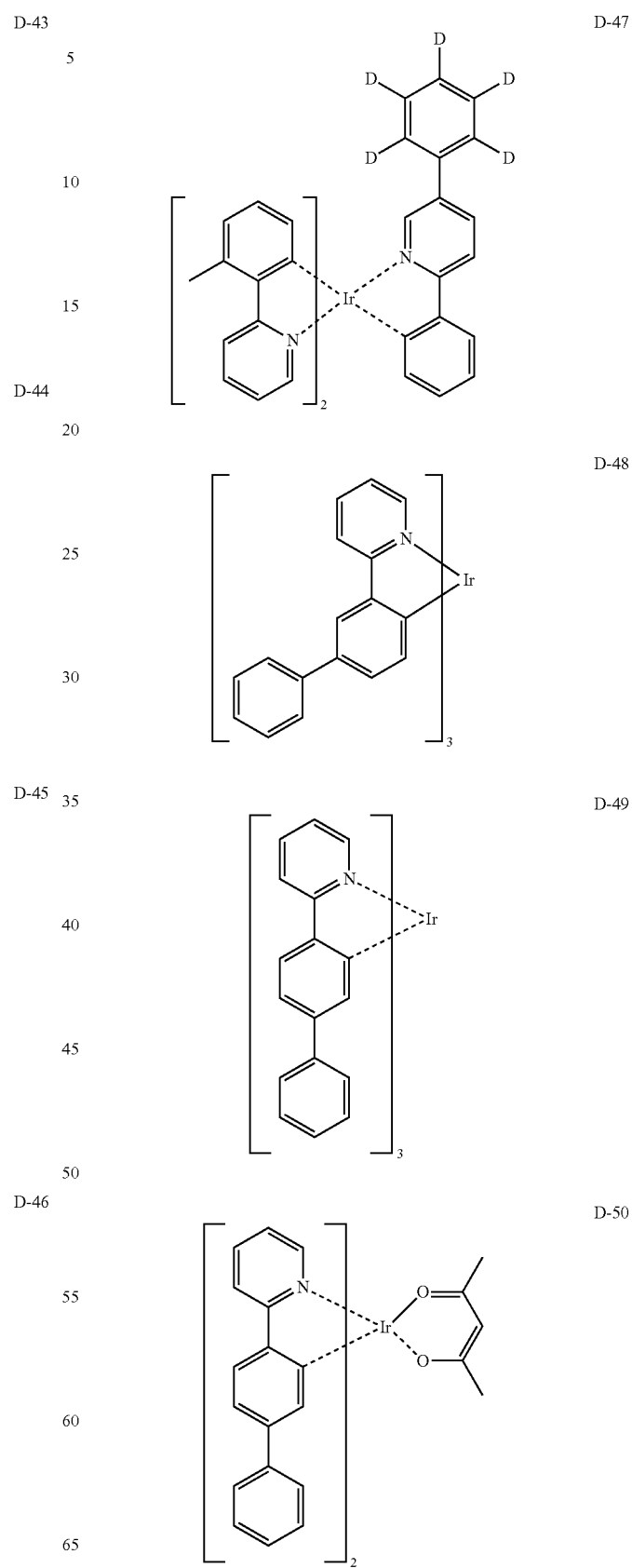

-continued
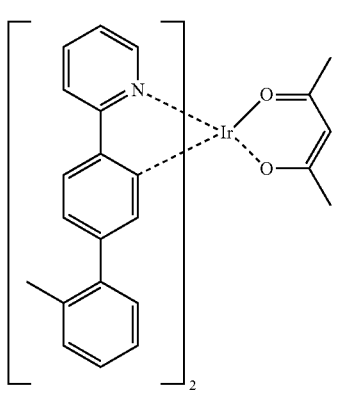
D-51
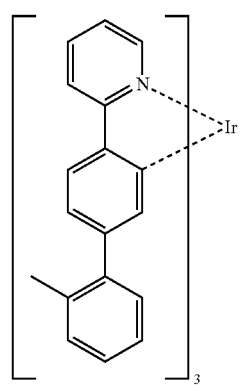
D-52
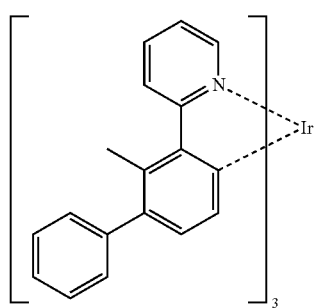
D-53
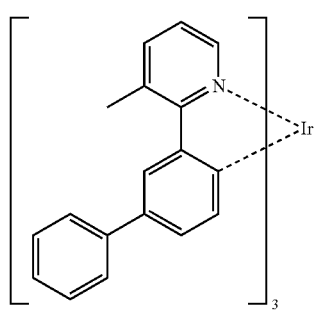
D-54
-continued
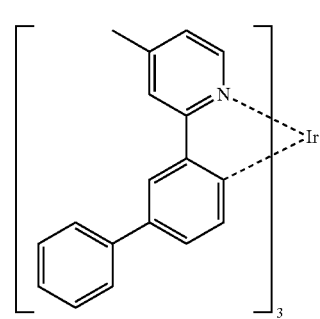
D-55
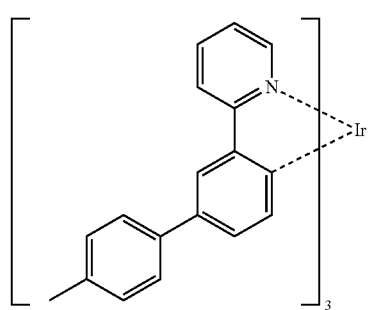
D-56
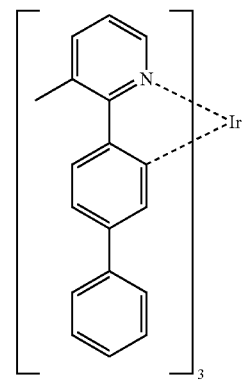
D-57
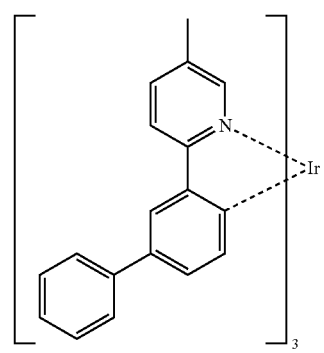
D-58

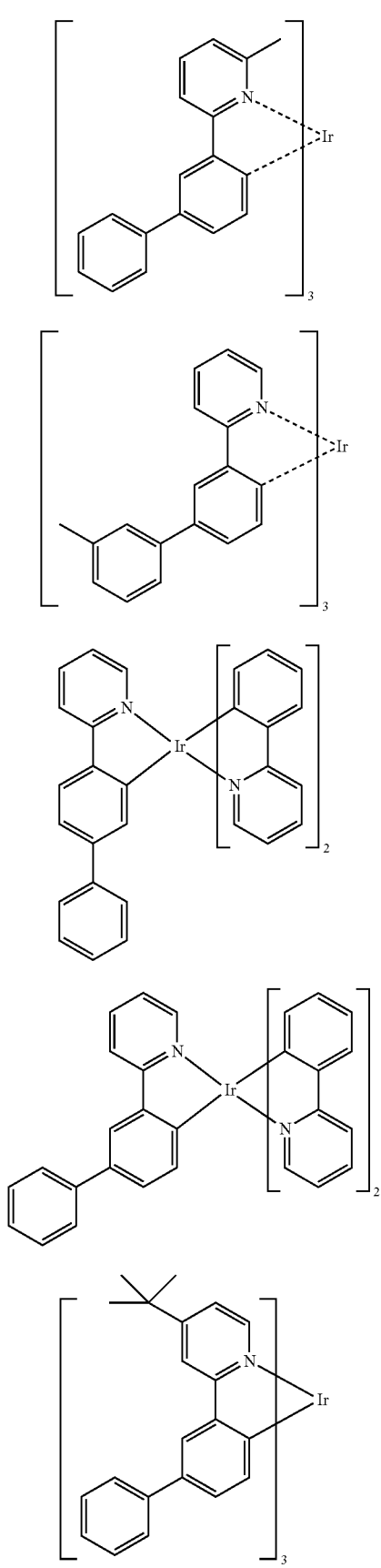
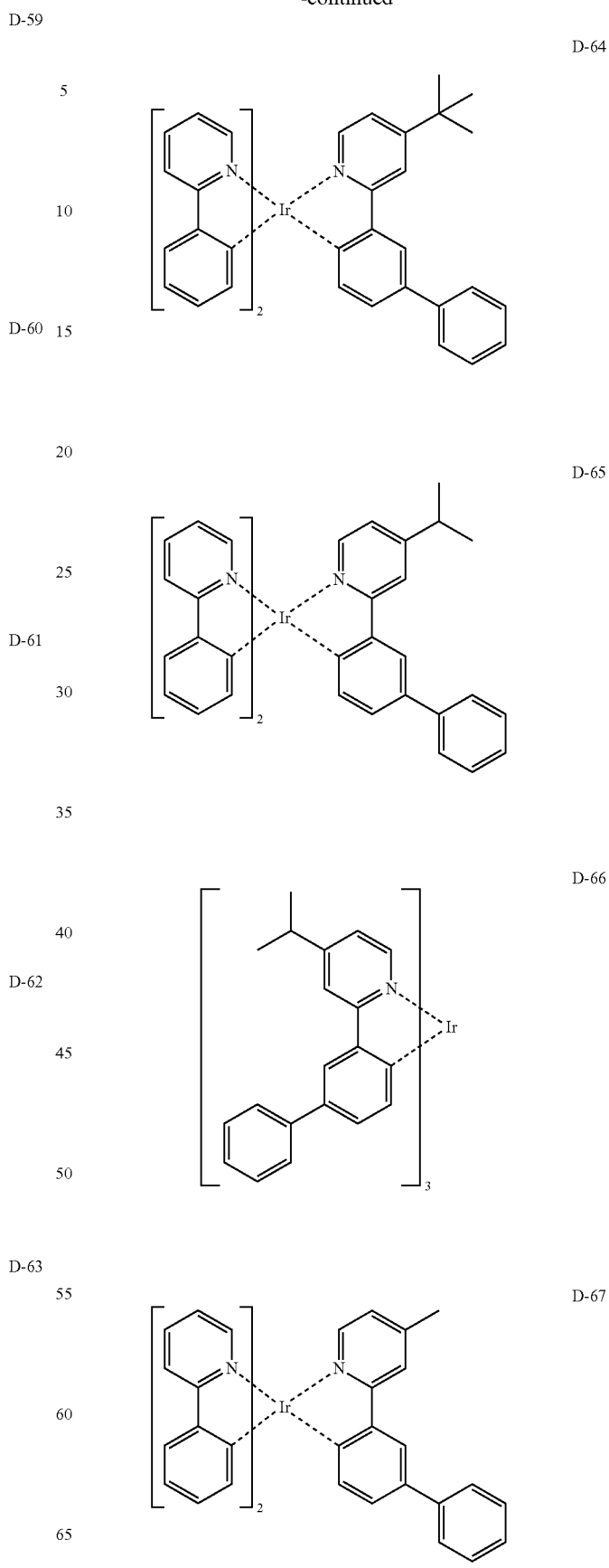

D-68
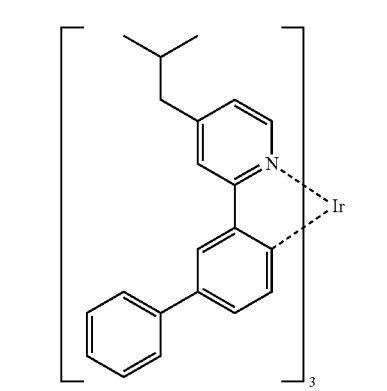
D-69
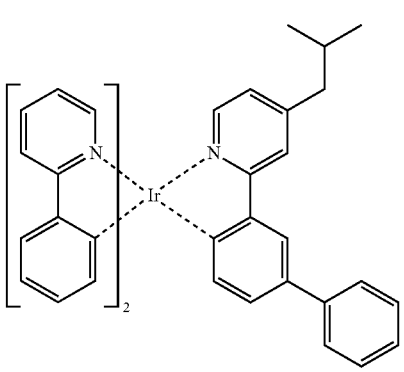
D-70
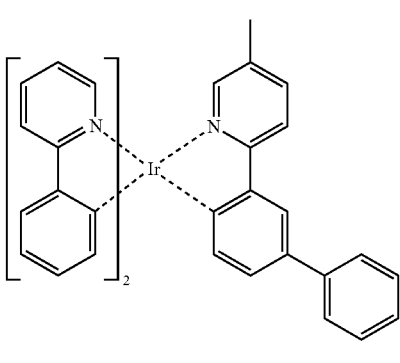
D-71
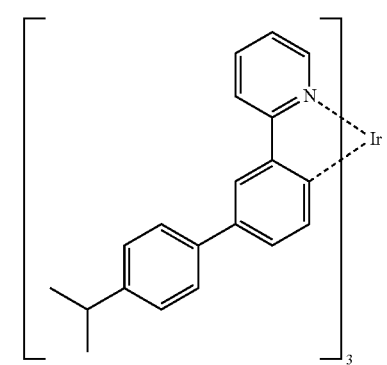
D-72
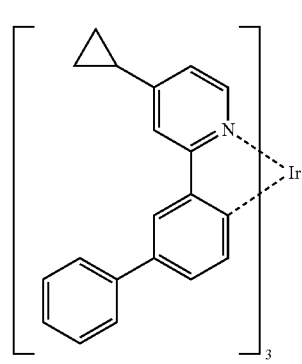
D-73
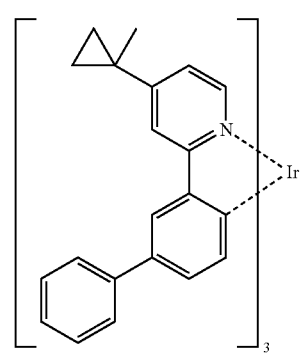
D-74
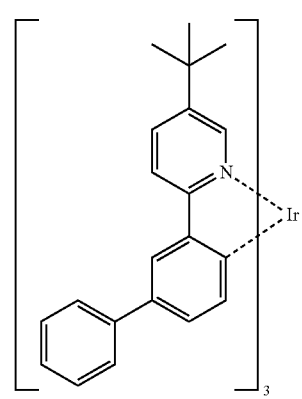
D-75
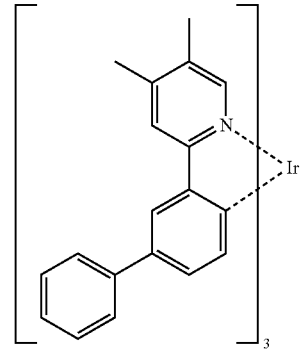

D-76
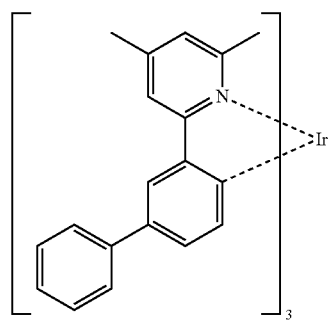
D-77
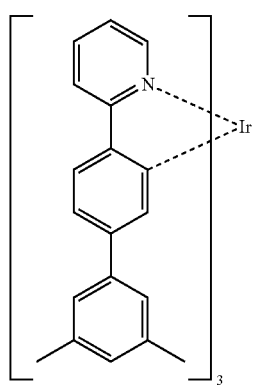
D-78
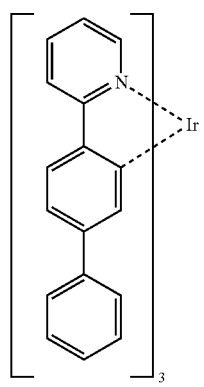
D-79
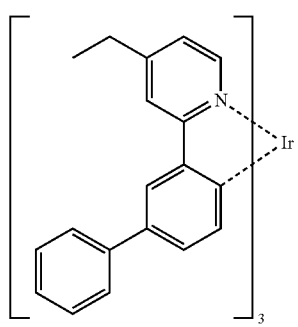
D-80
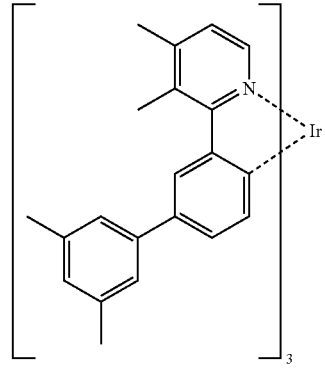
D-81
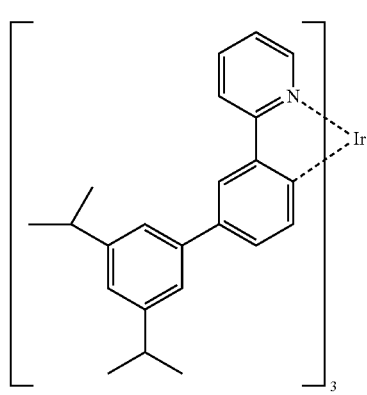
D-82
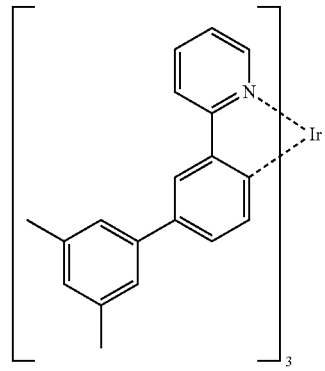
D-83
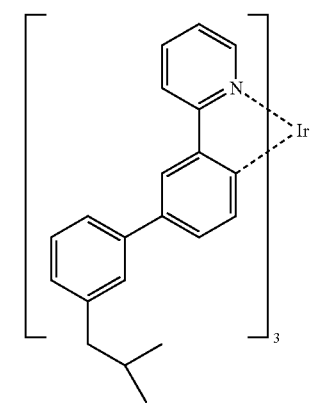

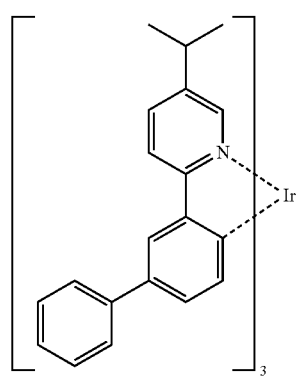
D-84
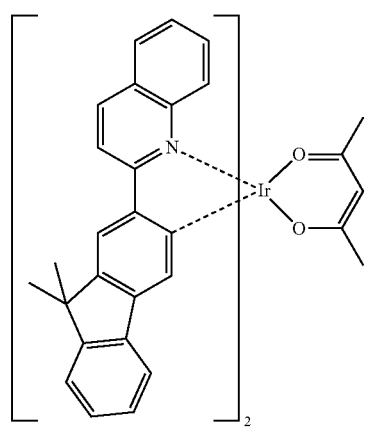
D-88
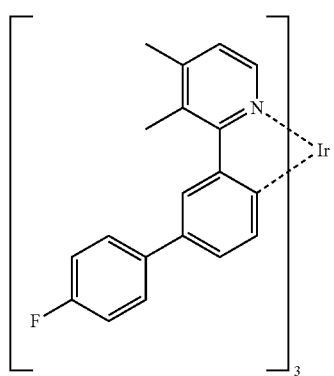
D-85
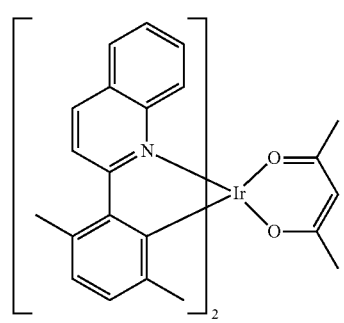
D-89
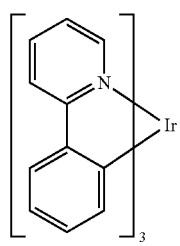
D-86
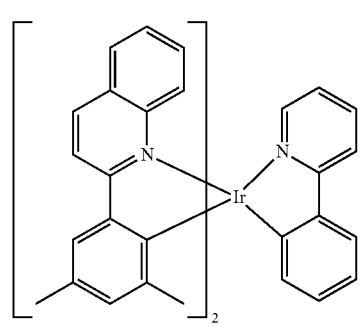
D-90
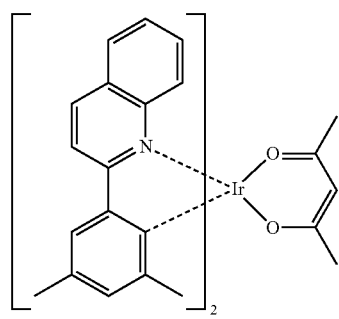
D-87
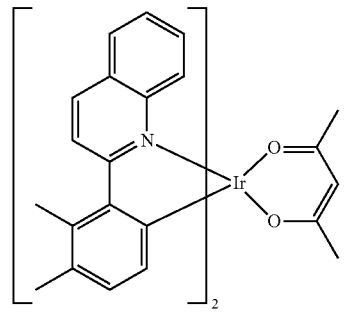
D-91

D-92
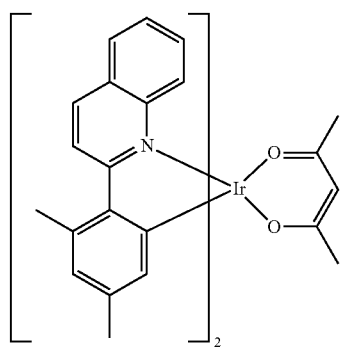
D-93
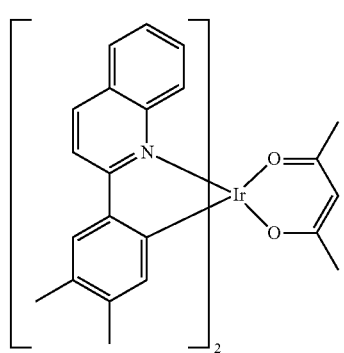
D-94
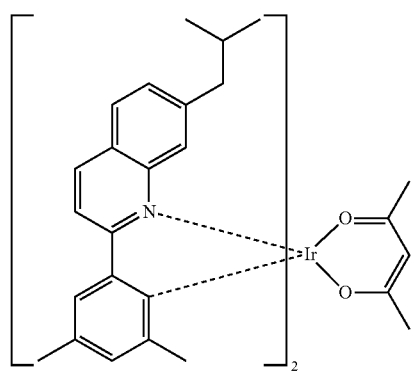
D-95
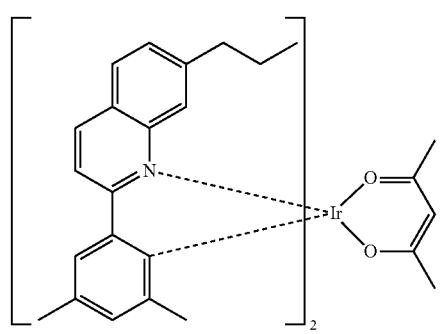
D-96
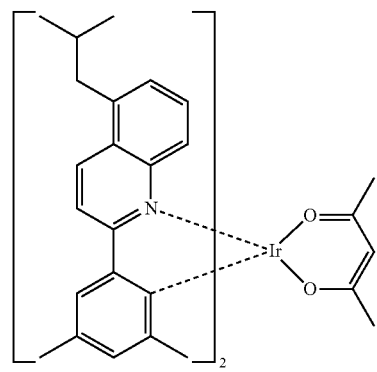
D-97
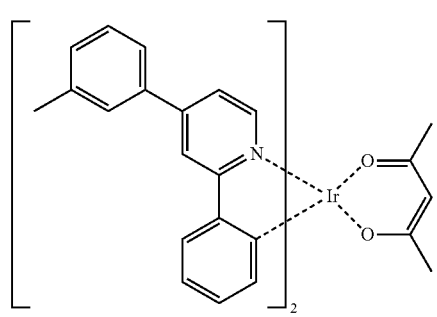
D-98
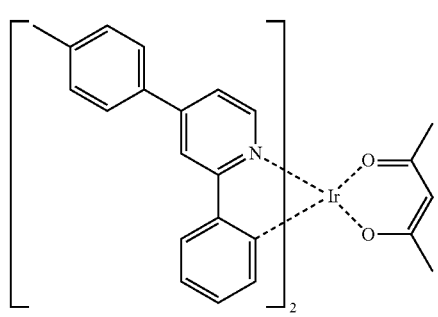
D-99
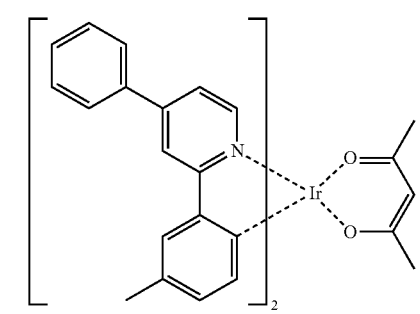
D-100
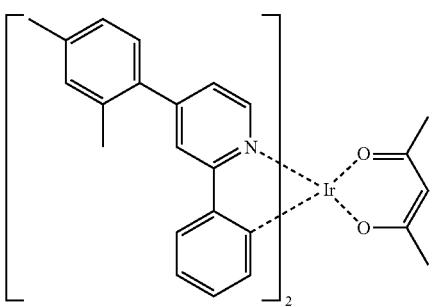

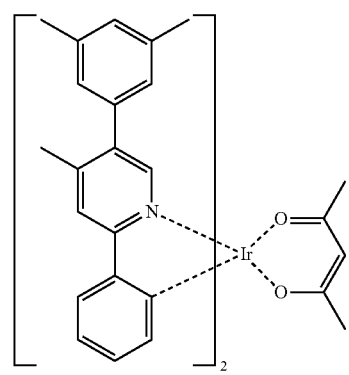
D-101
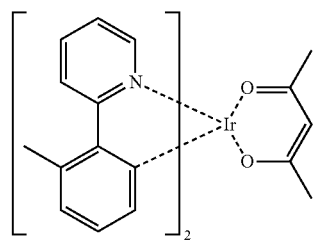
D-106
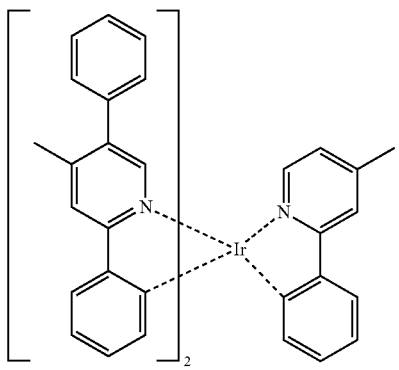
D-102, D-107
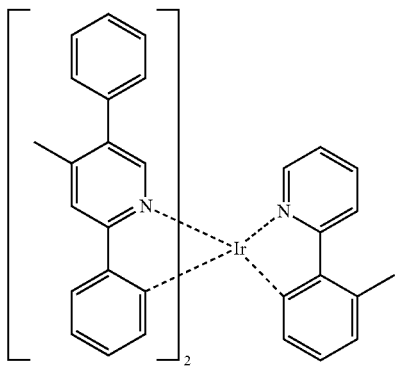
D-103, D-108
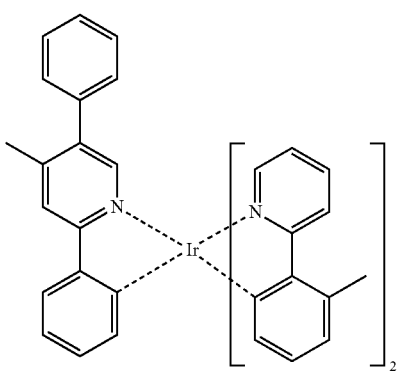
D-104, D-109
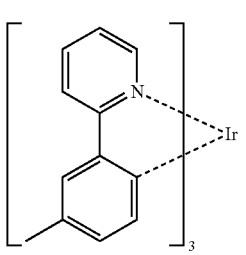
D-105, D-110

D-111
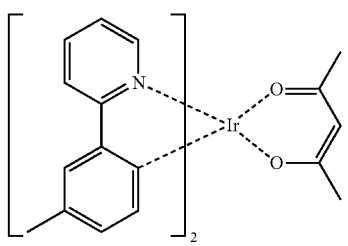
D-112
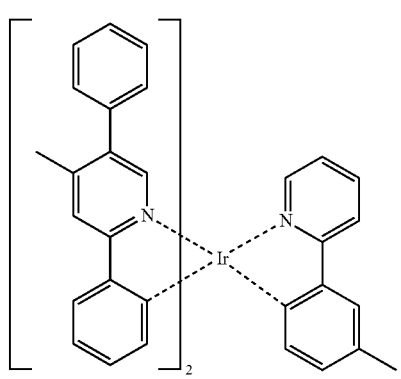
D-113
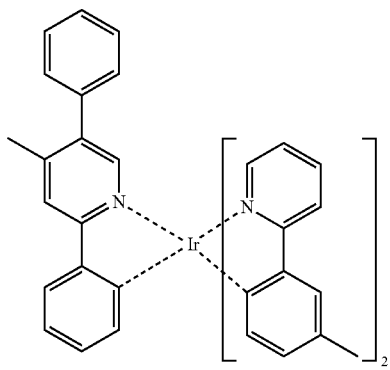
D-114
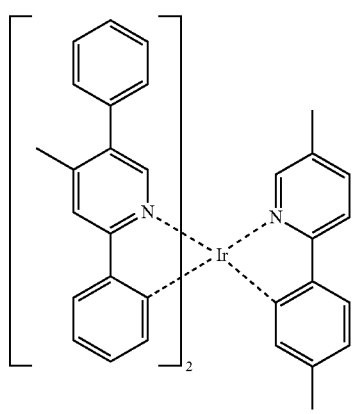
D-115
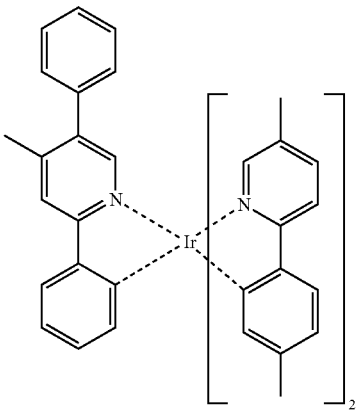
D-116
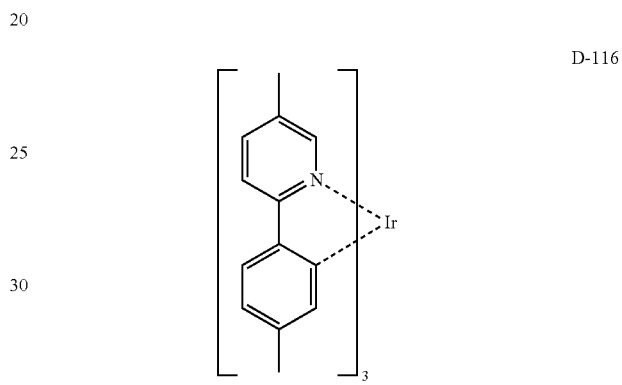
D-117
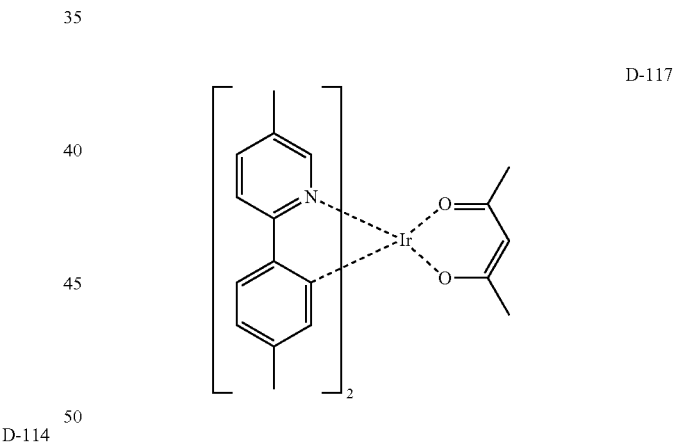
D-118
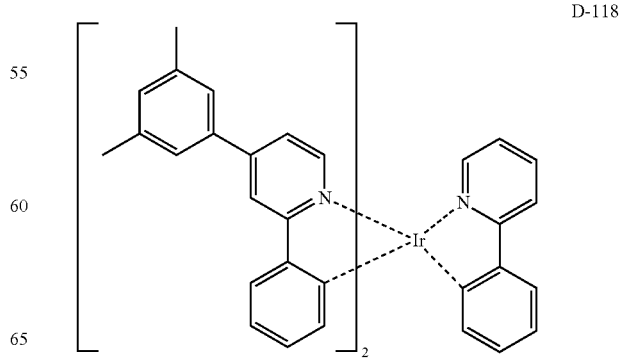

D-119
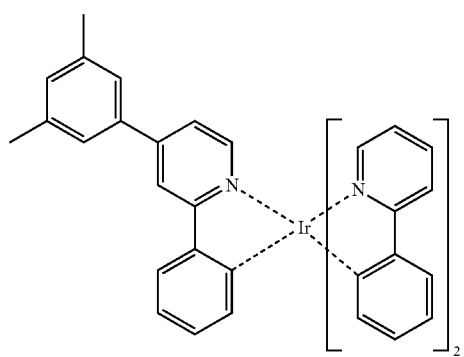
D-123
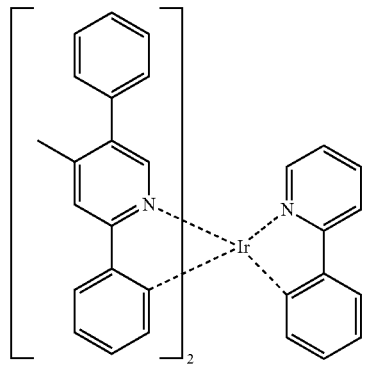
D-120
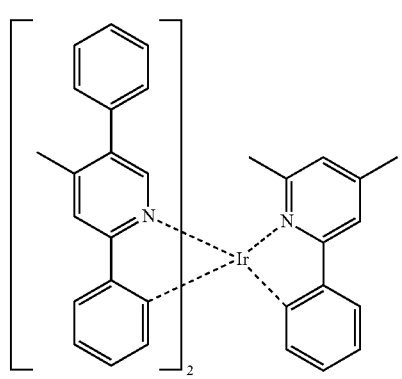
D-124
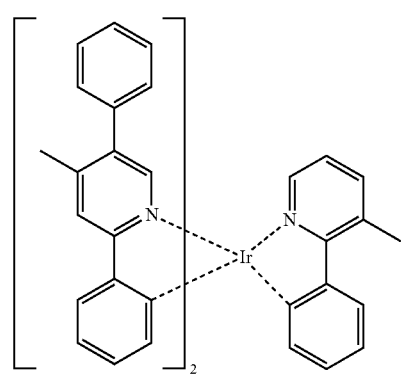
D-121
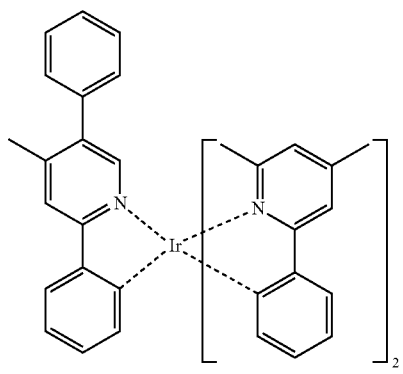
D-125
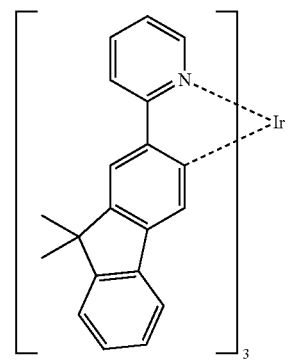
D-122
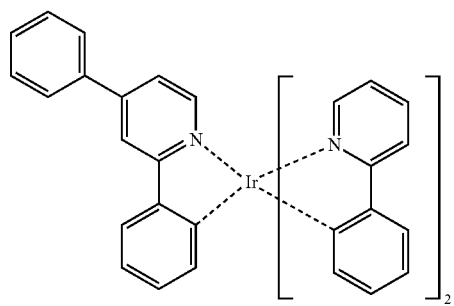
D-126
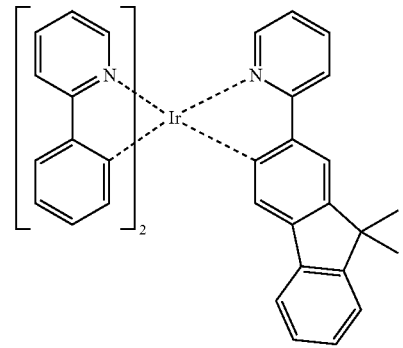

D-127 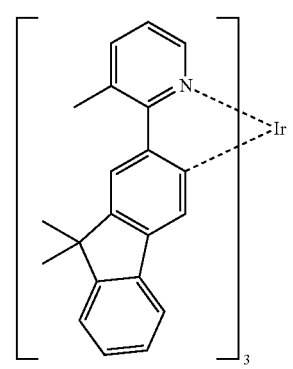
D-132 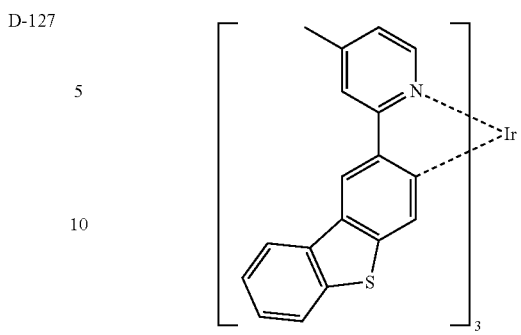
D-128 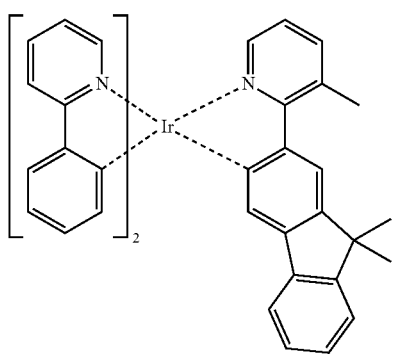
D-133 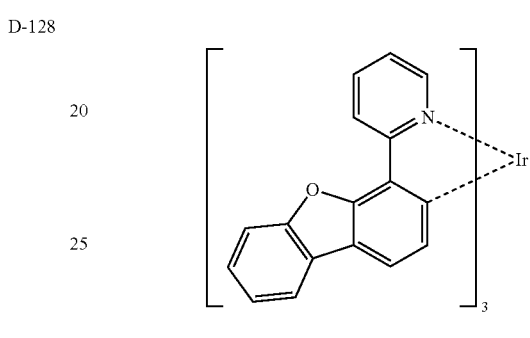
D-129 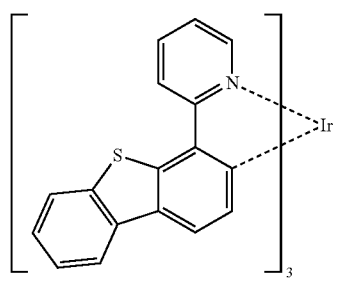
D-134 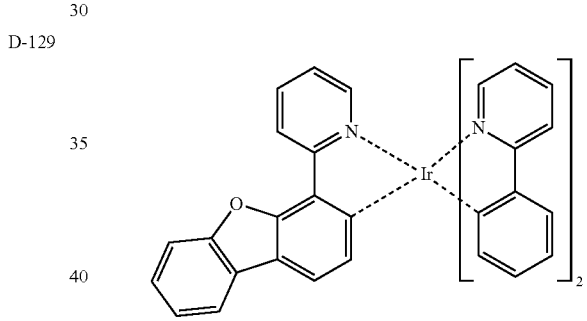
D-130 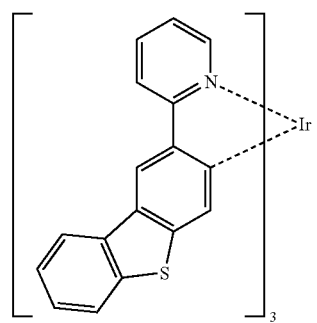
D-135 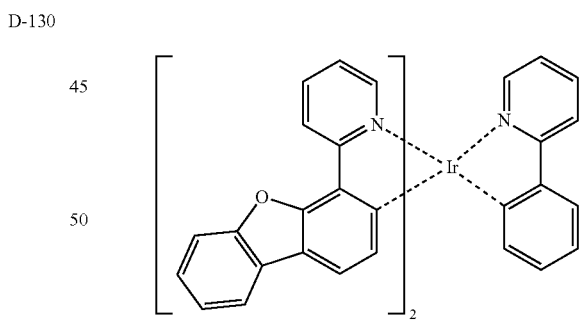
D-131 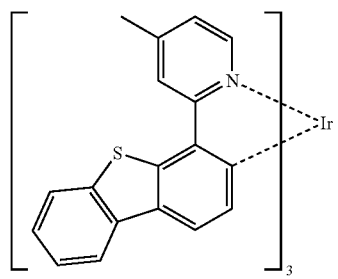
D-136 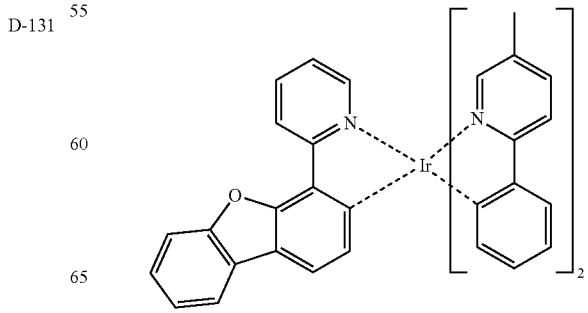

D-137
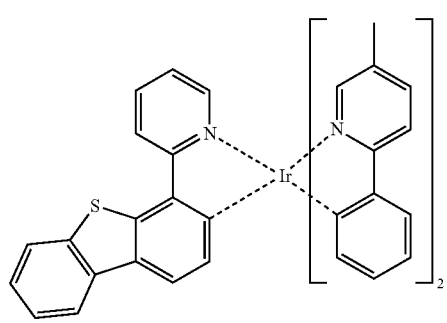
D-138
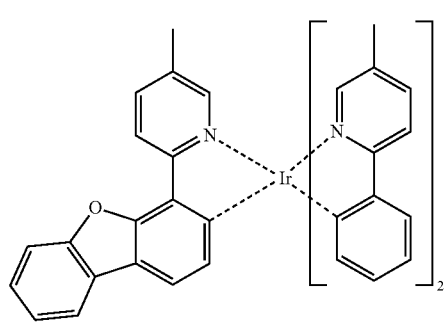
D-139
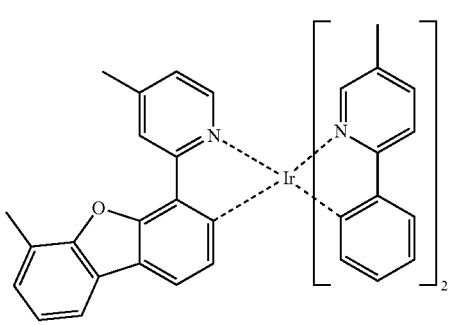
D-140
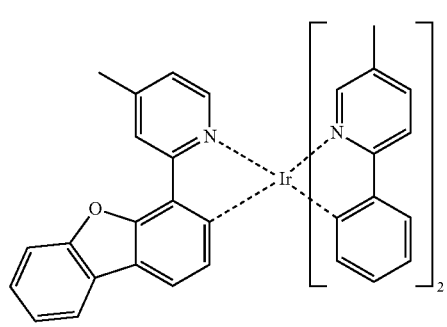
D-141
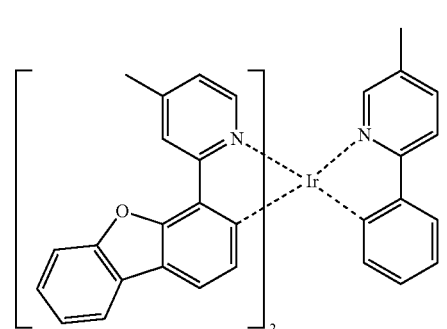
D-142
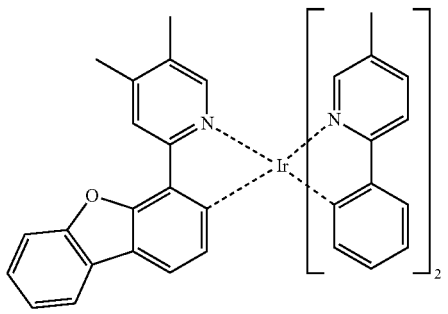
D-143
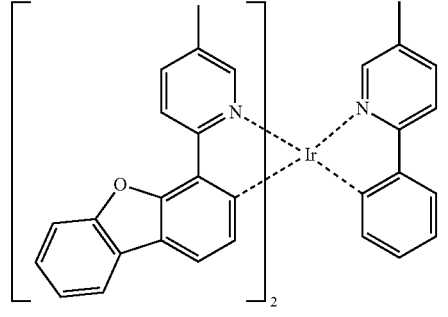
D-144
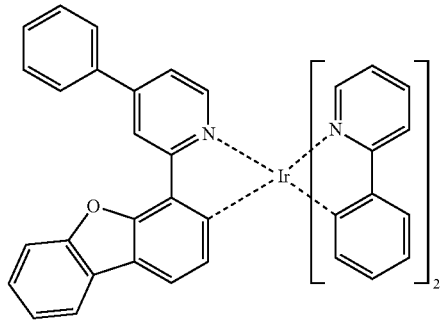
D-145
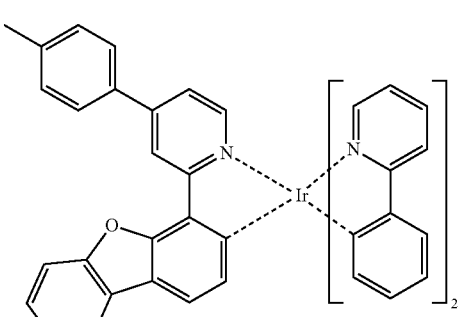
D-146
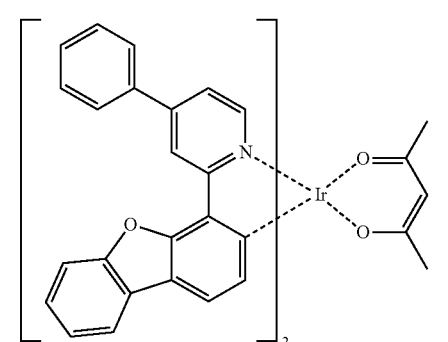

-continued
D-147
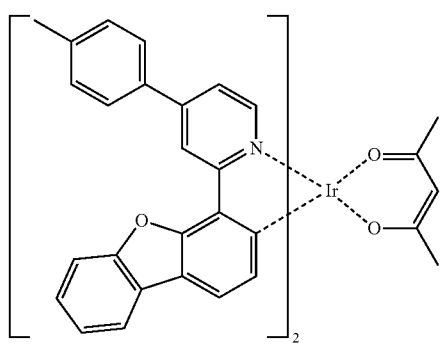
D-148
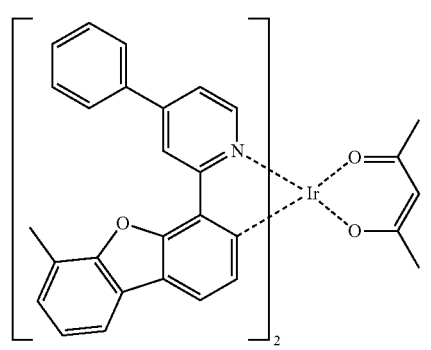
D-149
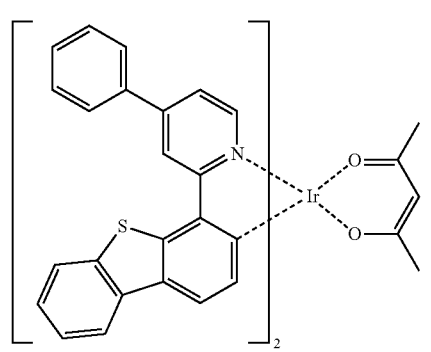
D-150
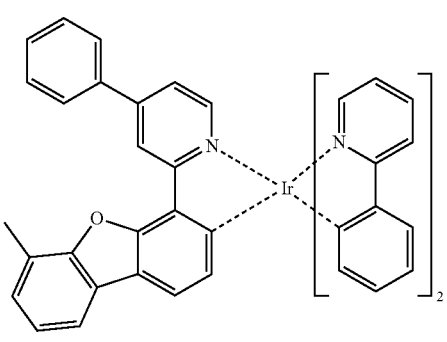
-continued
D-151
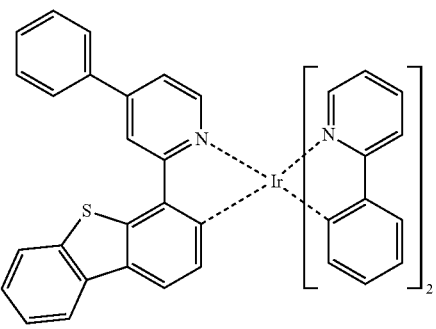
D-152
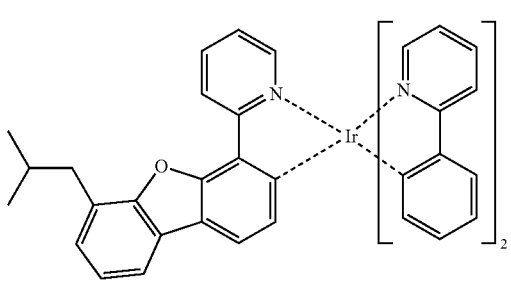
D-153
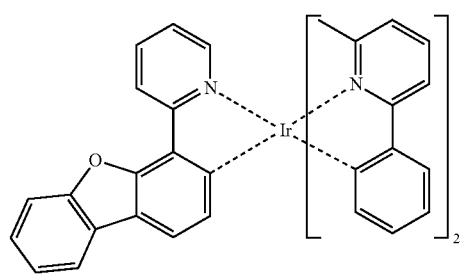
D-154
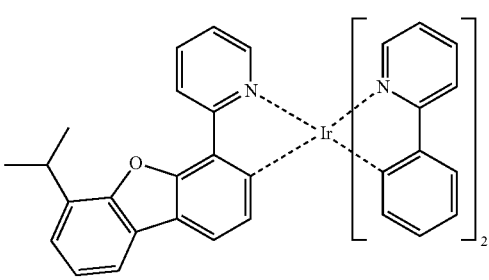
D-155
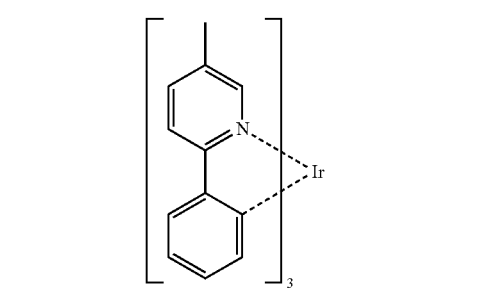

D-156
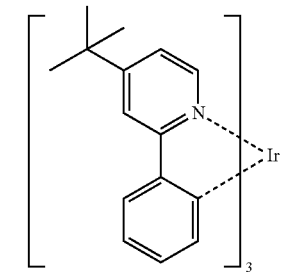
D-157
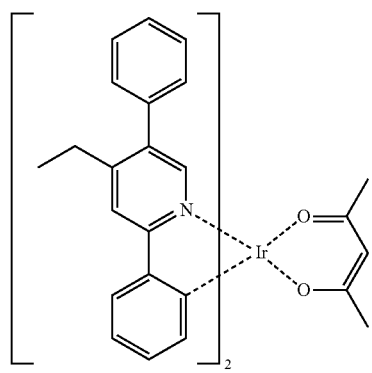
D-158
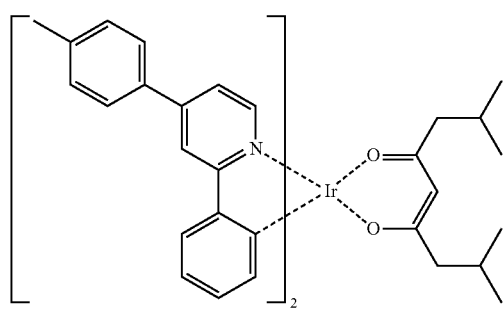
D-159
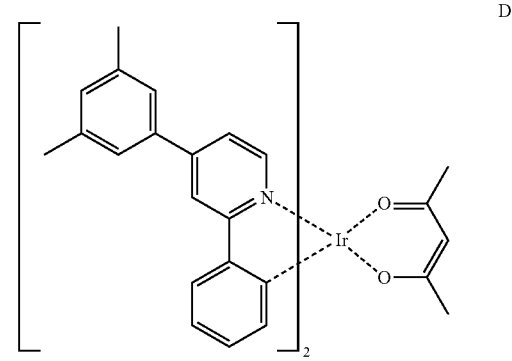
D-160
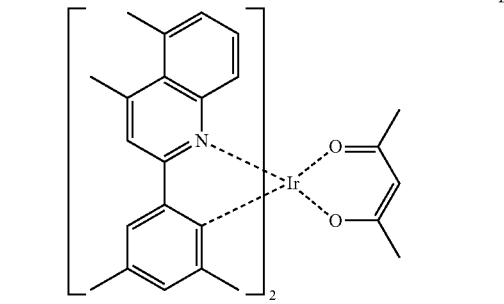
D-161
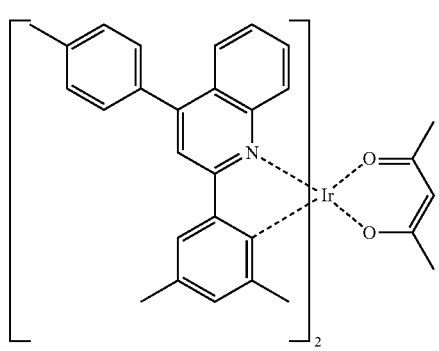
D-162
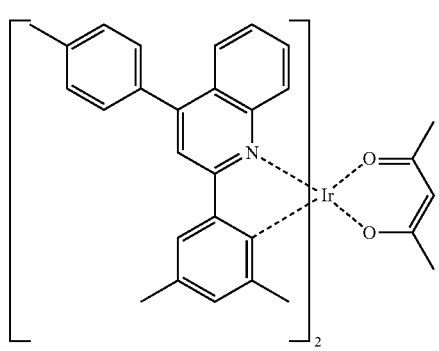
D-163
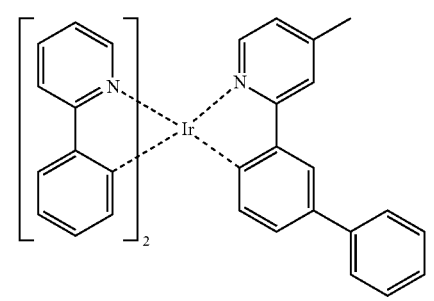
D-164
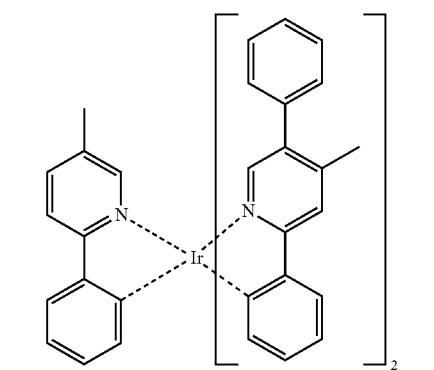

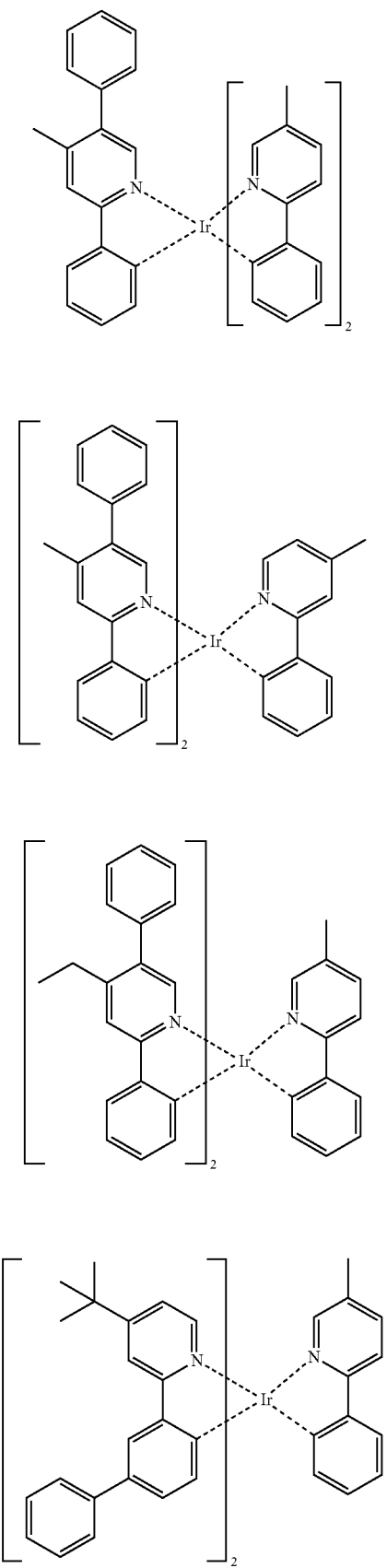
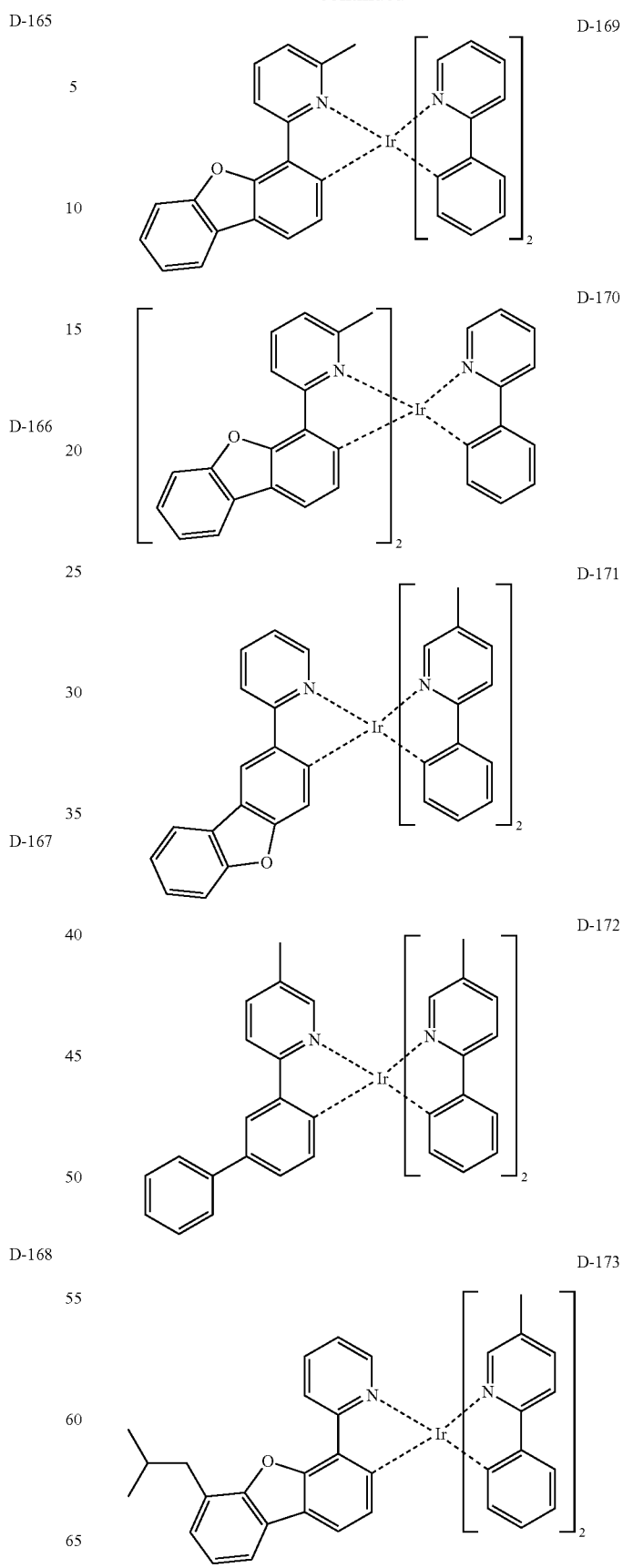

D-174
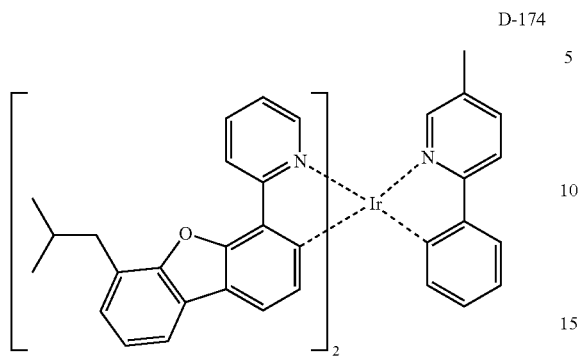
D-178
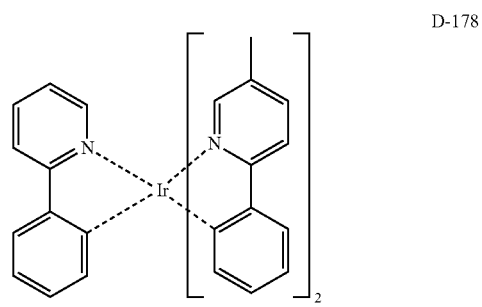
D-175
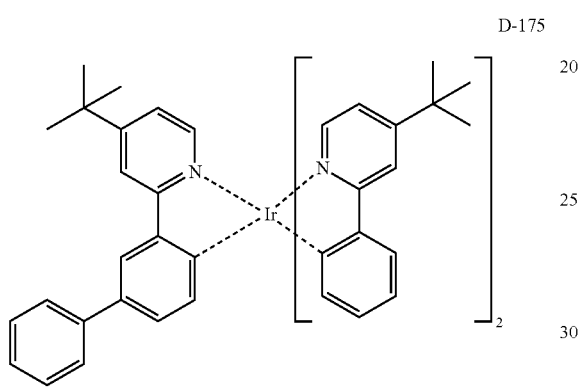
D-179
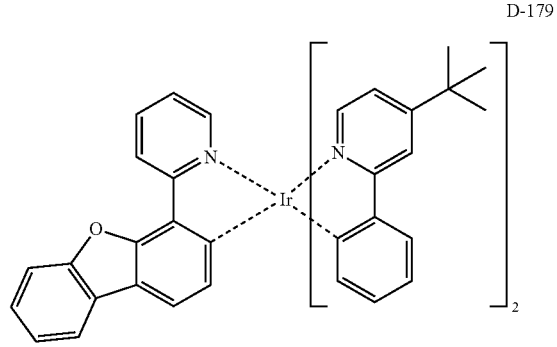
D-176
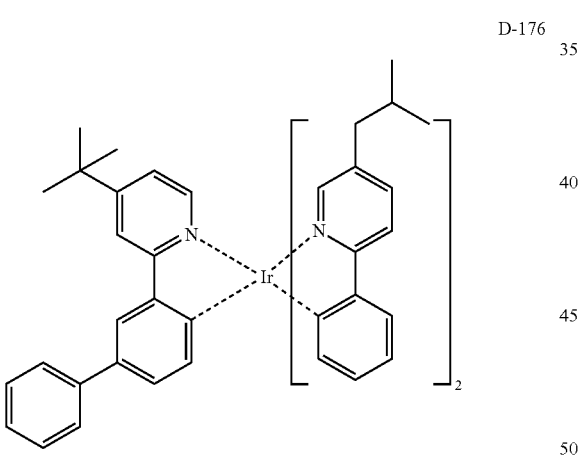
D-180
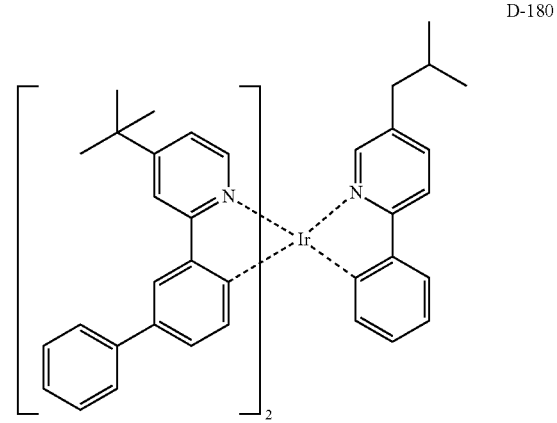
D-177
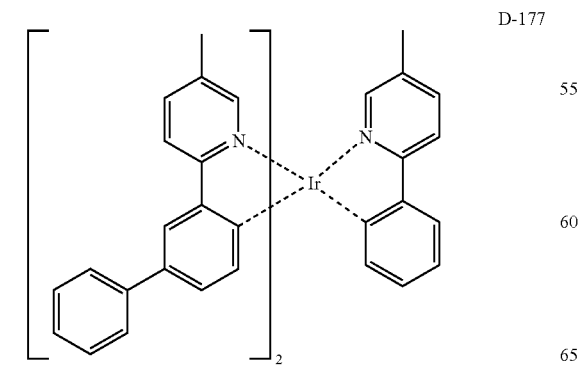
D-181
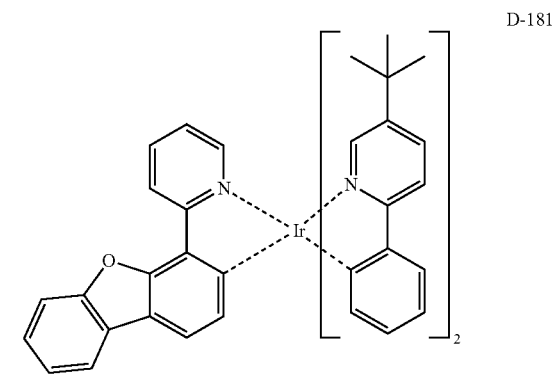

-continued
D-182
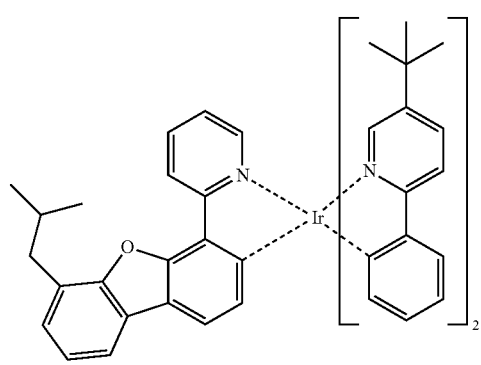
D-183
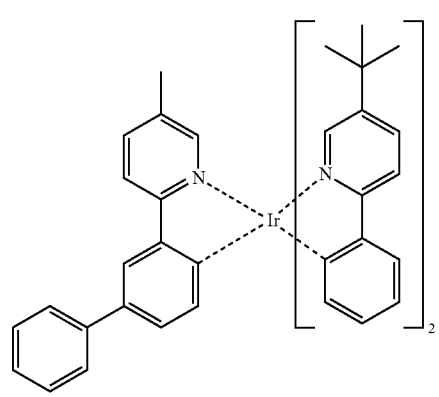
D-184
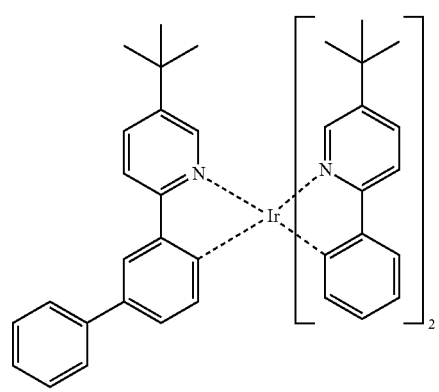
D-185
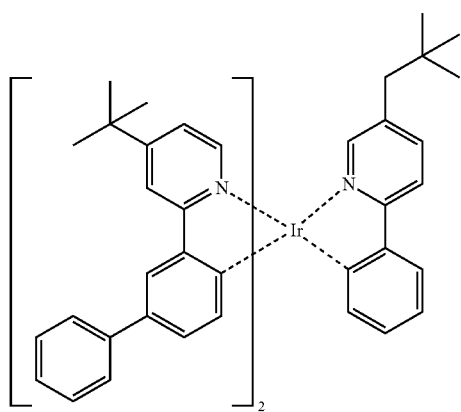
-continued
D-186
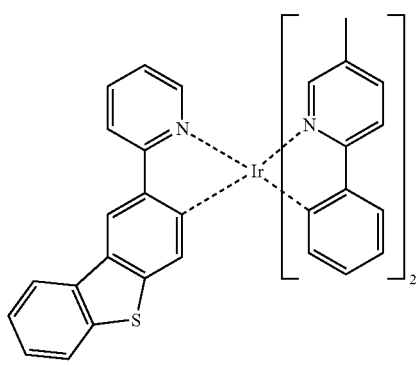
D-187
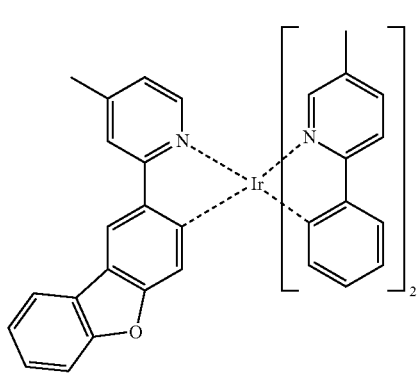
D-188
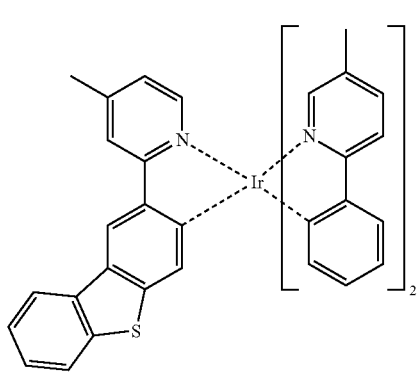
D-189
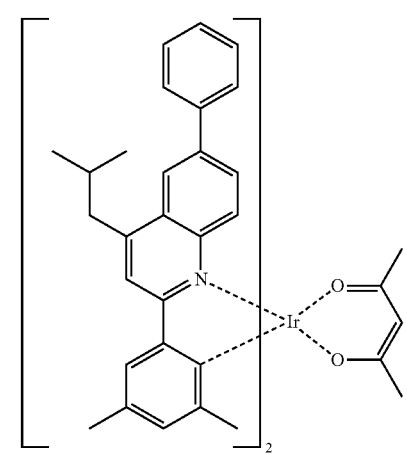

D-190
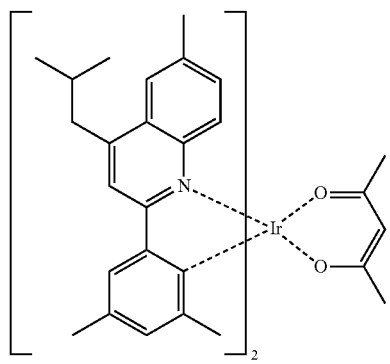
D-194
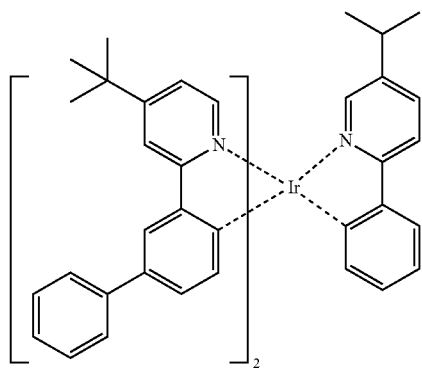
D-191
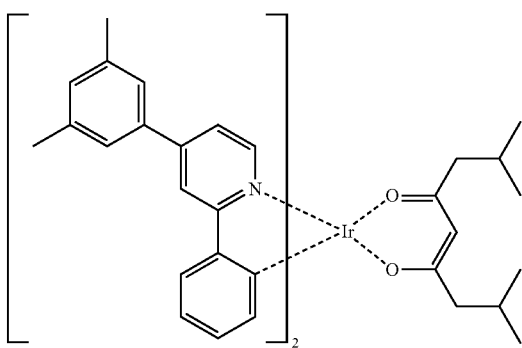
D-195
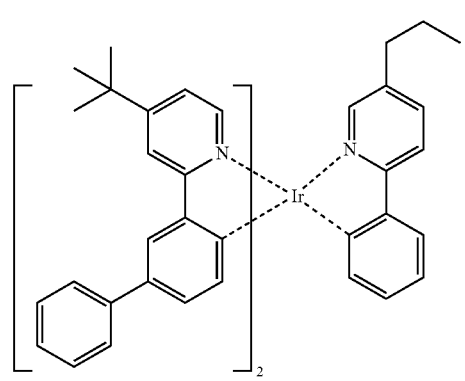
D-192
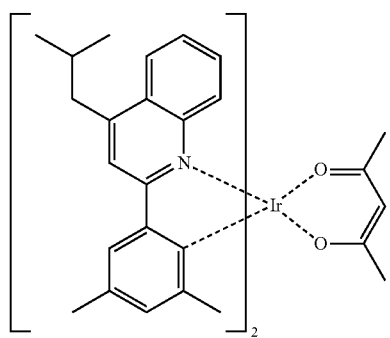
D-196
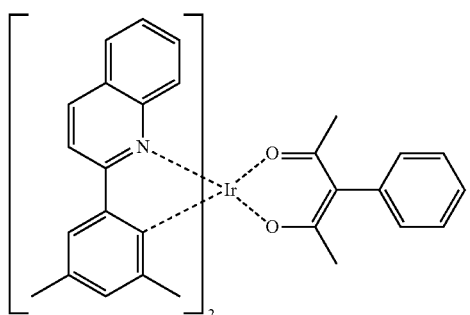
D-193
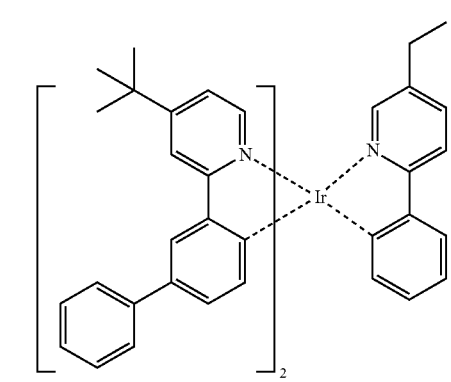
D-197
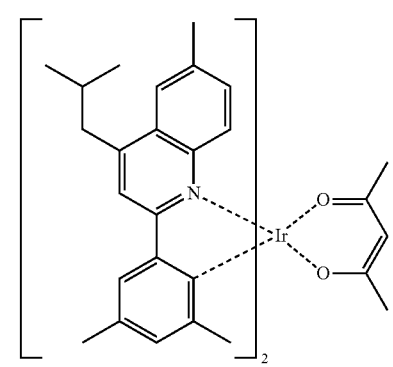

D-198

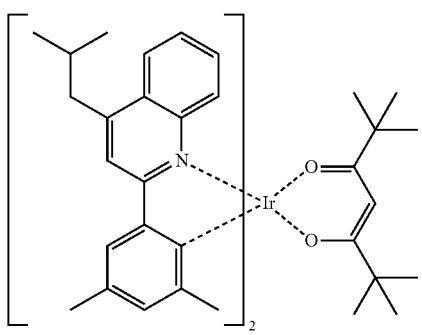

The organic electroluminescent device according to the present invention may comprise a first electrode, a second electrode, and at least one organic layer between the first and second electrodes, wherein the organic layer comprises the materials for an organic electroluminescent device of the present invention.

The organic electroluminescent device of the present invention comprises the organic electroluminescent compound of formula I in an organic layer and may further include at least one compound selected from the group consisting of arylamine-based compounds and styrylarylamine-based compounds in the organic layer.

In the organic electroluminescent device of the present invention, an organic layer may further comprise at least one metal selected from the group consisting of metals of Group 1, metals of Group 2, transition metals of the $4^{th}$ period, transition metals of the $5^{th}$ period, lanthanides, and organic metals of d-transition elements of the Periodic Table, or at least one complex compound comprising the metal; or may further comprise at least one of a light-emitting layer and a charge generating layer.

In addition, the organic electroluminescent device of the present invention may emit white light by further comprising at least one light-emitting layer which comprises a blue light-emitting compound, a red light-emitting compound, or a green light-emitting compound which is known in the art, in addition to the compound of the present invention; and may further include a yellow or orange light-emitting layer, if necessary.

Preferably, in the organic electroluminescent device of the present invention, at least one layer (hereinafter, "a surface layer") selected from a chalcogenide layer, a metal halide layer, and a metal oxide layer may be placed on an inner surface(s) of one or both electrode(s). Specifically, it is preferred that a chalcogenide (including oxides) layer of silicon or aluminum is placed on an anode surface of a light-emitting medium layer, and a metal halide layer or metal oxide layer is placed on a cathode surface of an electroluminescent medium layer. The surface layer provides operating stability for the organic electroluminescent device. Preferably, the chalcogenide includes $SiO_x(1 \leq X \leq 2)$, $AlO_x(1 \leq X \leq 1.5)$, SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

Furthermore, preferably, in the organic electroluminescent device of the present invention, a mixed region of an electron transport compound and a reductive dopant, or a mixed region of a hole transport compound and an oxidative dopant may be placed on at least one surface of a pair of electrodes. In this case, an electron transport compound is reduced to an anion, and thus it becomes easier to inject and transport electrons from the mixed region to a light-emitting medium. Furthermore, a hole transport compound is oxidized to a cation, and thus it becomes easier to inject and transport holes from the mixed region to a light-emitting medium. Preferably, an oxidative dopant includes various Lewis acids and acceptor compounds; and a reductive dopant includes alkali metals, alkali metal compounds, alkaline earth metals, rare-earth metals, and mixtures thereof. A reductive dopant layer may be employed as a charge generating layer to prepare an organic electroluminescent device having two or more light-emitting layers and emitting white light.

In order to form each layer constituting the organic electroluminescent device of the present invention, dry film-forming methods, such as vacuum deposition, sputtering, plasma, ion plating methods, etc., or wet film-forming methods, such as spin coating, dip coating, flow coating methods, etc., can be used.

When using a wet film-forming method, a thin film is formed by dissolving or dispersing materials constituting each layer in suitable solvents, such as ethanol, chloroform, tetrahydrofuran, dioxane, etc. The solvents are not specifically limited as long as the materials constituting each layer is soluble or dispersible in the solvents, which do not cause any problems in forming a layer.

Hereinafter, the organic electroluminescent compounds of the present invention, the preparation method thereof, and the properties of devices comprising the compounds will be explained in detail with reference to the representative compounds of the present invention.

EXAMPLE 1: PREPARATION OF COMPOUND A-27

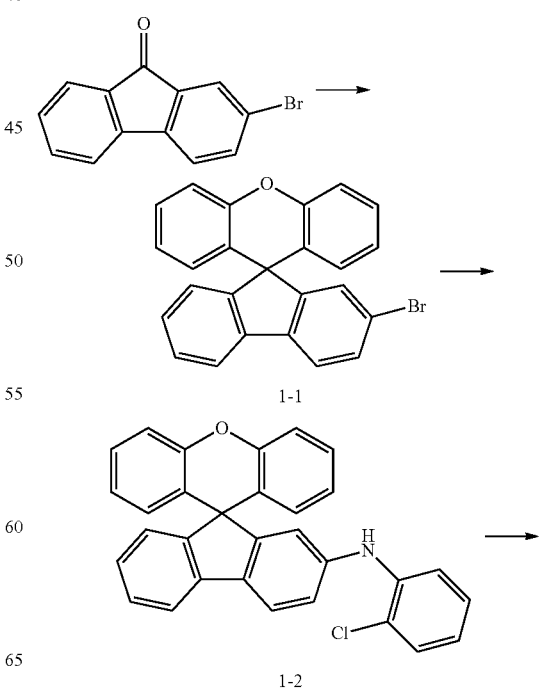

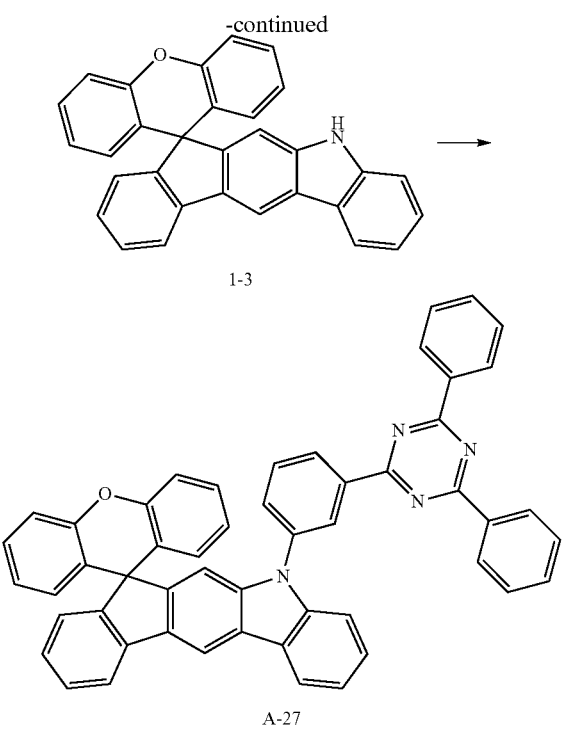

Preparation of Compound 1-1

2-Bromofluorene (30.0 g, 115.0 mmol), phenol (109.0 g, 1157.0 mmol), and methanesulfonic acid (30.0 mL) in a reaction vessel were stirred under reflux for 20 hrs. Upon completing the reaction, the mixture was washed with distilled water and the organic layer was extracted with methylene chloride (MC). After drying the extracted organic layer with MgSO$_4$, the solvent was removed by using a rotary evaporator. Thereafter, the obtained product was purified through column chromatography to obtain compound 1-1 (33.6 g, 71%).

Preparation of Compound 1-2

Compound 1-1 (25.0 g, 60.7 mmol), 2-chloroaniline (11.4 g, 91.1 mmol), palladium acetate (0.54 g, 2.43 mmol), tri-tert-butylphosphine (2.4 mL, 4.86 mmol), sodium tert-butoxide (14.6 g, 151.9 mmol), and toluene (180.0 mL) in a reaction vessel were stirred under reflux for 5 hrs. Upon completing the reaction, the mixture was washed with distilled water and the organic layer was extracted with MC. After drying the extracted organic layer with MgSO$_4$, the solvent was removed by using a rotary evaporator. Thereafter, the obtained product was purified through column chromatography to obtain compound 1-2 (16.6 g, 60%).

Preparation of Compound 1-3

Compound 1-2 (16.6 g, 36.2 mmol), palladium acetate (0.81 g, 3.62 mmol), tricyclohexyl phosphonium tetrafluoroborate (2.6 g, 7.24 mmol), cesium carbonate (35.4 g, 108.7 mmol), and dimethylacetamide (200.0 mL) in a reaction vessel were stirred under reflux for 4 hrs. Upon completing the reaction, the mixture was washed with distilled water and the organic layer was extracted with MC. After drying the extracted organic layer with MgSO$_4$, the solvent was removed by using a rotary evaporator. Thereafter, the obtained product was purified through column chromatography to obtain compound 1-3 (11.8 g, 78%).

Preparation of Compound A-27

Compound 1-3 (7.0 g, 16.6 mmol), 2-(3-bromophenyl)-4,6-diphenyl-1,3,5-triazine (7.7 g, 19.9 mmol), palladium acetate (0.37 g, 1.66 mmol), S-phos (1.3 g, 3.32 mmol), sodium tert-butoxide (4.7 g, 49.8 mmol), and xylene (90.0 mL) in a reaction vessel were stirred under reflux for 5 hrs. Upon completing the reaction, the mixture was washed with distilled water and the organic layer was extracted with MC. After drying the extracted organic layer with MgSO$_4$, the solvent was removed by using a rotary evaporator. Thereafter, the obtained product was purified through column chromatography to obtain compound A-27 (9.0 g, 75%).

TABLE 1

|      | MW     | UV     | PL     | M.P    |
|------|--------|--------|--------|--------|
| A-27 | 728.84 | 344 nm | 455 nm | 257° C. |

COMPARATIVE EXAMPLE 1: PRODUCTION OF A BLUE LIGHT-EMITTING ORGANIC ELECTROLUMINESCENT DEVICE WHICH DOES NOT COMPRISE AN ELECTRON BUFFER LAYER

An OLED device was produced as follows: A transparent electrode indium tin oxide (ITO) thin film (15 Ω/sq) on a glass substrate for an OLED device (GEOMATEC CO., LTD., Japan) was subjected to an ultrasonic washing by sequentially using acetone, ethanol, and distilled water, and was then stored in isopropanol. Next, the ITO substrate was mounted on a substrate holder of a vacuum vapor depositing apparatus. N$^4$,N$^{4'}$-diphenyl-N$^4$,N$^{4'}$-bis(9-pnenyl-9H-carbazol-3-yl)-[1,1'-biphenyl]-4,4'-diamine was introduced into a cell of the vacuum vapor depositing apparatus, and the pressure in the chamber of the apparatus was then controlled to 10$^{-6}$ torr. Thereafter, an electric current was applied to the cell to evaporate the introduced material, thereby forming the first hole injection layer having a thickness of 60 nm on the ITO substrate. 1,4,5,8,9,12-hexaazatriphenylene-hexacarbonitrile (HAT-CN) was then introduced into another cell of the vacuum vapor depositing apparatus, and an electric current was applied to the cell to evaporate the introduced material, thereby forming the second hole injection layer having a thickness of 5 nm on the first hole injection layer. N-([1,1'-biphenyl]-4-yl)-9,9-dimethyl-N-(4-(9-phenyl-9H-carbazol-3-yl)phenyl)-9H-fluorene-2-amine was introduced into another cell of the vacuum vapor depositing apparatus. Thereafter, an electric current was applied to the cell to evaporate the introduced material, thereby forming the first hole transport layer having a thickness of 20 nm on the second hole injection layer. Compound HT-2 was then introduced into another cell of the vacuum vapor depositing apparatus, and an electric current was applied to the cell to evaporate the introduced material, thereby forming the second hole transport layer having a thickness of 5 nm on the first hole transport layer. After forming the hole injection layers and the hole transport layers, a light-emitting layer was then deposited as follows. Compound BH-1 as a host was introduced into one cell of the vacuum vapor depositing apparatus and compound BD-1 as a dopant was introduced into another cell of the apparatus. The two materials were evaporated at a different rate and the dopant was deposited in a doping amount of 2 wt %, based on the total weight of the host and dopant, to form a light-emitting layer having a thickness of 20 nm on the second hole transport layer. Next, 2-(4-(9,10-di(naphthalene-2-yl)anthracene-2-yl)phenyl)-1-phenyl-1H-benzo[d]imidazole as an electron transport material was introduced into one cell of the vacuum vapor depositing apparatus and lithium quinolate was introduced into another cell of the vacuum vapor depositing apparatus. The two materials were evaporated at the same rate and doped in a doping amount of 50 wt %, respectively, to form an electron transport layer having a thickness of 35 nm on the light-emitting layer. After depositing lithium quinolate having a thickness of 2 nm as an electron injection layer on the electron transport layer, an Al cathode having a thickness of 80 nm was then deposited by another vacuum vapor deposition apparatus on the electron injection layer. Thus, an OLED device was produced. All the materials used for producing the OLED device were purified by vacuum sublimation at $10^{-6}$ torr prior to use.

The driving voltage at the luminance of 1,000 nit, the luminous efficiency, the CIE color coordinate, and the time taken for the light-emission to be reduced from 100% to 90% at the luminance of 2,000 nit (T90 lifespan) of the OLED device produced as above are provided in Table 2 below.

HT-2

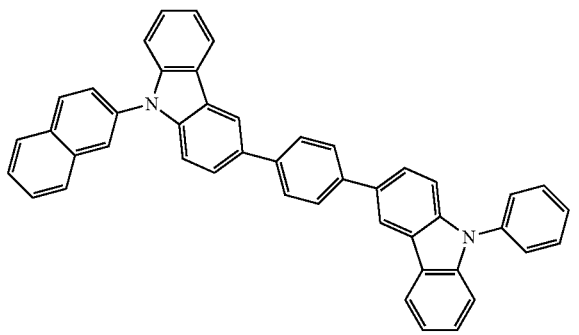

BH-1

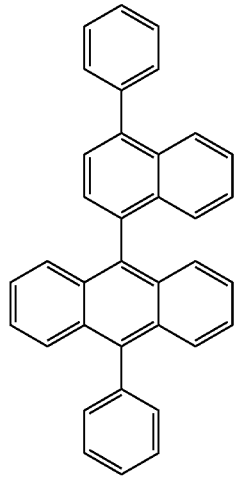

BD-1

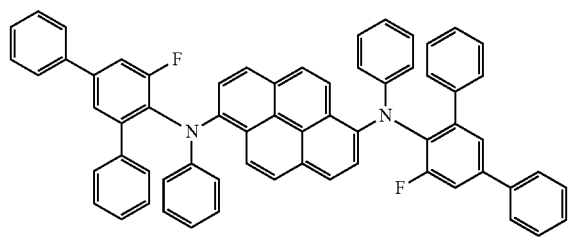

DEVICE EXAMPLE 1: PRODUCTION OF A BLUE LIGHT-EMITTING ORGANIC ELECTROLUMINESCENT DEVICE ACCORDING TO THE PRESENT INVENTION

An OLED device was produced in the same manner as in Comparative Example 1, except that the thickness of an electron transport layer was reduced to 30 nm, and an electron buffer layer comprising compound A-27 and having a thickness of 5 nm was inserted between the light-emitting layer and the electron transport layer. Evaluation results of the OLED device produced in Device Example 1 are provided in Table 2 below.

DEVICE EXAMPLE 2: PRODUCTION OF A BLUE LIGHT-EMITTING ORGANIC ELECTROLUMINESCENT DEVICE ACCORDING TO THE PRESENT INVENTION

An OLED device was produced in the same manner as in Device Example 1, except that the electron buffer layer was changed to one comprising compound A-133. Evaluation results of the OLED device produced in Device Example 2 are provided in Table 2 below.

TABLE 2

| | Electron Buffer Layer | Driving Voltage (V) | Luminous Efficiency (cd/A) | Color Coordinate (x) | Color Coordinate (y) | T90 Lifespan (hr) |
|---|---|---|---|---|---|---|
| Comparative Example 1 | — | 4.5 | 6.1 | 140 | 94 | 41.3 |
| Device Example 1 | A-27 | 4.4 | 6.9 | 139 | 92 | 46.2 |
| Device Example 2 | A-133 | 4.4 | 6.8 | 139 | 91 | 47.5 |

From Table 2 above, the electron buffer layer of the present invention has fast electron current property, and thus Device Examples 1 and 2 provide high efficiency and long lifespan compared with Comparative Example 1 having no electron buffer layer.

The electron buffer layer can improve the problem that when organic electroluminescent materials are exposed to a high temperature in the process of the manufacture of panels, the current properties of the device may be changed in the devices thereby changing the light-emitting luminance. In order to secure stability at the exposure to a high temperature while having similar current properties compared to those of a device without an electron buffer layer, the properties of compounds included in the electron buffer layer are important. The compound of formula 1 has the structure in which a benzene ring of fluorene in the spiro[fluorene-9,9'-xanthene] backbone is fused to benzofuran, benzothiophene, or indole. In particular, each of the fluorene and the xanthene derivative in the spiro[fluorene-9,9'-xanthene] forms a planar structure, thereby forming a tetrasubstituted structure based on the center of a spiro structure, and thus the dihedral angle of the two planes is almost 90° which provides a rectangular form. This effectively modulates π-π stacking interactions via the steric hindrance effect. That is, the compound of formula 1 has excellent morphological stability, and thus has Tg (glass transition temperature) of 172° C. which provides very high thermal stability. In this connection, a non-patent literature specifically describes the thermal and oxidation stability of the spiro derivatives (see Macromol. Rapid Commun. 2009, 30, 1745-1750). Furthermore, oxygen as a hetero atom linking to two phenyl rings increases the properties of charge injection and transport, and thus can contribute to fast electron current properties. This may be found in a non-patent literature (see D. Vak et al., Journal of Luminescence, 115 (2005) 109-116). Thus, the compound according to the present invention can greatly contribute to lower driving voltage and improve the lifespan of an organic electroluminescent device. The improvement of properties of devices also has a great effect on guaranteeing stability upon exposure to a high temperature in the process of the manufacture of panels and on improving performance.

In an organic electroluminescent device comprising a first electrode, a second electrode, and a light-emitting layer, electron injection can be controlled by the electron affinity LUMO energy value of an electron buffer layer, by disposing the electron buffer layer between the light-emitting layer and the second electrode.

LUMO (lowest unoccupied molecular orbital) energy value and HOMO (highest occupied molecular orbital) energy value have inherently negative numbers, but the LUMO energy value and the HOMO energy value in the present invention are conveniently expressed as their absolute values. Furthermore, the comparison between LUMO energy values is based on their absolute values. The LUMO energy value and the HOMO energy value in the present invention are calculated by Density Functional Theory (DFT).

In the organic electroluminescent device of the present invention, the LUMO energy value of the electron buffer layer may be larger than the LUMO energy value of the host compounds. A difference between the LUMO energy values of the electron buffer layer and the host compounds may be equal to or less than 0.3 eV. For example, the LUMO energy values of the electron buffer layer and the host compounds may be 1.9 eV and 1.6 eV, respectively. Thus, the difference between the LUMO energy values of the electron buffer layer and the host compounds may be 0.3 eV. The LUMO barrier between the electron buffer layer and the host compounds may be a factor to increase driving voltage. However, since the electron buffer layer comprises the compound of formula 1, it is easier to transport electrons to the host compound compared with other compounds than the compound of formula 1. Therefore, the organic electroluminescent device of the present invention has low driving voltage, high luminous efficiency, and long driving lifespan. In the present invention, the LUMO energy value of the electron buffer layer corresponds to the LUMO energy value of the compound of formula 1 included in the electron buffer layer.

In the organic electroluminescent device of the present invention, an electron transport zone indicates a zone which transports electrons from a second electrode to a light-emitting layer. The electron transport zone may comprise an electron transport compound, a reducing dopant, or the combination thereof. The electron transport compound may be at least one selected from the group consisting of oxazole-, isoxazole-, triazole-, isothiazole-, oxadiazole-, thiadiazole-, perylene-, and anthracene-based compounds, aluminum complexes, and gallium complexes. The reducing dopant may be at least one selected from the group consisting of an alkaline metal, an alkaline metal compound, an alkaline earth metal, a rare-earth metal, a halide thereof, an oxide thereof, and a complex thereof. The electron transport zone may further comprise an electron transport layer, an electron injection layer, or both of them. Each of the electron transport layer and the electron injection layer may be comprised of two or more layers. The LUMO energy value of an electron buffer layer may be smaller or larger than the LUMO energy value of an electron transport zone. For example, the LUMO energy values of the electron buffer layer and the electron transport zone may be 1.9 eV and 1.8 eV, respectively. Thus, the difference between the LUMO energy values of the layer and the zone may be 0.1 eV. Since the electron buffer layer has the LUMO energy value as recited above, it is easy to inject electrons to a light-emitting layer through the electron buffer layer. The LUMO energy value of the electron transport zone may be 1.7 eV or higher, or 1.9 eV or higher.

Specifically, the LUMO energy level of the electron buffer layer may be higher than the LUMO energy levels of the host compound and the electron transport zone. For example, the LUMO energy levels may have the following relationship: the electron buffer layer>the electron transport zone>the host compound. In view of the relationship of the LUMO levels of the respective layers, electrons are restricted between the light-emitting layer and the electron buffer layer, and electron injection is inhibited, and thus the driving voltage can be increased. However, an electron buffer layer comprising the compound of formula 1 easily transports electrons to a light-emitting layer, and thus the organic electroluminescent device of the present invention can have low driving voltage, high luminous efficiency, and long driving lifespan.

LUMO energy values can be easily determined by using various known methods. Conventionally, LUMO energy levels can be determined by using cyclic voltammetry or ultraviolet photoelectron spectroscopy (UPS). Thus, one skilled in the art can easily recognize an electron buffer layer, a host material, and an electron transport zone which satisfy the relationship of the LUMO energy levels of the present invention and practice the present invention. HOMO energy levels can also be easily determined in the same manner as used for the LUMO energy levels.

DEVICE EXAMPLE 3: PRODUCTION OF AN OLED DEVICE BY USING AN ORGANIC ELECTROLUMINESCENT COMPOUND ACCORDING TO THE PRESENT INVENTION

An OLED device by using an organic electroluminescent compound according to the present invention was produced as follows: A transparent electrode indium tin oxide (ITO) thin film (15 Ω/sq) on a glass substrate for an OLED device (GEOMATEC CO., LTD., Japan) was subjected to an ultrasonic washing by sequentially using trichloroethylene, acetone, ethanol, and distilled water, and was then stored in isopropanol. Next, the ITO substrate was mounted on a substrate holder of a vacuum vapor depositing apparatus. $N^4,N^{4'}$-diphenyl-$N^4,N^{4'}$-bis(9-phenyl-9H-carbazol-3-yl)-[1,1'-biphenyl]-4,4'-diamine was introduced into a cell of the vacuum vapor depositing apparatus, and the pressure in the chamber of the apparatus was then controlled to $10^{-6}$ torr. Thereafter, an electric current was applied to the cell to evaporate the introduced material, thereby forming the first hole injection layer having a thickness of 80 nm on the ITO substrate. 1,4,5,8,9,12-hexaazatriphenylene-hexacarbonitrile was then introduced into another cell of the vacuum vapor depositing apparatus, and an electric current was applied to the cell to evaporate the introduced material, thereby forming the second hole injection layer having a thickness of 3 nm on the first hole injection layer. N-([1,1'-biphenyl]-4-yl)-9,9-dimethyl-N-(4-(9-phenyl-9H-carbazol-3-yl)phenyl)-9H-fluoren-2-amine was introduced into another cell of the vacuum vapor depositing apparatus.

Thereafter, an electric current was applied to the cell to evaporate the introduced material, thereby forming a hole transport layer having a thickness of 40 nm on the second hole injection layer. After forming the hole injection layers and the hole transport layer, a light-emitting layer was then deposited as follows. Compound A-27 as a host was introduced into one cell of the vacuum vapor depositing apparatus and compound D-1 as a dopant was introduced into another cell of the apparatus. The two materials were evaporated at a different rate and the dopant was deposited in a doping amount of 15 wt %, based on the total weight of the host and dopant, to form a light-emitting layer having a thickness of 40 nm on the hole transport layer. Next, 2,4-bis(9,9-dimethyl-9H-fluorene-2-yl)-6-(naphthalene-2-yl)-1,3,5-triazine and lithium quinolate were evaporated at the rate of 4:6 on another two cells of the vacuum vapor depositing apparatus to form an electron transport layer having a thickness of 35 nm on the light-emitting layer. After depositing lithium quinolate having a thickness of 2 nm as an electron injection layer on the electron transport layer, an Al cathode having a thickness of 80 nm was then deposited by another vacuum vapor deposition apparatus on the electron injection layer. Thus, an OLED device was produced. All the materials used for producing the OLED device were purified by vacuum sublimation at $10^{-6}$ torr prior to use.

The produced OLED device showed green emission and had a current density of 2.66 mA/cm$^2$ and a luminance of 1350 cd/m$^2$ at 2.7 V.

COMPARATIVE EXAMPLE 2: PRODUCTION OF AN OLED DEVICE BY USING CONVENTIONAL ORGANIC ELECTROLUMINESCENT COMPOUND

An OLED device was produced in the same manner as in Device Example 2, except that compound B-1 was used as a host and compound D-1 was used as a dopant in the light-emitting material, thereby depositing a light-emitting layer having a thickness of 40 nm on the hole transport layer.

The produced OLED device showed green emission and had a current density of 2.59 mA/cm$^2$ and a luminance of 1060 cd/m$^2$ at 4.8 V.

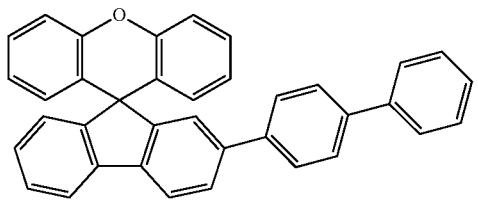

B-1

COMPARATIVE EXAMPLE 3: PRODUCTION OF AN OLED DEVICE BY USING CONVENTIONAL ORGANIC ELECTROLUMINESCENT COMPOUND

An OLED device was produced in the same manner as in Device Example 2, except that 4,4'-N,N'-dicarbazol-biphenyl was used as a host and compound D-1 was used as a dopant in the light-emitting material, thereby depositing a light-emitting layer having a thickness of 40 nm on the hole transport layer; aluminum(III) bis(2-methyl-8-quinolinato)-4-phenyl phenolate as a hole blocking layer having a thickness of 10 nm was deposited; and 2,4-bis(9,9-dimethyl-9H-fluorene-2-yl)-6-(naphthalene-2-yl)-1,3,5-triazine and lithium quinolate were evaporated at the rate of 4:6 on another two cells to form an electron transport layer having a thickness of 25 nm on the hole blocking layer.

The produced OLED device showed green emission and had a current density of 4.18 mA/cm$^2$ and a luminance of 1890 cd/m$^2$ at 5.6 V.

COMPARATIVE EXAMPLE 4: PRODUCTION OF AN OLED DEVICE BY USING CONVENTIONAL ORGANIC ELECTROLUMINESCENT COMPOUND

An OLED device was produced in the same manner as in Device Example 2, except that compound B-2 was used as a host and compound D-1 was used as a dopant in the light-emitting material, thereby depositing a light-emitting layer having a thickness of 40 nm on the hole transport layer.

The produced OLED device showed green emission and had a current density of 2.39 mA/cm$^2$ and a luminance of 1040 cd/m$^2$ at 3.0 V.

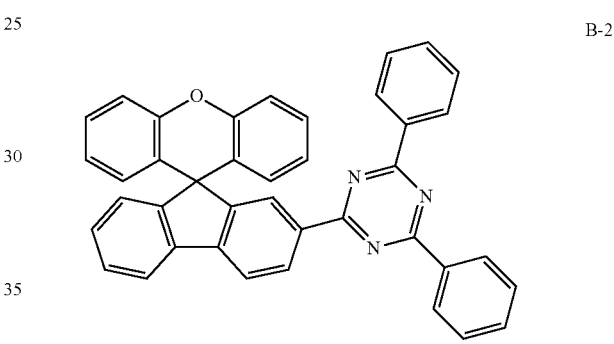

B-2

From the above, it can be seen that the organic electroluminescent compound of the present invention has better luminous property than that of conventional materials. Furthermore, the device using the organic electroluminescent compound of the present invention as a host material has excellent luminous property and reduces the driving voltage, thereby increasing the power efficiency and improving the consumption of electric power.

COMPARATIVE EXAMPLE 5: PRODUCTION OF AN OLED DEVICE BY USING CONVENTIONAL ORGANIC ELECTROLUMINESCENT COMPOUND

An OLED device was produced as follows: A transparent electrode indium tin oxide (ITO) thin film (15 Ω/sq) on a glass substrate for an OLED device (GEOMATEC CO., LTD., Japan) was subjected to an ultrasonic washing by sequentially using acetone, ethanol, and distilled water, and was then stored in isopropanol. Next, the ITO substrate was mounted on a substrate holder of a vacuum vapor depositing apparatus. N$^4$,N$^{4'}$-diphenyl-N$^4$,N$^{4'}$-bis(9-phenyl-9H-carbazol-3-yl)-[1,1'-biphenyl]-4,4'-diamine was introduced into a cell of the vacuum vapor depositing apparatus, and the pressure in the chamber of the apparatus was then controlled to $10^{-6}$ torr. Thereafter, an electric current was applied to the cell to evaporate the introduced material, thereby forming the first hole injection layer having a thickness of 60 nm on the ITO substrate. 1,4,5,8,9,12-hexaazatriphenylene-hexacarbonitrile was then introduced into another cell of the vacuum vapor depositing apparatus, and an electric current was applied to the cell to evaporate the introduced material, thereby forming the second hole injection layer having a thickness of 5 nm on the first hole injection layer. N-([1,1'-biphenyl]-4-yl)-9,9-dimethyl-N-(4-(9-phenyl-9H-carbazol-3-yl)phenyl)-9H-fluorene-2-amine was introduced into another cell of the vacuum vapor depositing apparatus. Thereafter, an electric current was applied to the cell to evaporate the introduced material, thereby forming the first hole transport layer having a thickness of 20 nm on the second hole injection layer. 9-(naphthalene-2-yl)-3-(4-(9-phenyl-9H-carbazol-3-yl)phenyl)-9H-carbazole was then introduced into another cell of the vacuum vapor depositing apparatus, and an electric current was applied to the cell to evaporate the introduced material, thereby forming the second hole transport layer having a thickness of 5 nm on the first hole transport layer. After forming the hole injection layers and the hole transport layers, a light-emitting layer was then deposited as follows. Compound BH-1 as a host was introduced into one cell of the vacuum vapor depositing apparatus and compound BD-1 as a dopant was introduced into another cell of the apparatus. The two materials were evaporated at a different rate and the dopant was deposited in a doping amount of 2 wt %, based on the total weight of the host and dopant, to form a light-emitting layer having a thickness of 20 nm on the second hole transport layer. Next, 2-(4-(9,10-di(naphthalene-2-Aanthracene-2-yl)phenyl)-1-phenyl-1H-benzo[d]imidazole (compound ETL-1) as an electron transport material was introduced into one cell of the vacuum vapor depositing apparatus to form an electron transport layer having a thickness of 35 nm on the light-emitting layer. After depositing lithium quinolate having a thickness of 2 nm as an electron injection layer on the electron transport layer, an Al cathode having a thickness of 80 nm was then deposited by another vacuum vapor deposition apparatus on the electron injection layer. Thus, an OLED device was produced. All the materials used for producing the OLED device were purified by vacuum sublimation at $10^{-6}$ torr prior to use.

DEVICE EXAMPLES 4 AND 5: PRODUCTION OF BLUE LIGHT-EMITTING ORGANIC ELECTROLUMINESCENT DEVICES ACCORDING TO THE PRESENT INVENTION

OLED devices were produced in the same manner as in Comparative Example 5, except that an electron transport material was changed as shown in Table 3 below. Evaluation results of the OLED devices produced in Comparative Example 5, and Device Examples 4 and 5 are provided in Table 3 below.

TABLE 3

| | Electron Transport Layer | Driving Voltage (V) | Luminous Efficiency (cd/A) | Color Coordinate (x) | Color Coordinate (y) |
|---|---|---|---|---|---|
| Comparative Example 5 | ETL-1 | 5.0 | 4.8 | 142 | 107 |
| Device Example 4 | A-27 | 5.1 | 7.2 | 139 | 93 |
| Device Example 5 | A-133 | 5.0 | 7.1 | 139 | 94 |

From Table 3 above, the electron transport layer of the present invention has fast electron current property, and thus Device Examples 4 and 5 provide high efficiency compared with Comparative Example 5.

The invention claimed is:

1. An organic electroluminescent compound represented by the following formula 1:

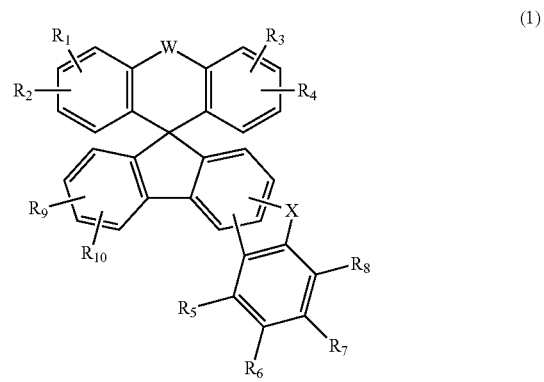

wherein
W represents O or S;
X represents O, S or $NR_{11}$;
$R_1$ to $R_{11}$ each independently represent hydrogen, deuterium, a halogen, a cyano group, a substituted or unsubstituted (C1-C30)alkyl group, a substituted or unsubstituted (C6-C30)aryl group, a substituted or unsubstituted 3- to 30-membered heteroaryl group, a substituted or unsubstituted (C3-C30)cycloalkyl group, a substituted or unsubstituted (C1-C30)alkoxy group, a substituted or unsubstituted tri(C1-C30)alkylsilyl group, a substituted or unsubstituted di(C1-C30)alkyl (C6-C30)arylsilyl group, a substituted or unsubstituted (C1-C30)alkyldi(C6-C30)arylsilyl group, a substituted or unsubstituted tri(C6-C30)arylsilyl group, a substituted or unsubstituted mono- or di-(C1-C30)alkylamino group, a substituted or unsubstituted mono- or di-(C6-C30)arylamino group, or a substituted or unsubstituted (C1-C30)alkyl(C6-C30)arylamino group; or are linked to an adjacent substituent(s) to form a substituted or unsubstituted mono- or polycyclic, (C3-C30) alicyclic or aromatic ring, whose carbon atom(s) may be replaced with at least one hetero atom selected from nitrogen, oxygen, and sulfur; and
the heteroaryl group contains at least one hetero atom selected from B, N, O, S, Si, and P.

2. The organic electroluminescent compound according to claim 1, wherein the substituents of the substituted alkyl group, the substituted aryl group, the substituted heteroaryl group, the substituted cycloalkyl group, the substituted alkoxy group, the substituted trialkylsilyl group, the substituted dialkylarylsilyl group, the substituted alkyldiarylsilyl group, the substituted triarylsilyl group, the substituted mono- or di-alkylamino group, the substituted mono- or di-arylamino group, the substituted alkylarylamino group, and the substituted mono- or polycyclic, alicyclic or aromatic ring in $R_1$ to $R_{11}$ each independently are at least one selected from the group consisting of deuterium, a halogen, a cyano, a carboxyl, a nitro, a hydroxyl, a (C1-C30)alkyl, a halo(C1-C30)alkyl, a (C1-C30)alkoxy, a (C1-C30)alkylthio, a (C3-C30)cycloalkyl, a 3- to 7-membered heterocycloalkyl, a (C6-C30)aryloxy, a (C6-C30)arylthio, a 3- to 30-membered heteroaryl unsubstituted or substituted with a (C6-C30)aryl, a (C6-C30)aryl unsubstituted or substituted with a 3- to 30-membered heteroaryl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl(C6-C30)aryl.

3. The organic electroluminescent compound according to claim 1, wherein

W represents O or S;

X represents O, S or $NR_{11}$;

$R_1$ to $R_{10}$ each independently represent hydrogen, or a substituted or unsubstituted (C6-C18)aryl group; or are linked to an adjacent substituent(s) to form a substituted or unsubstituted, mono- or polycyclic (C6-C20) alicyclic or aromatic ring; and $R_{11}$ represents a substituted or unsubstituted (C6-C18)aryl group, or a substituted or unsubstituted 5- to 20-membered heteroaryl group.

4. The organic electroluminescent compound according to claim 1, wherein

W represents O or S;

X represents O, S or $NR_{11}$;

$R_1$ to $R_{10}$ each independently represent hydrogen, or a (C6-C18)aryl unsubstituted or substituted with a (C6-C18)aryl group or a 5- to 20-membered heteroaryl group; or are linked to an adjacent substituent(s) to form a mono- or polycyclic (C6-C20) aromatic ring unsubstituted or substituted with a (C6-C12)aryl group; and $R_{11}$ represents a (C6-C18)aryl group which is unsubstituted or substituted with a (C6-C18)aryl group or a 5- to 20-membered heteroaryl group, or a 5- to 20-membered heteroaryl group which is unsubstituted or substituted with a (C6-C18)aryl group or a 5- to 20-membered heteroaryl group.

5. The organic electroluminescent compound according to claim 1, wherein the compound represented by formula 1 is selected from the group consisting of:

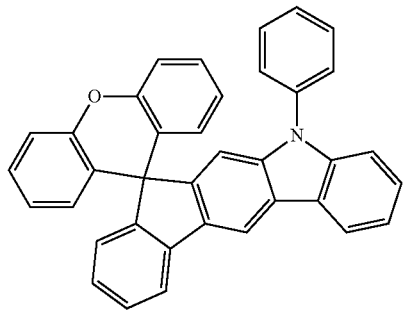

A-1

-continued

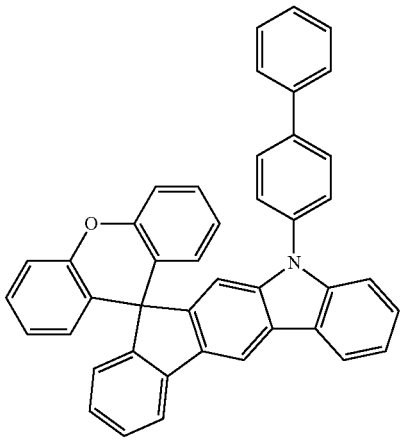

A-2

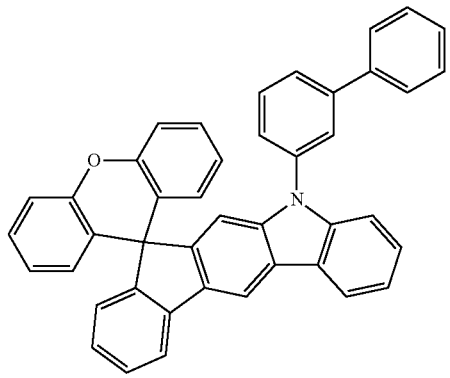

A-3

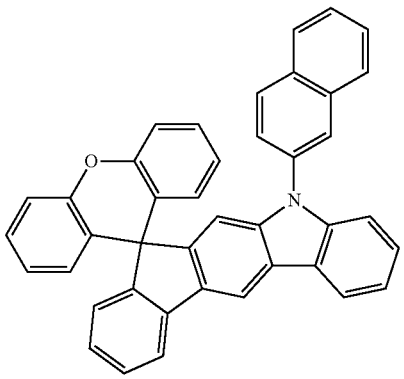

A-4

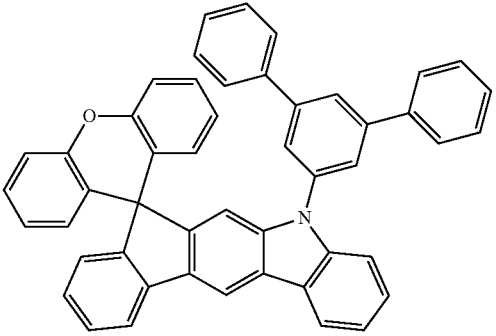

A-5

-continued
A-6
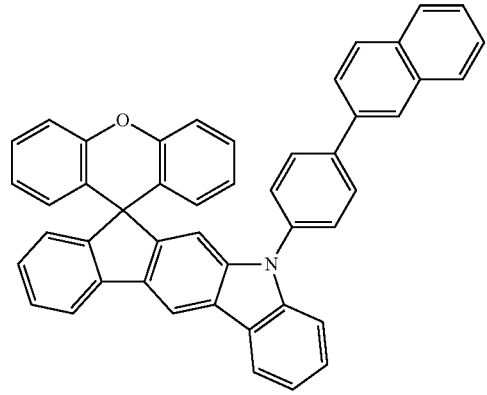
A-7
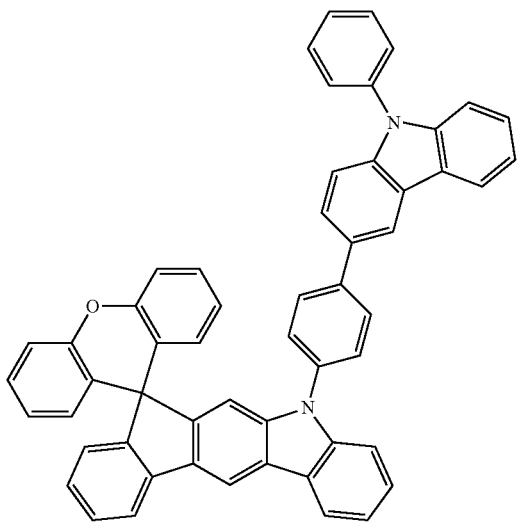
A-8
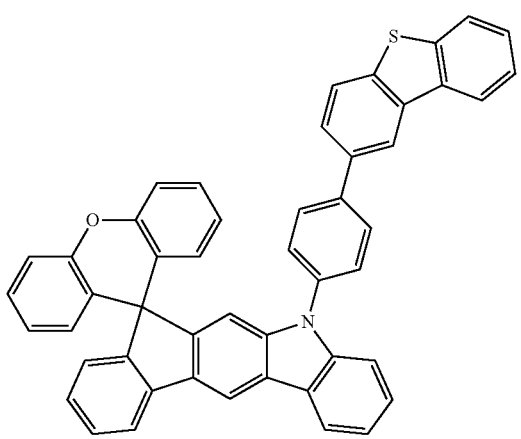
-continued
A-9
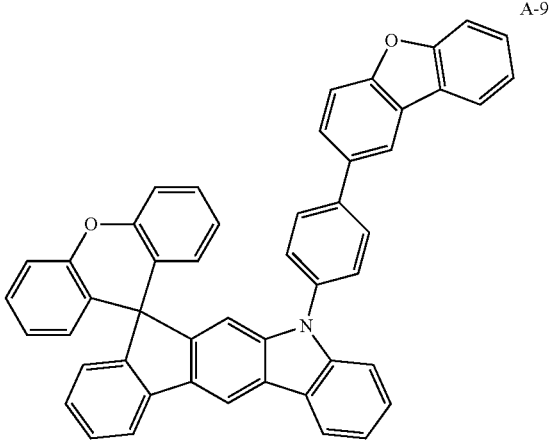
A-10
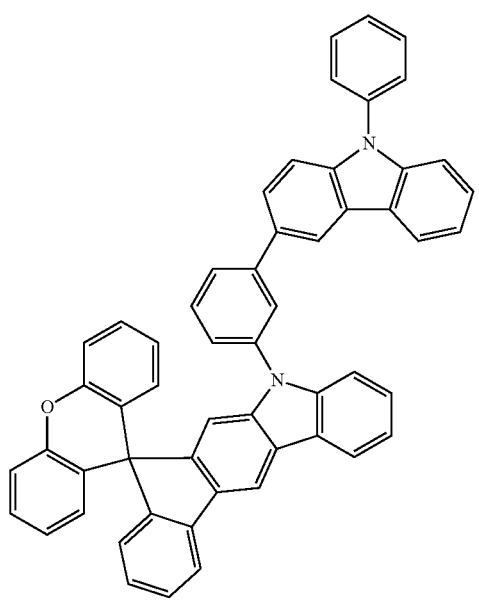
A-11
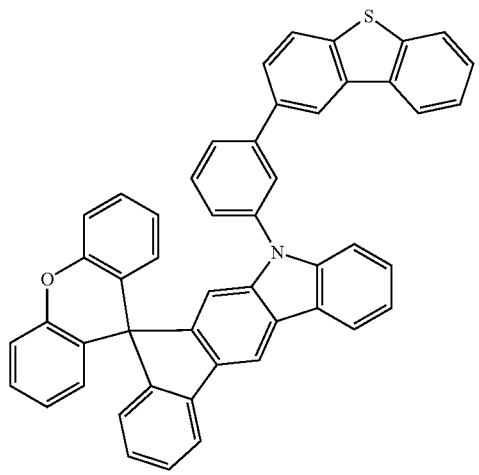

A-12
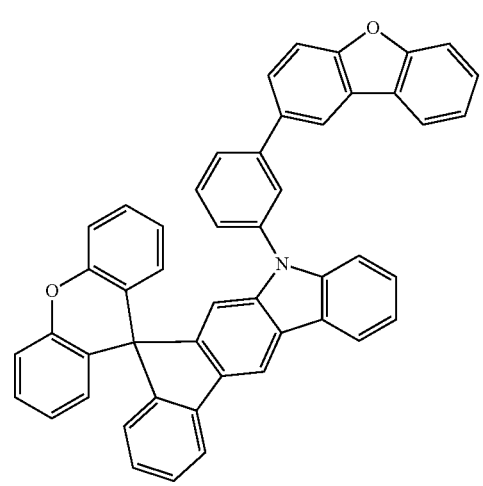
A-13
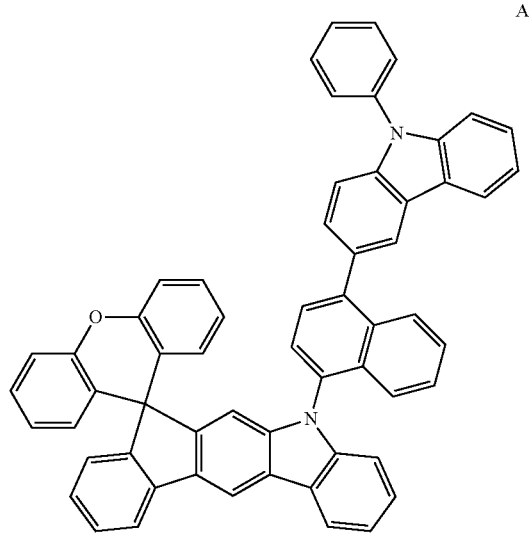
A-14
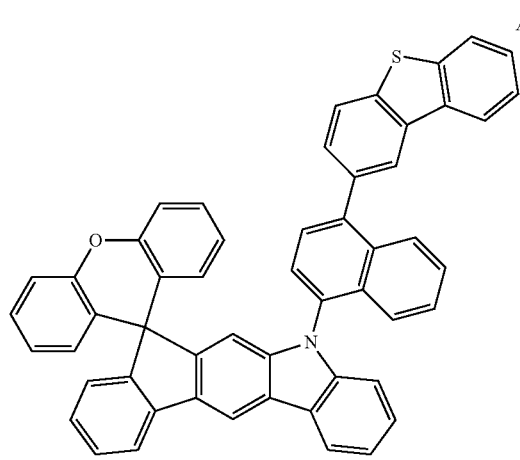
A-15
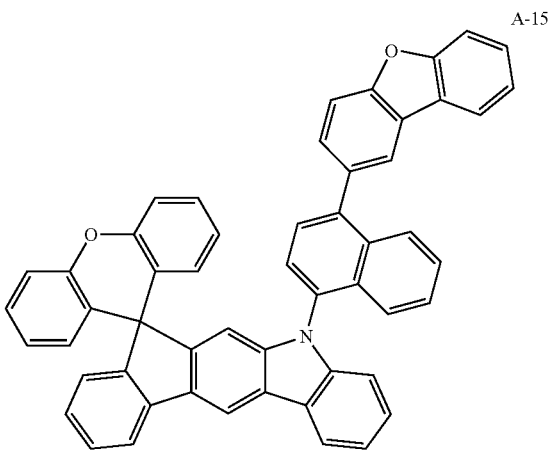
A-16
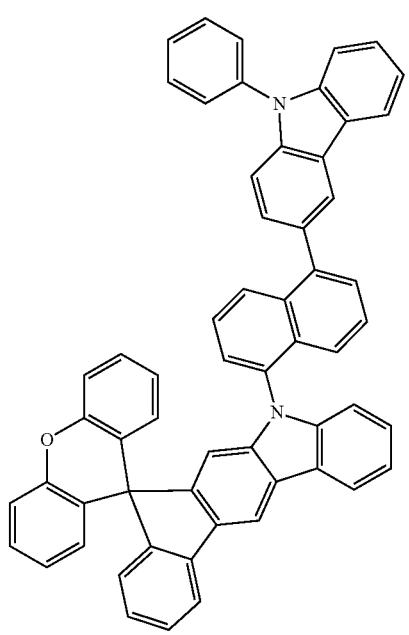

A-17
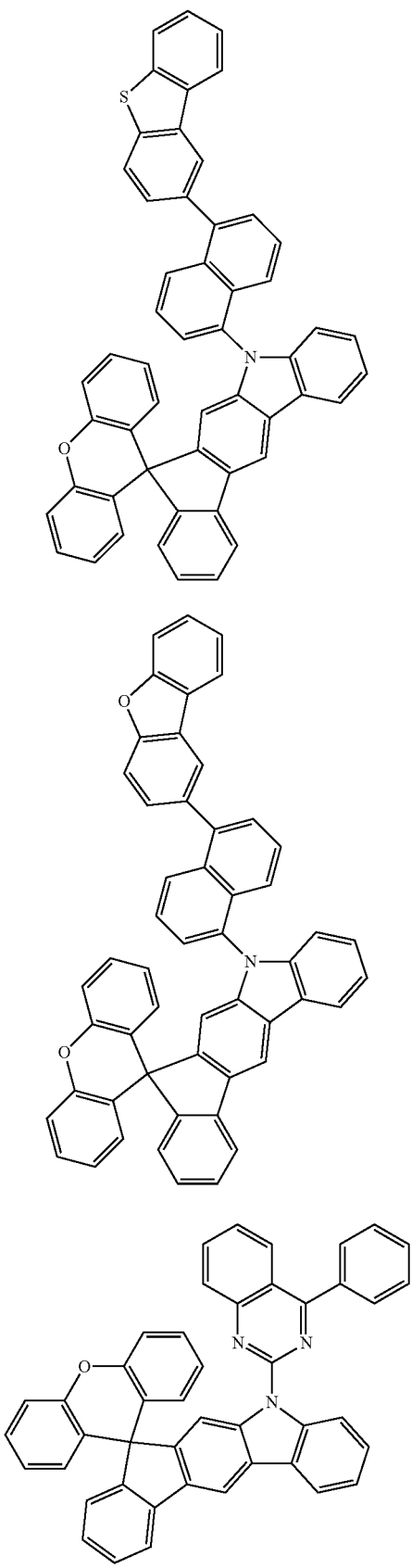
A-18
A-19
A-20
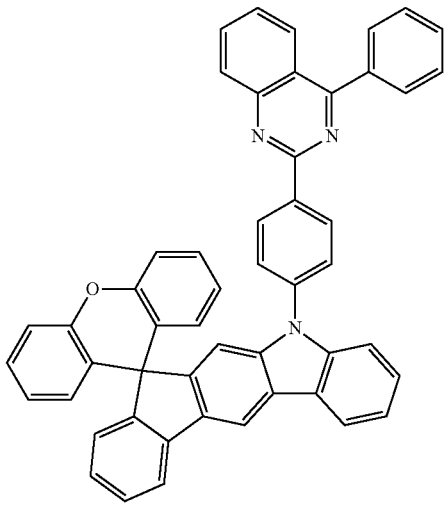
A-21
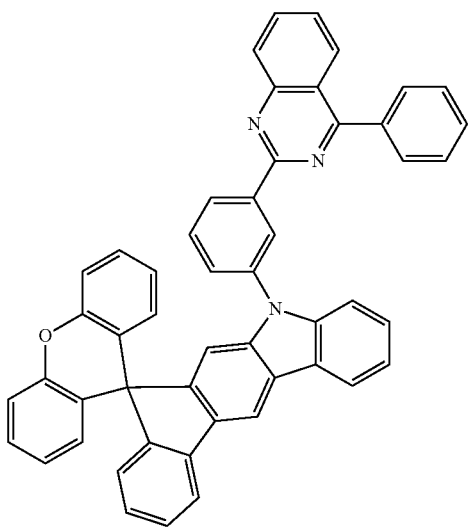
A-22
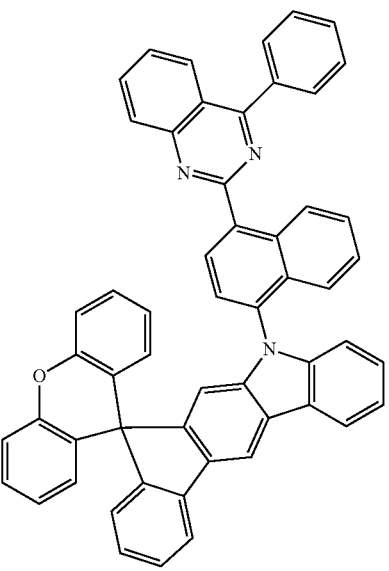

A-23
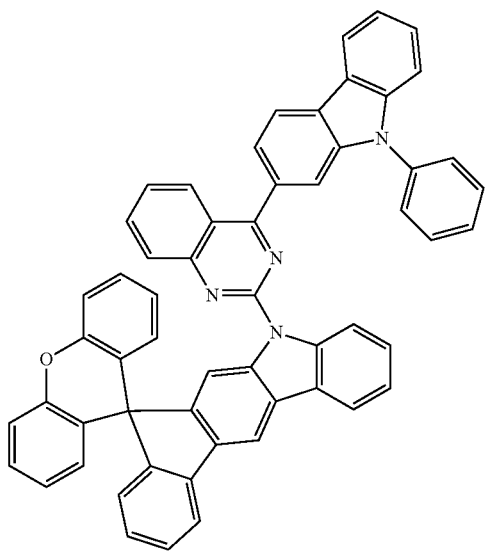
A-24
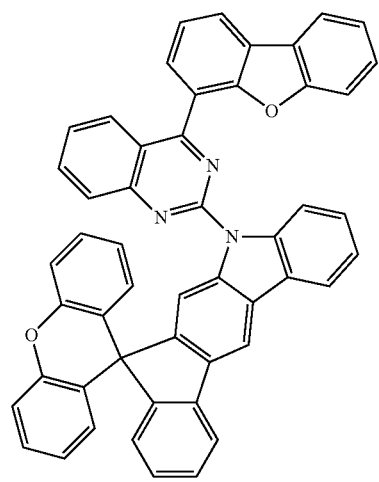
A-25
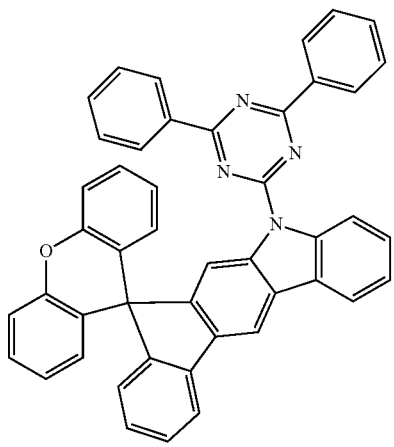
A-26
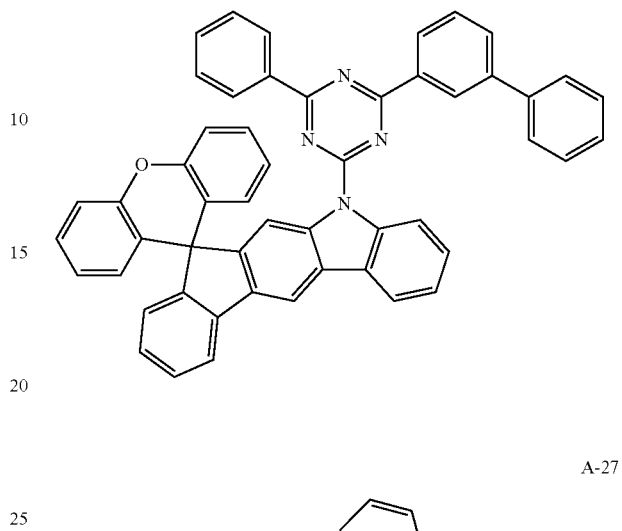
A-27
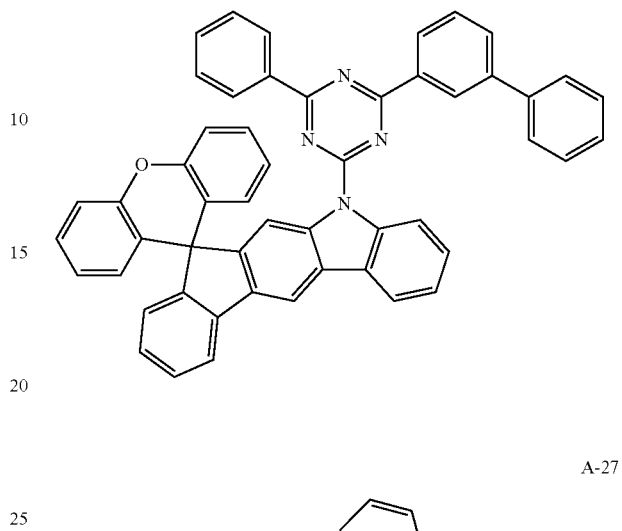
A-28
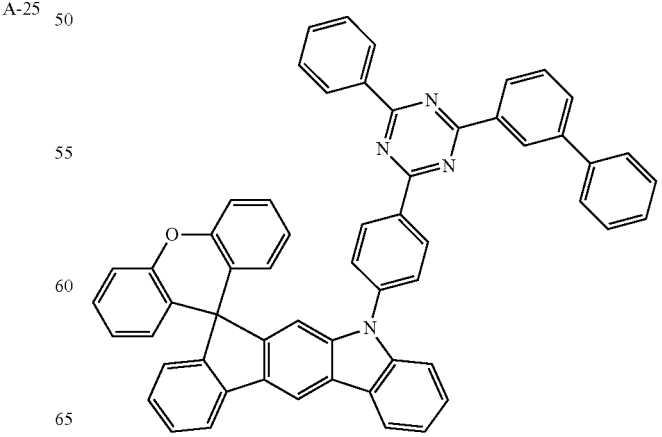

A-29
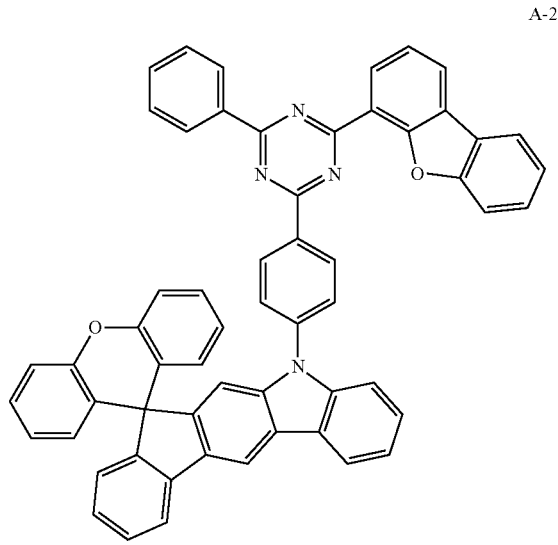
A-30
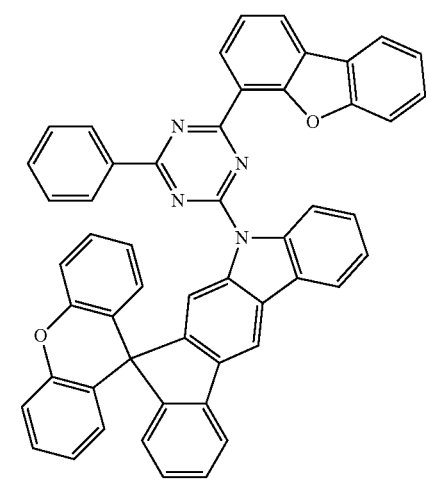
A-31
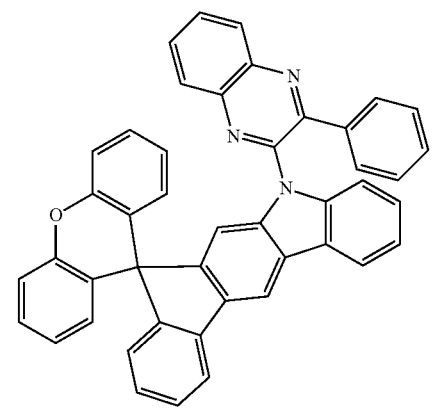
A-32
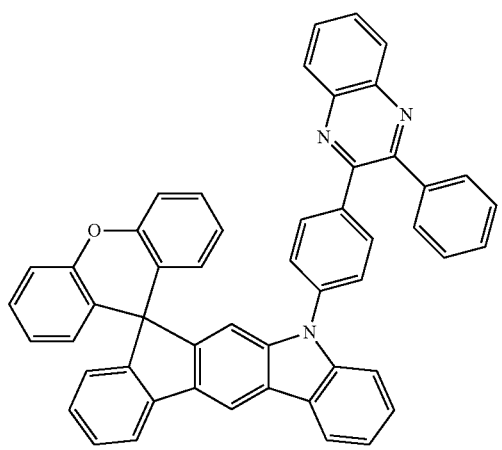
A-33
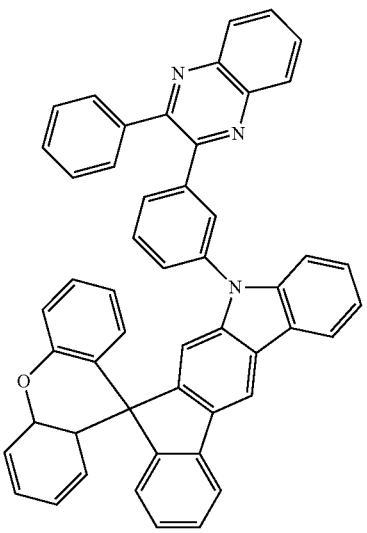
A-34
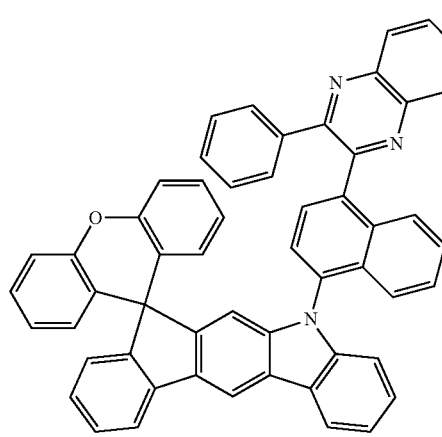

A-35
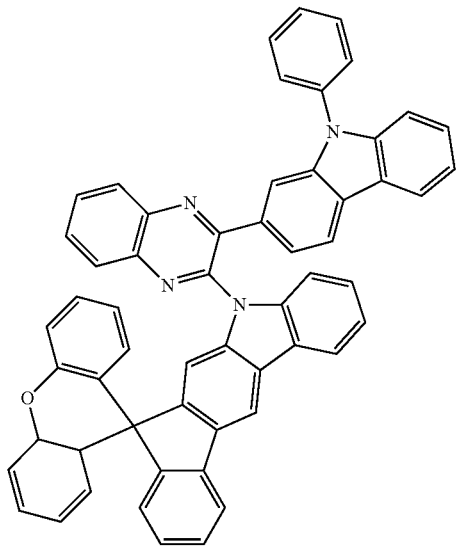
A-36
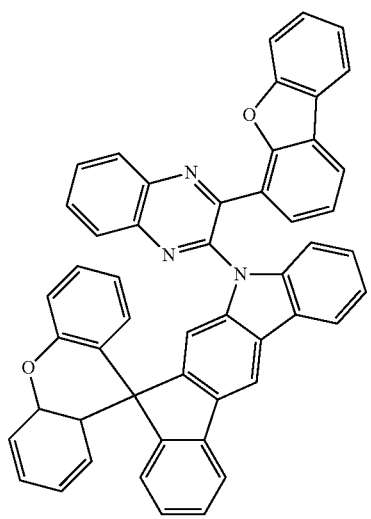
A-37
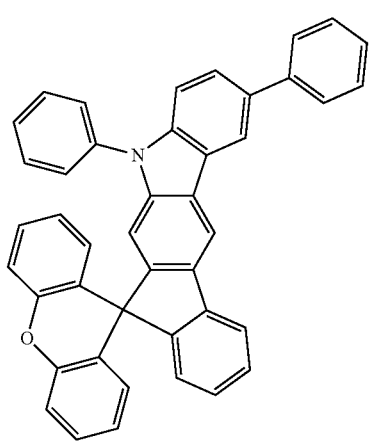
A-38
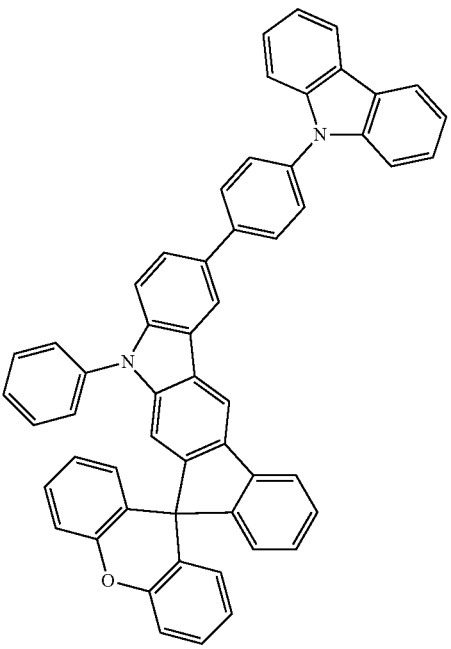
A-39
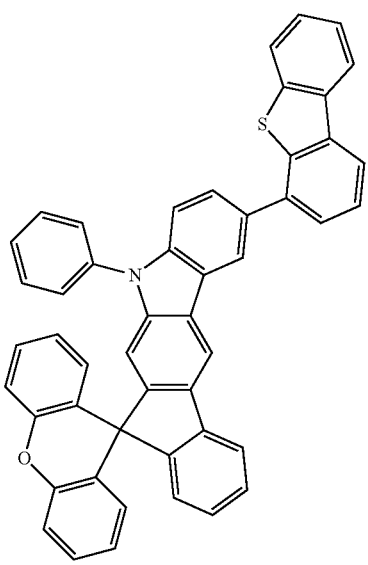

A-40
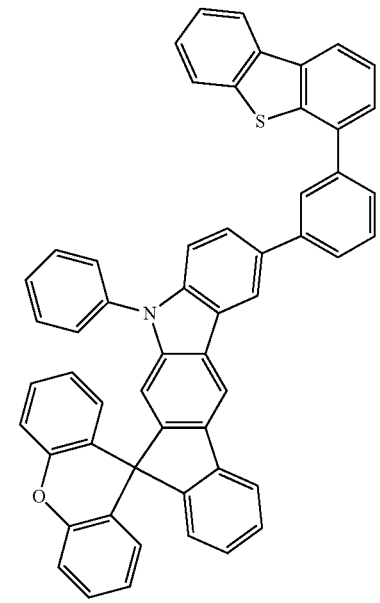
A-41
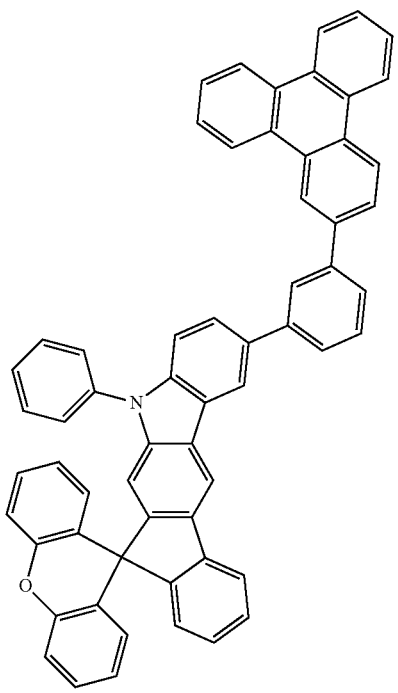
A-42
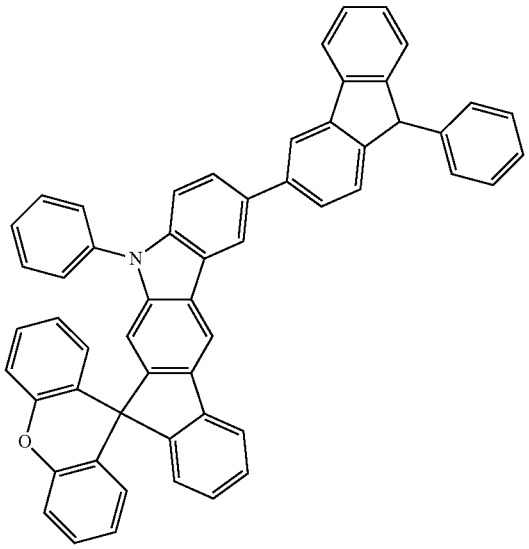
A-43
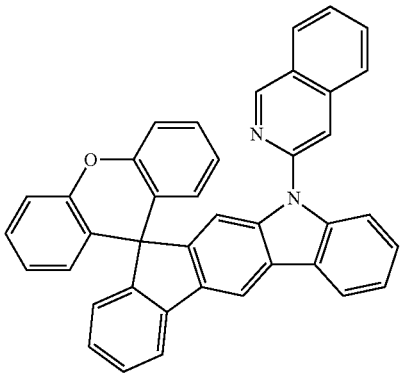
A-44
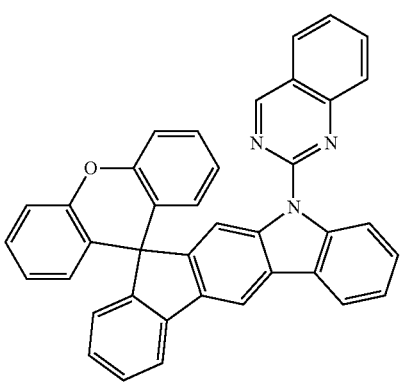

A-45
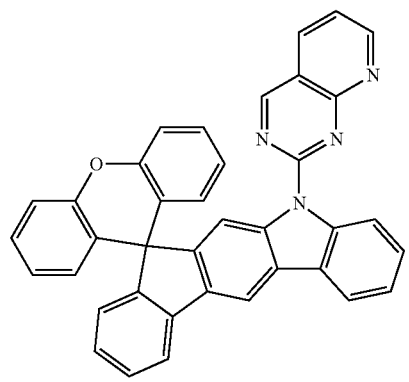
A-46
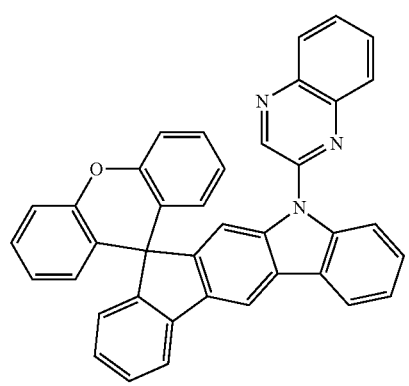
A-47
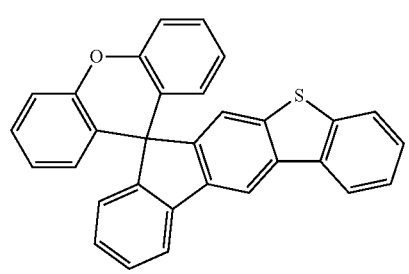
A-48
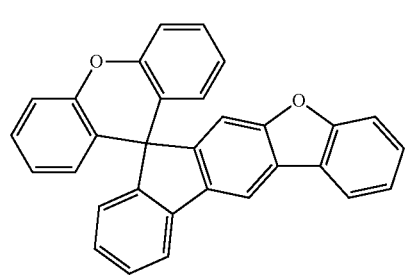
A-49
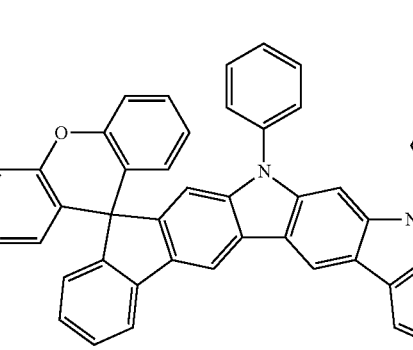
A-50
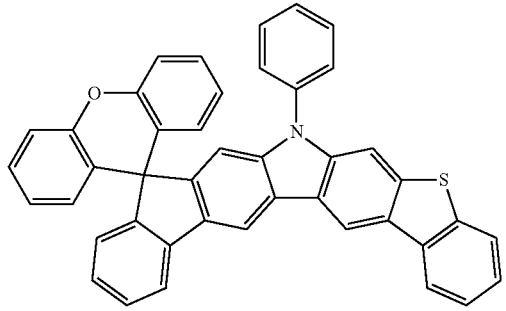
A-51
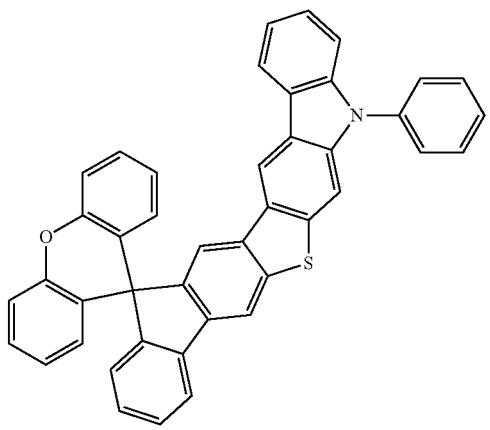
A-52
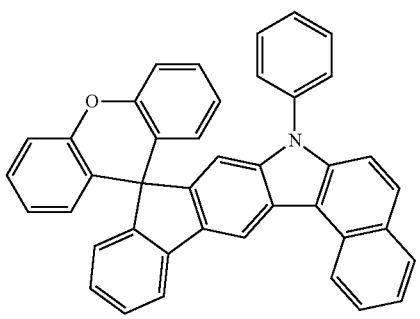
A-53
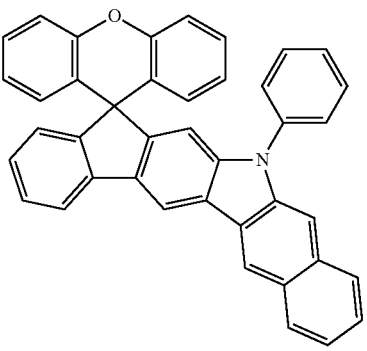

A-54
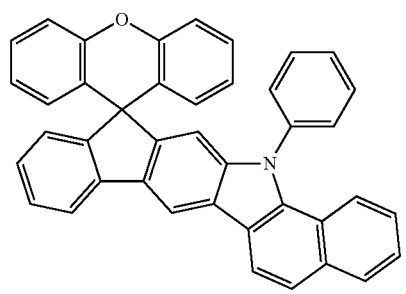
A-55
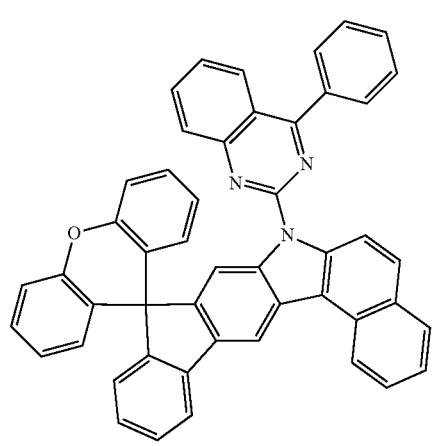
A-56
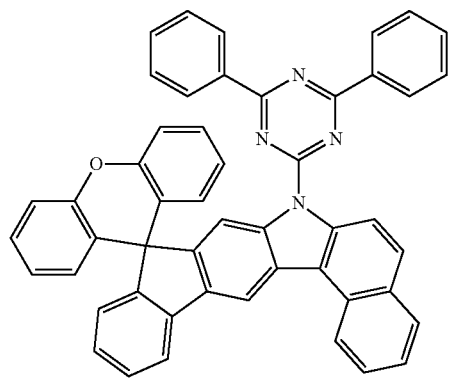
A-57
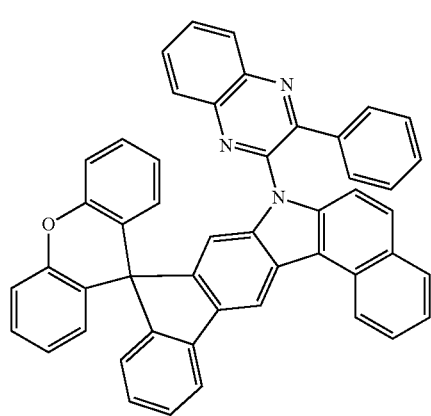
A-58
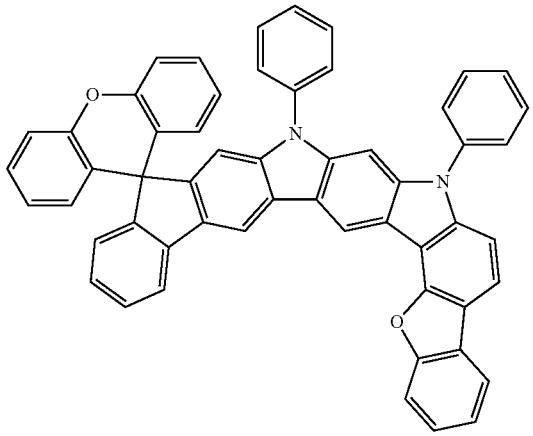
A-59
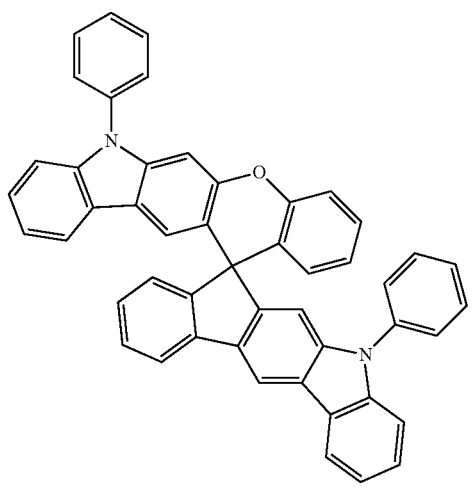
A-60
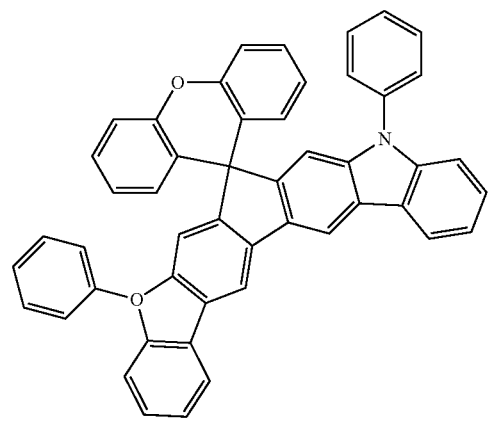

A-61
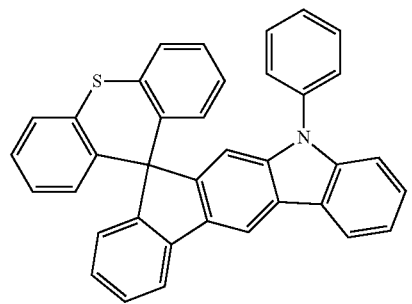
A-62
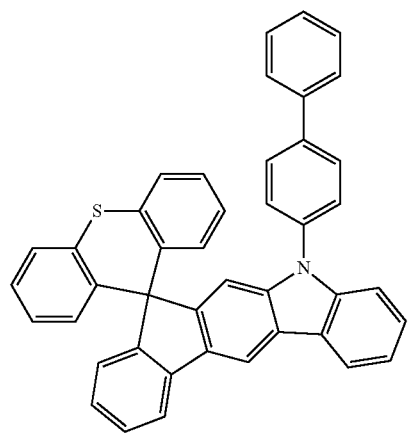
A-63
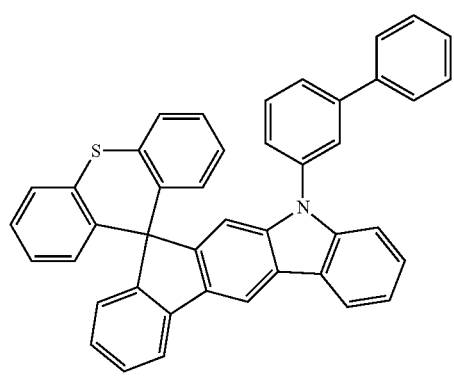
A-64
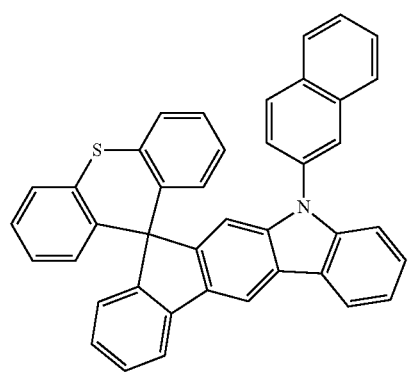
A-65
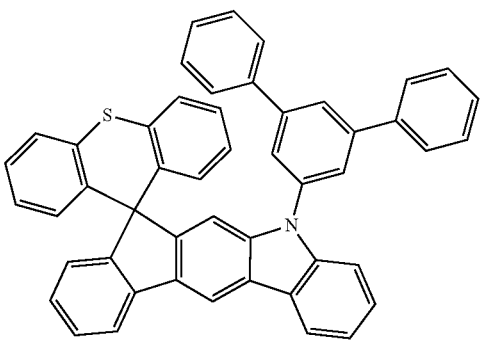
A-66
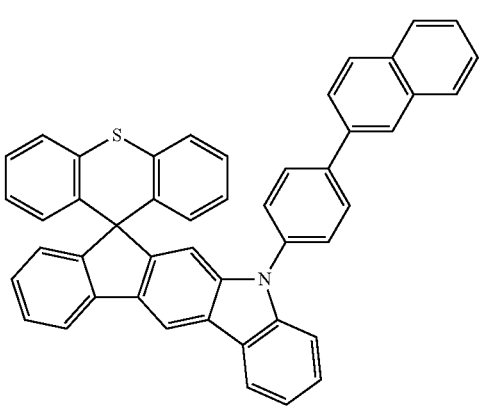
A-67
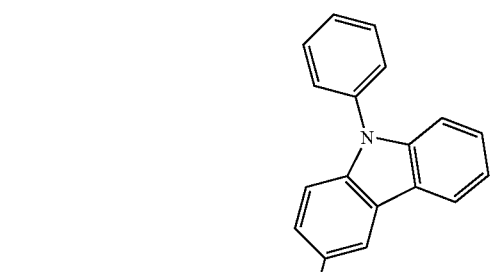
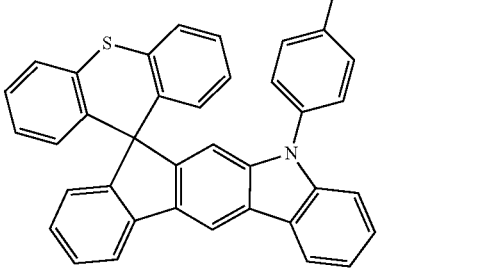

-continued
A-68
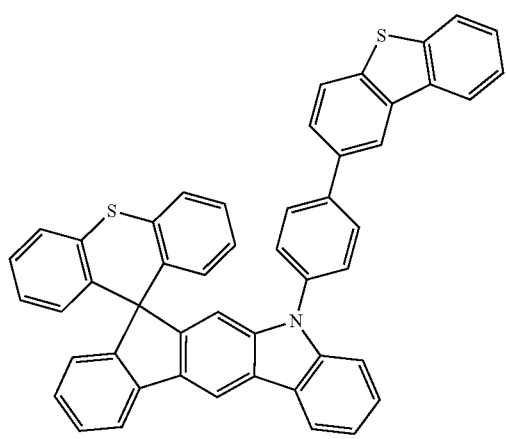
A-69
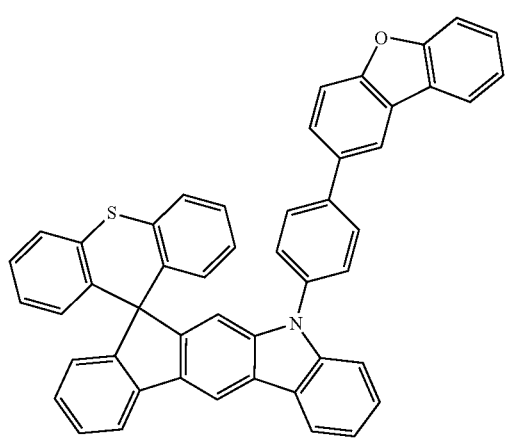
A-70
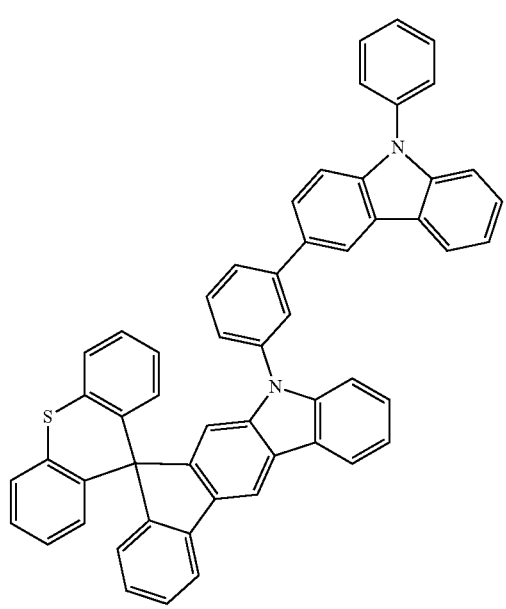
-continued
A-71
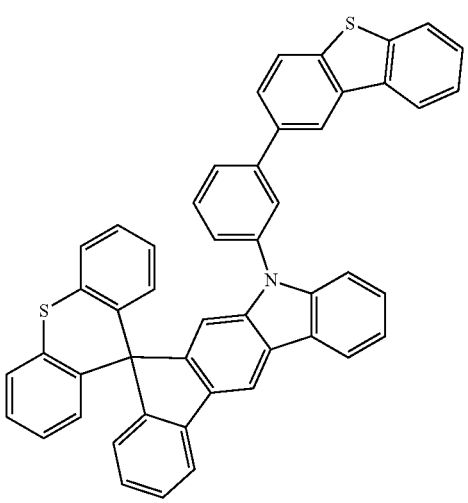
A-72
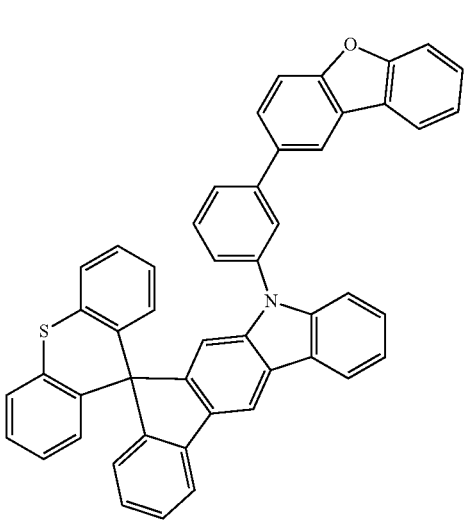
A-73
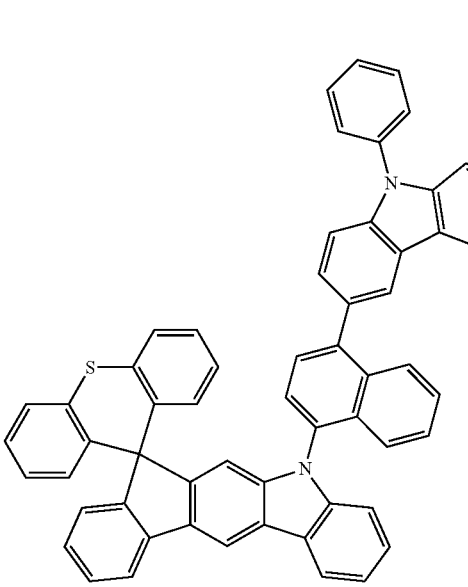

-continued
A-74
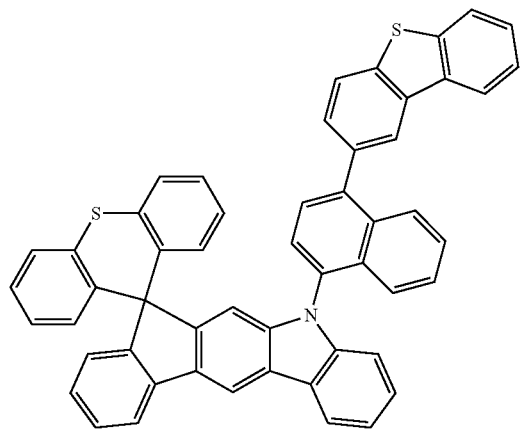
A-75
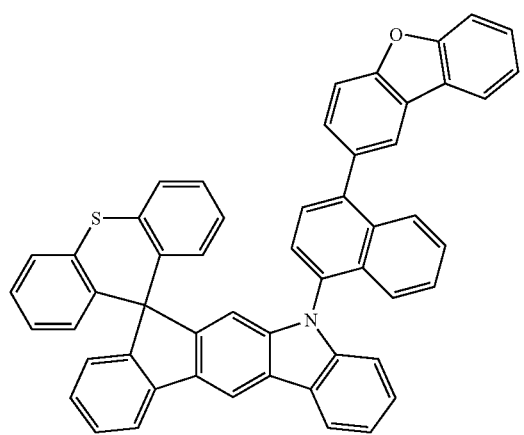
A-76
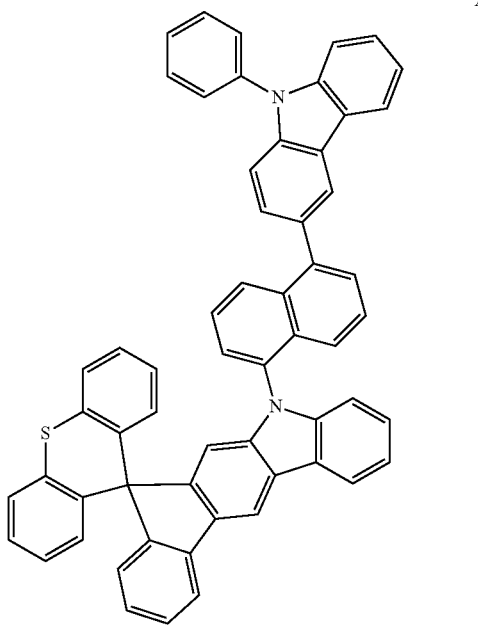
-continued
A-77
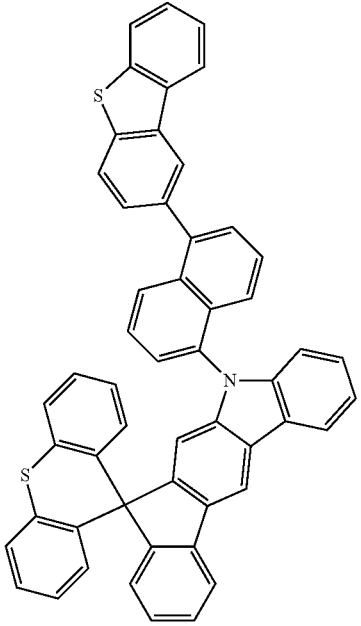
A-78
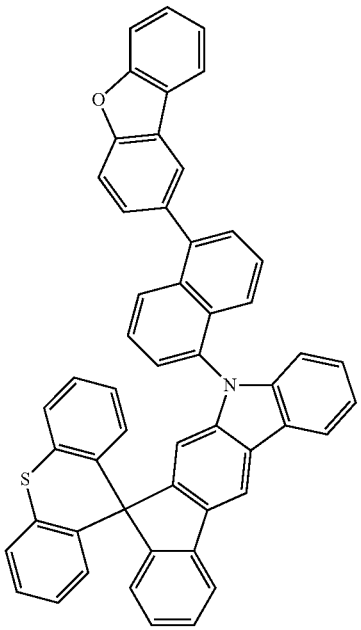

-continued
A-79
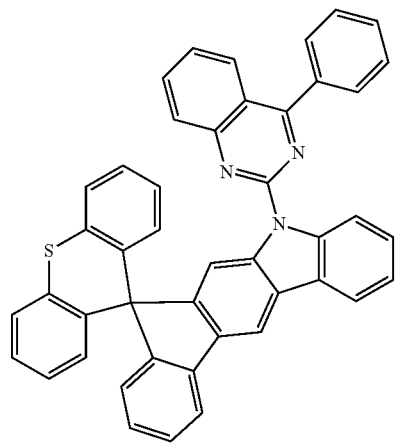
A-80
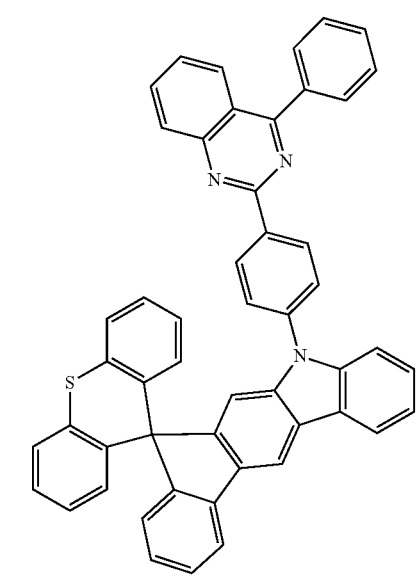
A-81
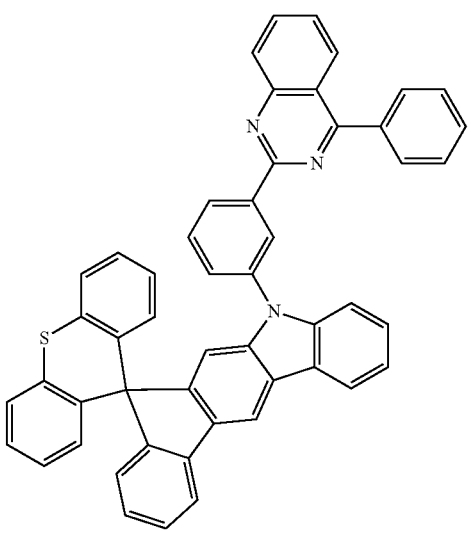
-continued
A-82
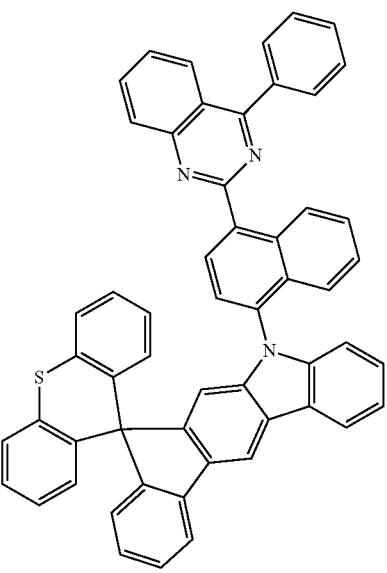
A-83
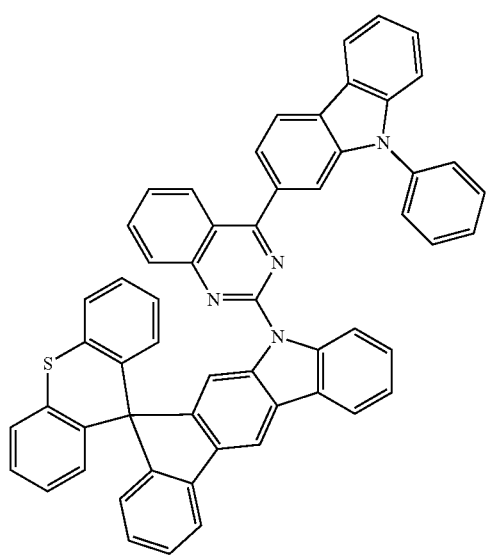
A-84
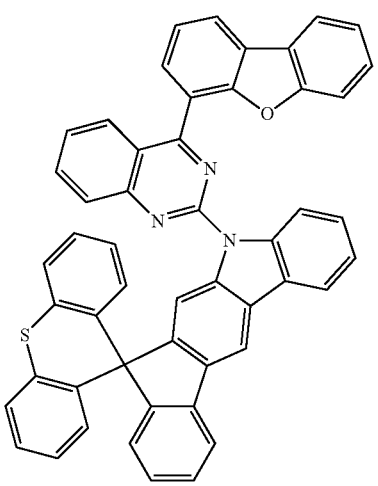

A-85
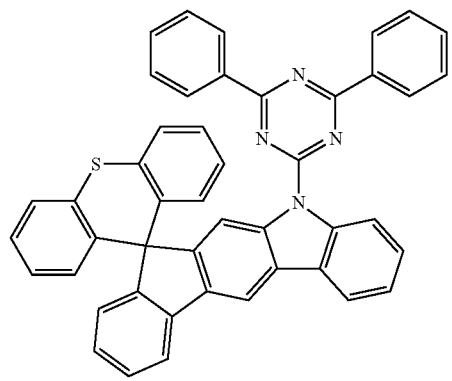
A-86
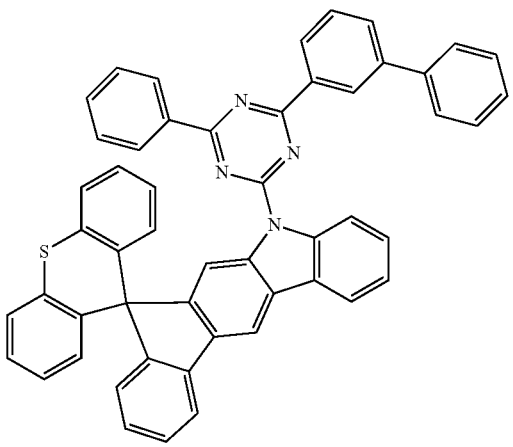
A-87
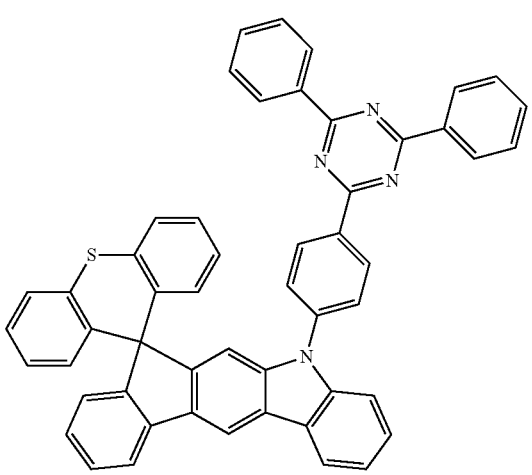
A-88
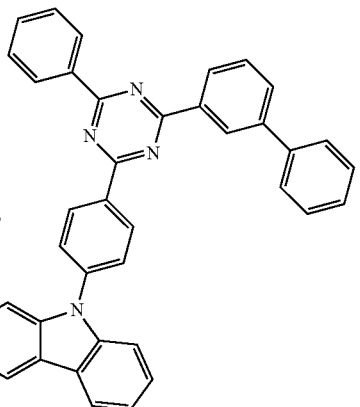
A-89
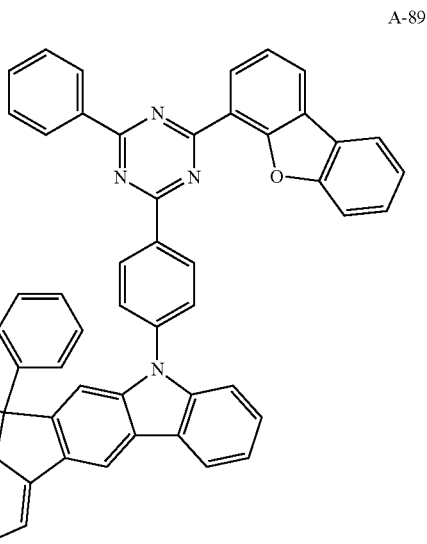
A-90
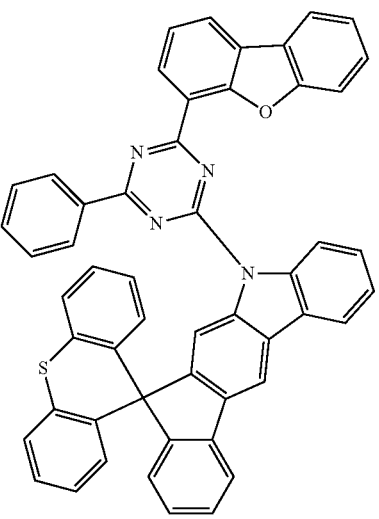

A-91

A-92

A-93

A-94

A-95

A-96

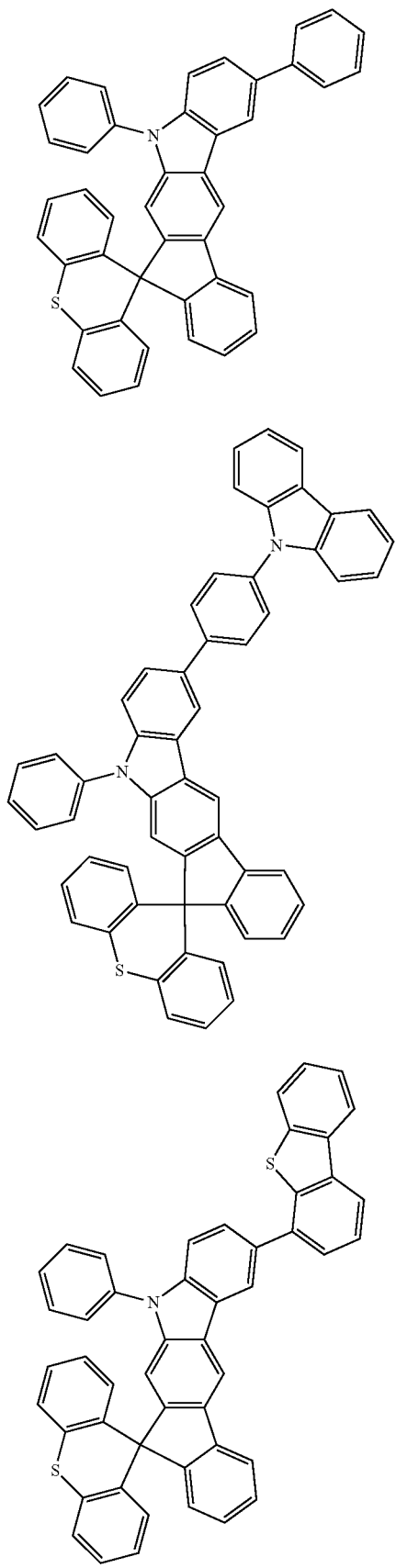
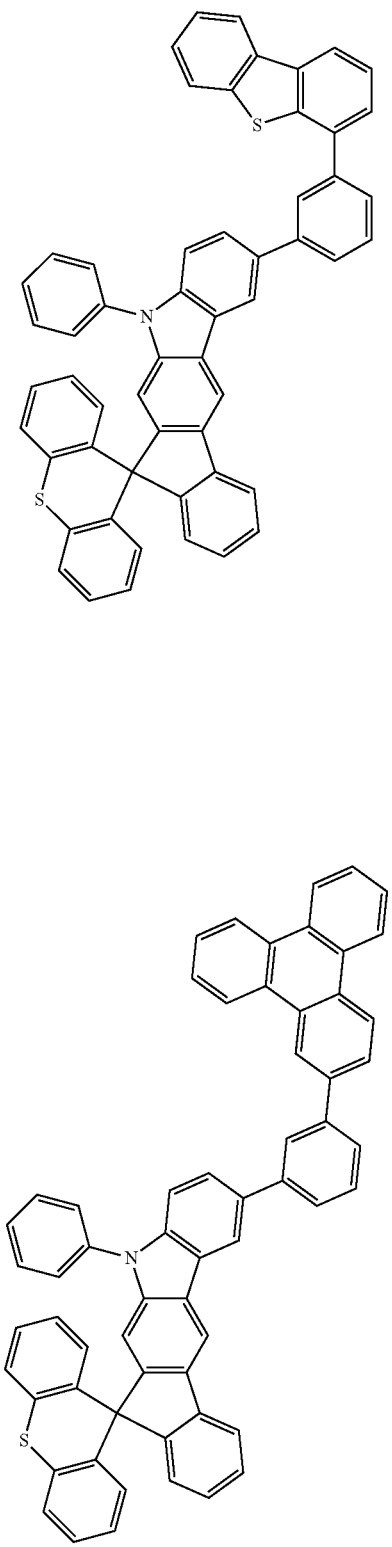

A-102
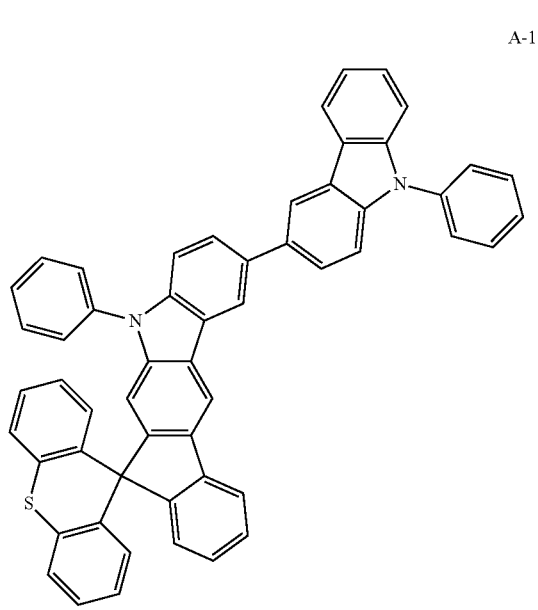
A-103
A-104
A-105
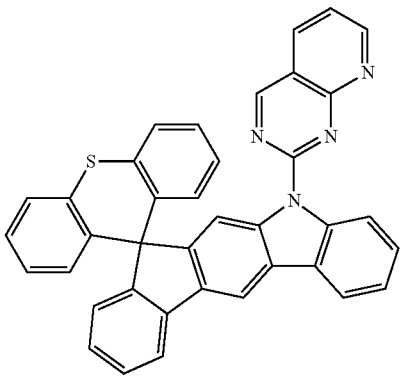
A-106
A-107
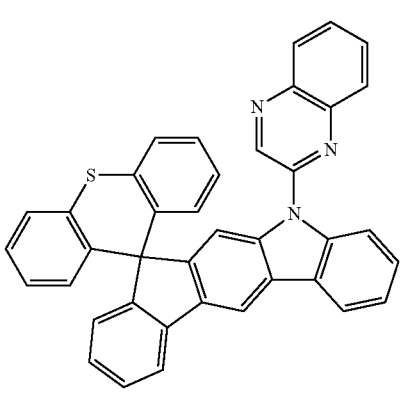
A-108
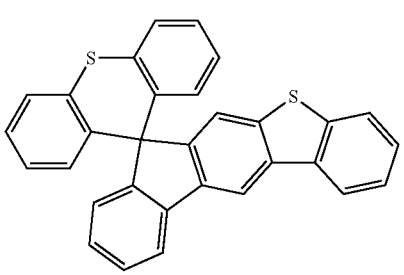
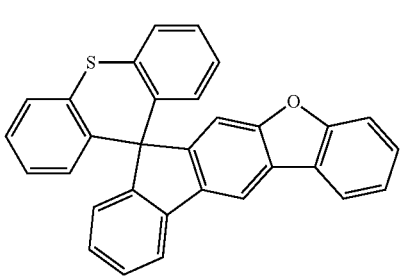

A-109
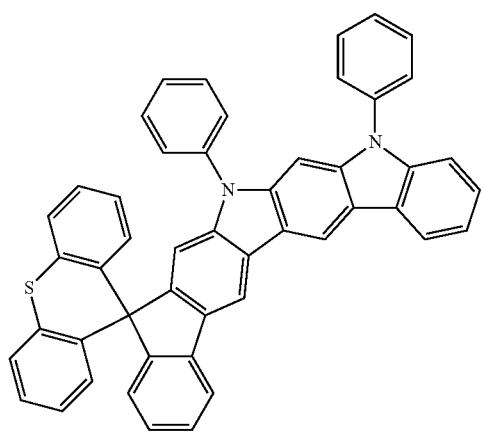
A-110
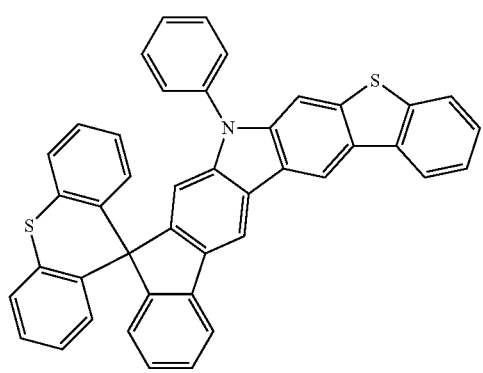
A-111
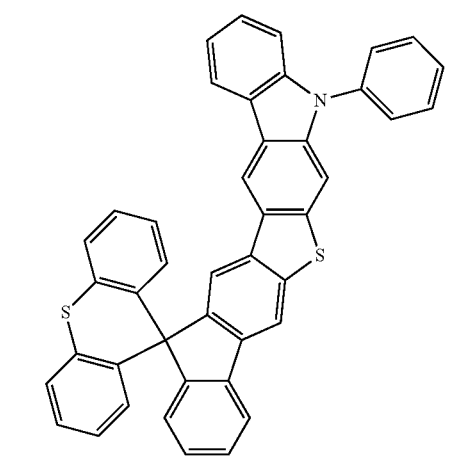
A-112
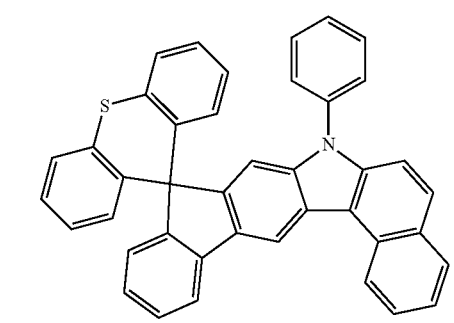
A-113
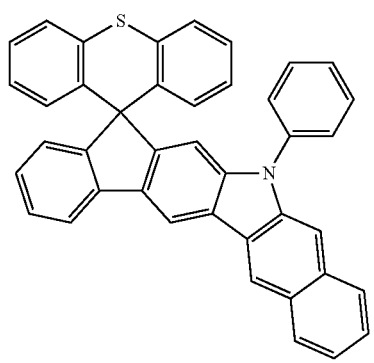
A-114
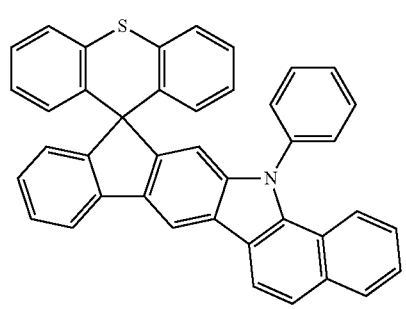
A-115
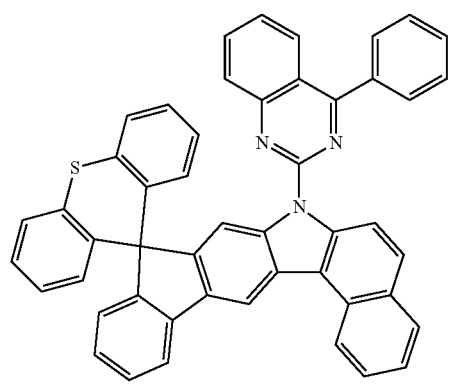
A-116
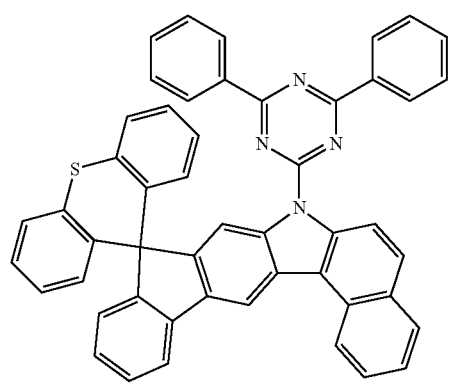

-continued
A-117
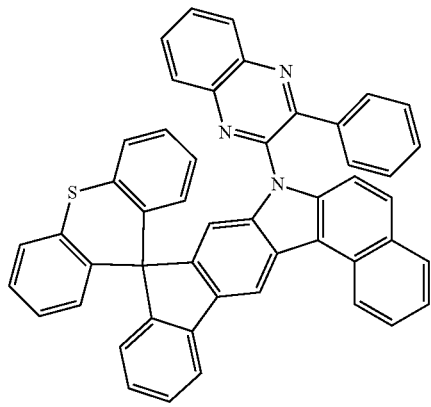
A-118
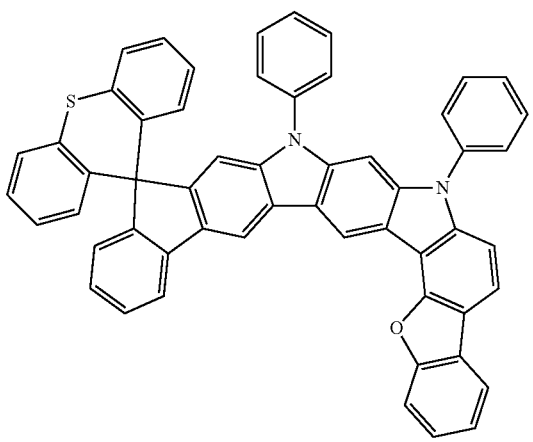
A-119
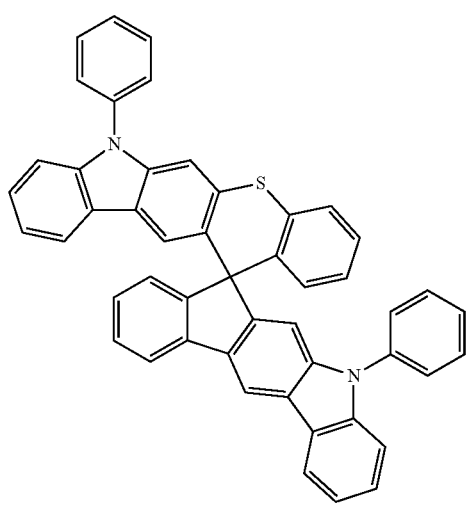
-continued
A-120
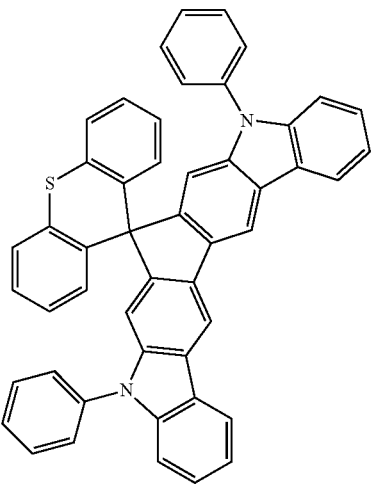
A-121
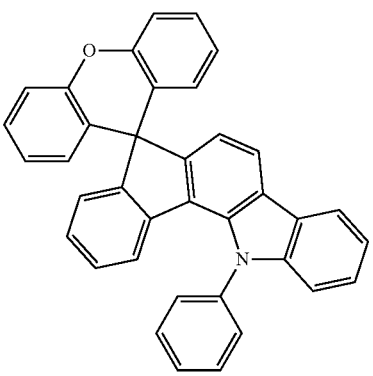
A-122
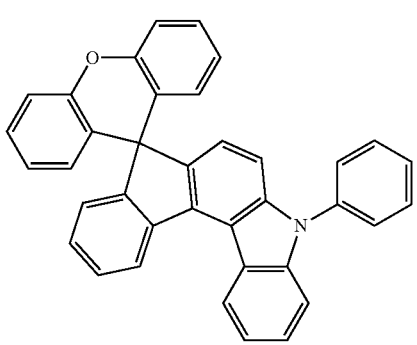
A-123
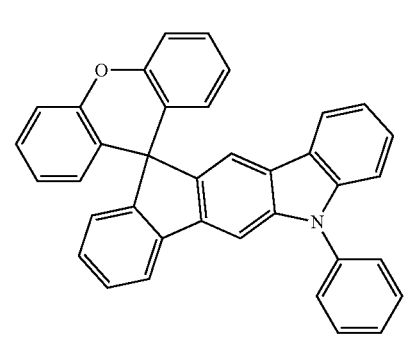

A-124
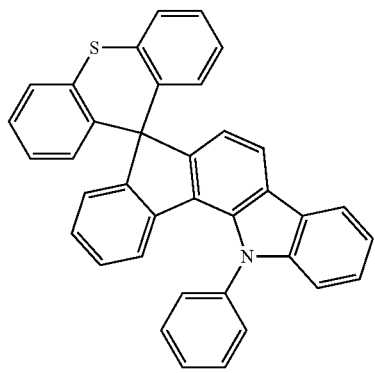
A-125
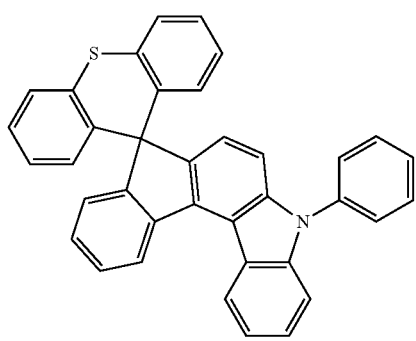
A-126
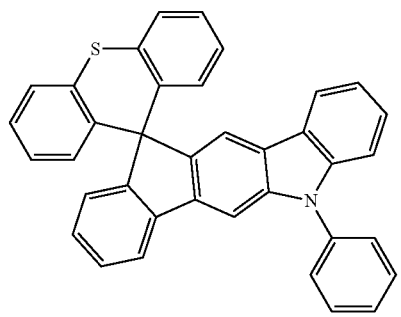
A-127
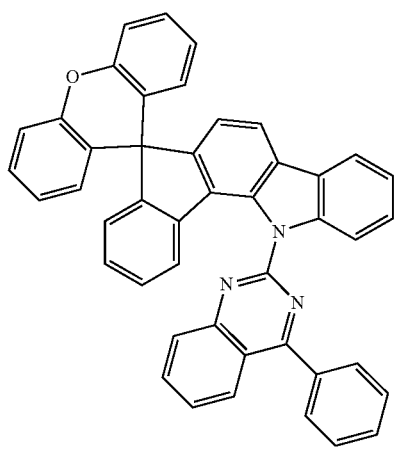
A-128
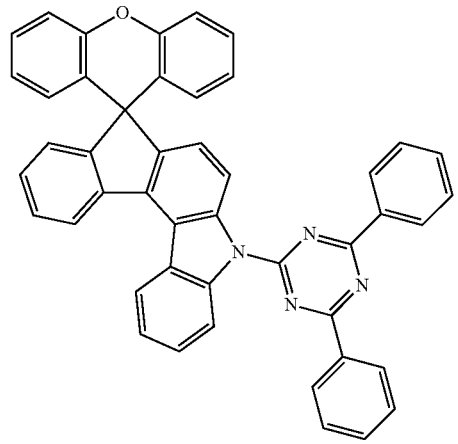
A-129
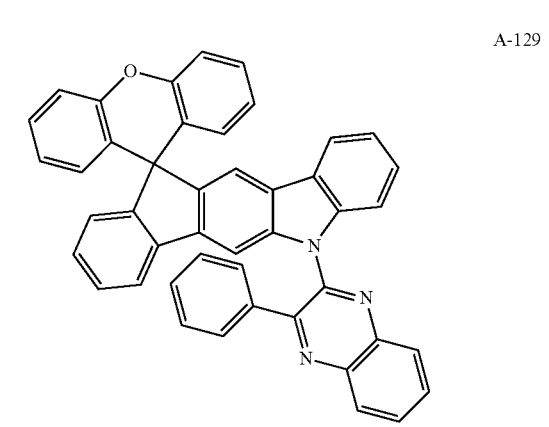
A-130
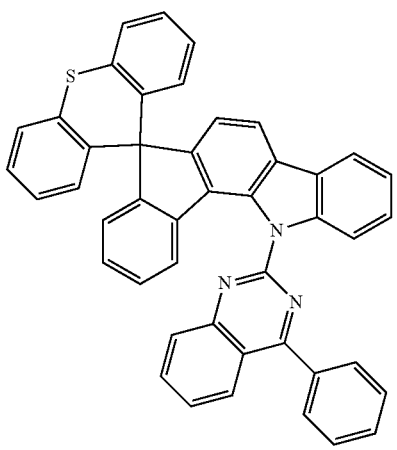

A-131
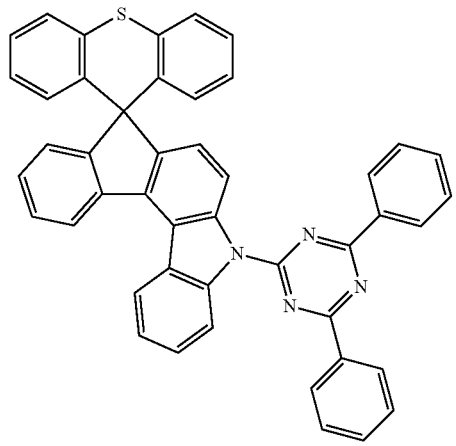
A-132
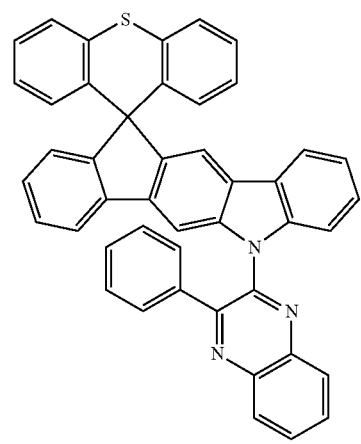
A-133
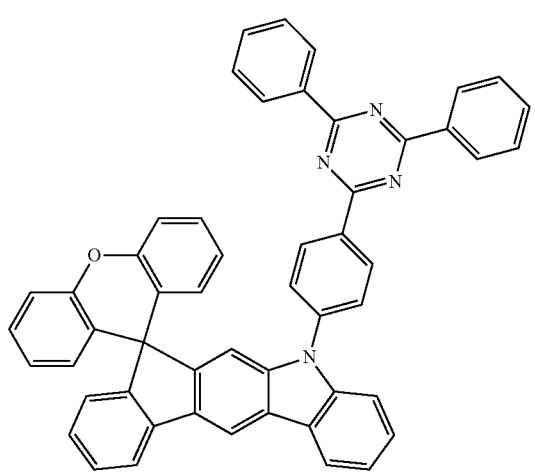
A-134
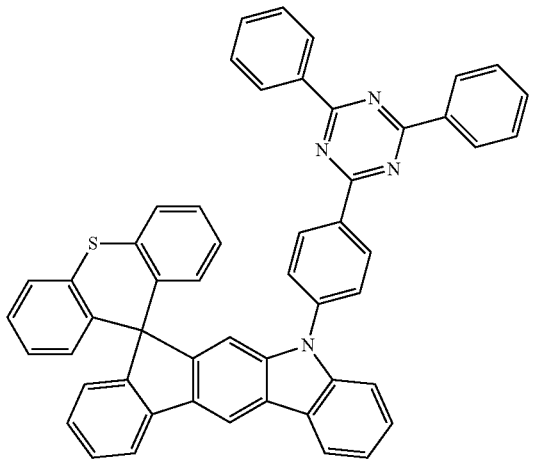
A-135
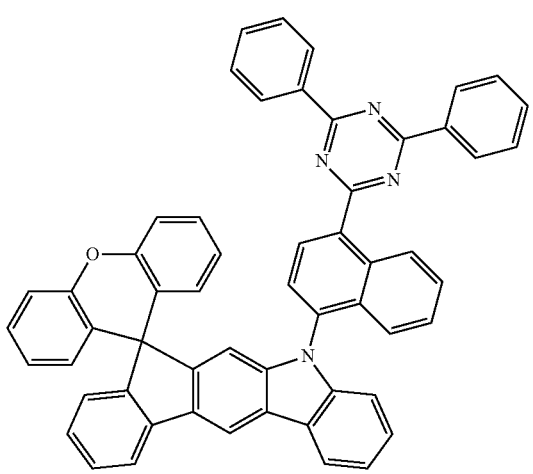
A-136
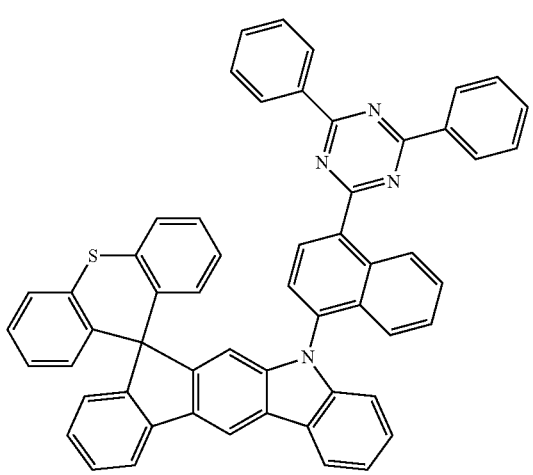

A-137
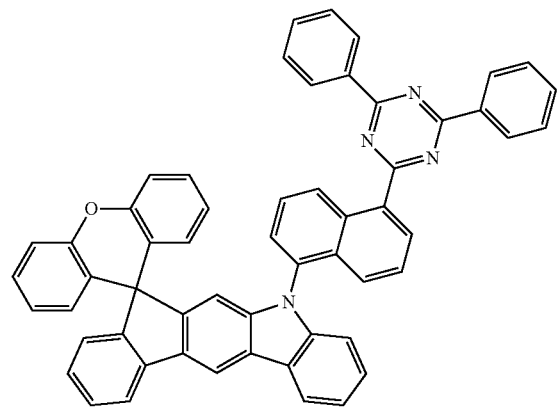
A-138
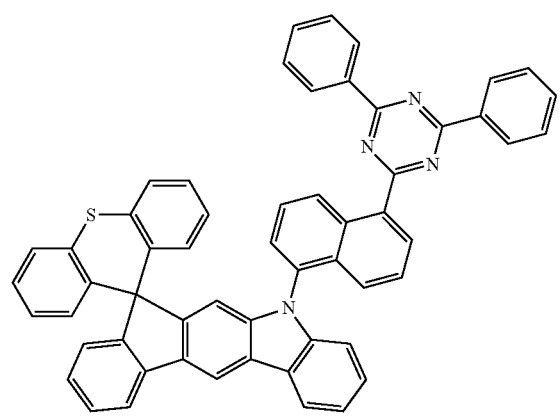
A-139
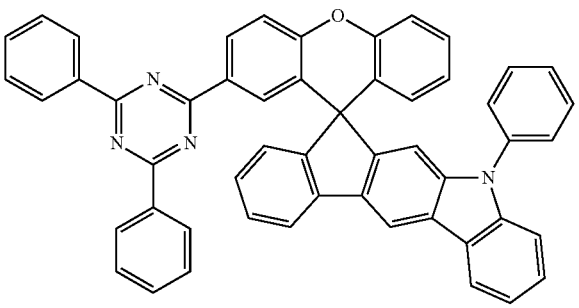
A-140
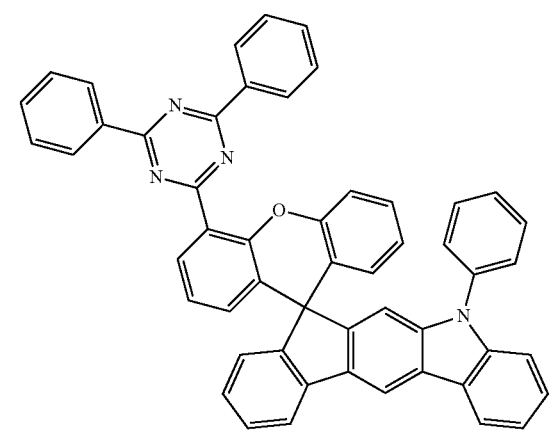
A-141
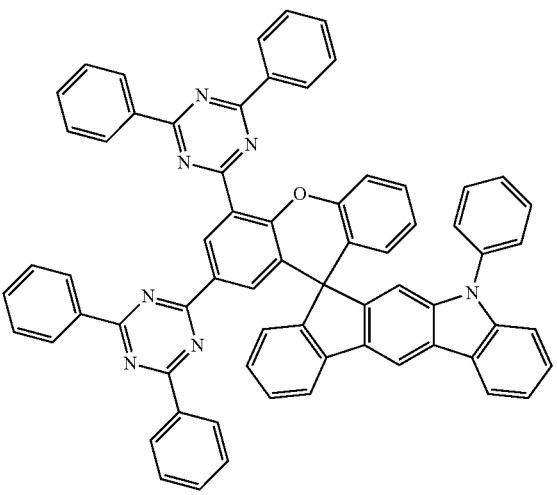
A-142
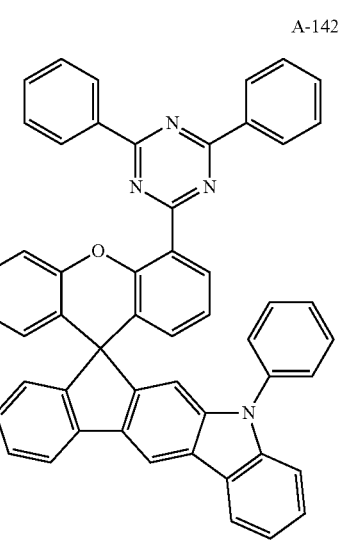
A-143
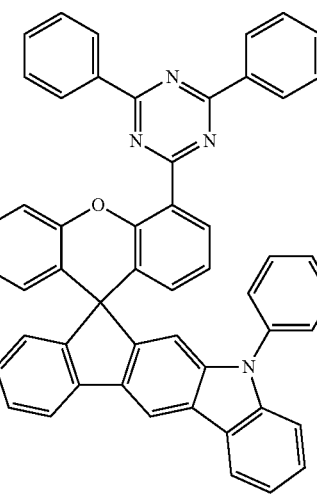
6. An organic electroluminescent device comprising the compound according to claim 1.
* * * * *